US012557986B2

(12) United States Patent
Dave et al.

(10) Patent No.: US 12,557,986 B2
(45) Date of Patent: Feb. 24, 2026

(54) EYE EXAMINATION METHOD AND SYSTEM

(71) Applicant: PlenOptika, Inc., Cambridge, MA (US)

(72) Inventors: Shivang R. Dave, Boston, MA (US); Daryl Lim, Singapore (SG)

(73) Assignee: PLENOPTIKA, INC., Cambridge, MA (US)

( * ) Notice: Subject to any disclaimer, the term of this patent is extended or adjusted under 35 U.S.C. 154(b) by 205 days.

(21) Appl. No.: 18/559,027

(22) PCT Filed: May 6, 2022

(86) PCT No.: PCT/US2022/072186
§ 371 (c)(1),
(2) Date: Nov. 3, 2023

(87) PCT Pub. No.: WO2022/236333
PCT Pub. Date: Nov. 10, 2022

(65) Prior Publication Data
US 2024/0225442 A1 Jul. 11, 2024

Related U.S. Application Data

(60) Provisional application No. 63/185,158, filed on May 6, 2021.

(51) Int. Cl.
*A61B 3/15* (2006.01)
*A61B 3/00* (2006.01)
*A61B 3/10* (2006.01)

(52) U.S. Cl.
CPC ............ *A61B 3/152* (2013.01); *A61B 3/0025* (2013.01); *A61B 3/0083* (2013.01); *A61B 3/1015* (2013.01); *A61B 2560/0431* (2013.01)

(58) Field of Classification Search
CPC ... A61B 3/0016; A61B 3/0025; A61B 3/0033; A61B 3/0083; A61B 3/1015; A61B 3/152; A61B 2560/0431
See application file for complete search history.

(56) References Cited

U.S. PATENT DOCUMENTS

| | | | |
|---|---|---|---|
| 8,733,927 B1 | 5/2014 | Lewis | |
| 9,230,062 B2 | 1/2016 | Seriani | |

(Continued)

FOREIGN PATENT DOCUMENTS

| | | | |
|---|---|---|---|
| CA | 2890564 A1 | 5/2014 | |
| EP | 1590701 A2 | 11/2005 | |

(Continued)

OTHER PUBLICATIONS

Owen, M., "Apple glasses could adjust lenses to match user's prescription," Jan. 11, 2022, pp. 17.

(Continued)

*Primary Examiner* — Jack Dinh
(74) *Attorney, Agent, or Firm* — Hamilton, Brook, Smith & Reynolds, P.C.

(57) ABSTRACT

Clinical-quality eye examinations are provided at locations remote from the physician and outside of a clinical setting. A portable optical device and corresponding software are delivered to the patient's location. The portable optical device is configured for patient use in self-conducting an eye or vision exam and taking optical measurements. As a function of type of optical measurement data or health consideration of the patient, the corresponding software provides uploading and live streaming of the optical measurement data to the physician. The corresponding software is executed during the patient conducting the eye (vision) exam and enables the remotely located physician, to participate in the same via video conference. Alternatively, an artificial intelligence resource operating remotely or locally (Continued)

LIGHT EMITTING DIODES 2070 · TUNABLE OPTICS 2072 · BEAMSPLITTER 2074 · PORTABLE OPTICAL DEVICE 2008

EYE 1754

TRANSPARENT WINDOW 2096

EXTERNAL TARGET 252

BEAMSPLITTER 2076

BEAMSPLITTER 2078

INBOUND LASER INTO THE EYE 2082

LASER DIODE 2080

Laser reflected off retina 2094

CAMERA (WAVEFRONT ABERROMETER) 2084

FOCUSING OPTICS (FOR WAVEFRONT ABERROMETER) 2086

CAMERA (PUPIL CAMERA) 2088

FOCUSING OPTICS (FOR PUPIL CAMERA) 2090

LED LIGHT REFLECTED OFF CORNEA 2092 can provide physician-type guidance and eye health assessments. Alignment of device and patient eyes can be facilitated for remote exams.

20 Claims, 39 Drawing Sheets

(56) References Cited

U.S. PATENT DOCUMENTS

| | | | |
|---|---|---|---|
| 9,492,074 | B1 | 11/2016 | Lee et al. |
| 9,749,451 | B2 | 8/2017 | Hoellwarth |
| 9,854,965 | B2 | 1/2018 | Durr et al. |
| 10,028,653 | B2 | 7/2018 | Alberts et al. |
| 10,083,279 | B2 | 9/2018 | Seriani |
| 10,665,345 | B2 | 5/2020 | Seriani |
| 10,786,150 | B2 | 9/2020 | Durr et al. |
| 10,827,925 | B2 | 11/2020 | Fried et al. |
| 10,852,553 | B2 | 12/2020 | Pedder et al. |
| 10,983,352 | B2 | 4/2021 | Chan et al. |
| 11,054,336 | B2 | 7/2021 | Limon et al. |
| 11,096,576 | B2 | 8/2021 | Dave et al. |
| 11,209,654 | B1 | 12/2021 | Lewis |
| 11,221,479 | B2 | 1/2022 | Zhao et al. |
| 11,294,203 | B2 | 4/2022 | Lewis |
| 11,391,906 | B2 | 7/2022 | Hudman |
| 11,428,937 | B2 | 8/2022 | Lewis |
| 11,428,955 | B1 | 8/2022 | Lewis |
| 11,630,311 | B1 | 4/2023 | Lewis |
| 2006/0170864 | A1 | 8/2006 | Kuiper et al. |
| 2013/0250191 | A1 | 9/2013 | Blum et al. |
| 2014/0218681 | A1 | 8/2014 | Spratt et al. |
| 2015/0042957 | A1 | 2/2015 | Abitbol et al. |
| 2016/0171596 | A1 | 6/2016 | Angerbauer et al. |
| 2016/0310000 | A1 | 10/2016 | Meneghini |
| 2017/0027436 | A1 | 2/2017 | Lee et al. |
| 2017/0172406 | A1 | 6/2017 | Pamplona et al. |
| 2017/0245758 | A1 | 8/2017 | Liang |
| 2018/0220888 | A1 | 8/2018 | Tumlinson et al. |
| 2020/0046222 | A2 | 2/2020 | Dave et al. |
| 2020/0174284 | A1 | 6/2020 | Chan et al. |
| 2023/0132807 | A1 | 5/2023 | Marin et al. |
| 2023/0258944 | A1 | 8/2023 | Bolis et al. |

FOREIGN PATENT DOCUMENTS

| | | |
|---|---|---|
| EP | 2967324 B1 | 9/2021 |
| WO | 2013/096775 A1 | 6/2013 |
| WO | 2014/144918 A3 | 1/2015 |
| WO | 2015003062 A1 | 1/2015 |
| WO | 2015003086 A1 | 1/2015 |
| WO | 2020010138 A1 | 1/2020 |
| WO | 2021038421 A1 | 3/2021 |
| WO | 2022/009233 A1 | 1/2022 |
| WO | 2022/032198 A1 | 2/2022 |
| WO | 2022/236333 A2 | 11/2022 |

OTHER PUBLICATIONS

Owen, M., "Apple VR headset may use fluid-filled lenses to counter a user's bad eyesight.," Dec. 1, 2020, pp. 17.

Spoonauer, M., "Vision Pro review: A revolution in progress," May 2, 2024, pp. 28.

Amazon, "Pure Plan Neck Shoulder Relaxer Traction Device for TMJ Pain Relief, Chiropractic. Cervical Collar Posture Neck Stretcher Brace Support (White—1st Generation)," Retrieved from the Internet May 6, 2022 https://www.amazon.com/PUREPLAN-Shoulder-Traction-Chiropractic-Stretcher/dp/B099CPCBS3/ref=asc_df_B099CPCBS3/?tag=hyprod-20&linkCode=df0&hvadid=532600134452&hvpos=&hvnetw=g&hvrand=76712344603371128&hvpone=&hvptwo=&hvqmt=&hvdev=c&hvdvcmdl=&hvlocint=&hvlocphy=1014895&hvtargid=pla-1409596001705&psc=1.

Google Search, "neck halo shoulder brace," Retrieved from the Internet May 6, 2022 https://www.google.com/imgres?mgurl=https%3A%2F%2Fhealthmanagement.org%2Fuploads%2Fproduct_image%2Fmp_img_72961.ipg&imgrefurl=https%3A%2F%2Fhealthmanagement.org%2Fproducts%2Fview%2Fcervico-thoracic-cto-support-corset-halo-type-resolve-r-ossur&tbnid=tQXcFZGwjP51XM&vet=12ahUKEwjc4qqDmrj3AhXTZTUKHREGBzUQMygKegUIARDXAg.i&docid=-.

International Search Report and Written Opinion received for PCT Patent Application No. PCT/US2017/037257, mailed on Nov 29, 2017, 14 pages.

International Search Report and Written Opinion received for PCT Patent Application No. PCT/US22/72186, mailed on Nov. 9, 2022, 20 pages.

International Search Report and Written Opinion for Int'l Application No. PCT/US2022/072186, Dated: Nov. 9, 2022.

Cervino, A. et al., "Wavefront Analyzers Induce Instrument Myopia," Journal of Refractive Surger, 22(2): 795-803 (2006) (Abstract Only).

Marks, R. et al., "Adjustable adaptive compact fluidic phoropter with no mechanical translation of lenses," Opt. Lett, 35 (5): 739-741 (2010).

Thibos, L.N., et al., "Accuracy and precision of objective refraction from wavefront aberrations," Journal of Vision, 4: 329-351 (2004).

Pureplan Neck Shoulder Relaxer Traction Device for TMJ Pain Relief, Retrieved from internet at: https://www.amazon.com/PUREPLAN-Shoulder_Traction_Chiropractic . . . , Retrieved from internet on: May 6, 2022 (5 pages).

Health Management and Leadership Portal, Cervico-thoracic, Retrieved from internet at: https://healthmanagement.org/uploads/product_image/mp_img_ . . . , Retrieved from internet on: May 6, 2022 (1 page).

WAVEFRONT ABERROMETER
APPARATUS
500

REPORTING SCREEN
554

TRIGGER SWITCH
397

MODULAR INTERFACE
592

LENSOMETER ATTACHMENT
591

CALIBRATION RESERVOIR
595

EYEGLASSES
598

HOUSING
502

GRIP FEATURES
503

PORT
505

EYECUP
504

SLIDING TRACK AND MECHANISM
596

LENS HOLDING BAYS
594

ARTIFICIAL
EYES
599

(TOP VIEW)

(SIDE VIEW)

(SIDE VIEW)

517

519

CALIBRATION CRADLE 517

ARTIFICIAL EYE ASSEMBLY 519

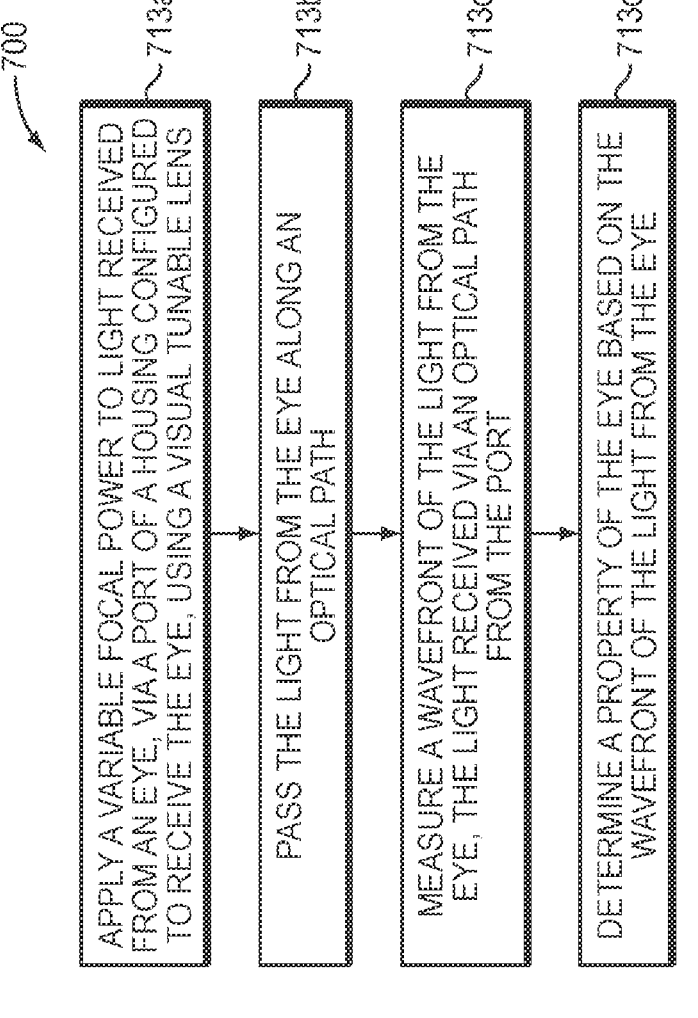

700

APPLY A VARIABLE FOCAL POWER TO LIGHT RECEIVED FROM AN EYE, VIA A PORT OF A HOUSING CONFIGURED TO RECEIVE THE EYE, USING A VISUAL TUNABLE LENS — 713a

PASS THE LIGHT FROM THE EYE ALONG AN OPTICAL PATH — 713b

MEASURE A WAVEFRONT OF THE LIGHT FROM THE EYE, THE LIGHT RECEIVED VIA AN OPTICAL PATH FROM THE PORT — 713c

DETERMINE A PROPERTY OF THE EYE BASED ON THE WAVEFRONT OF THE LIGHT FROM THE EYE — 713d

FIG. 7 (PRIOR ART)

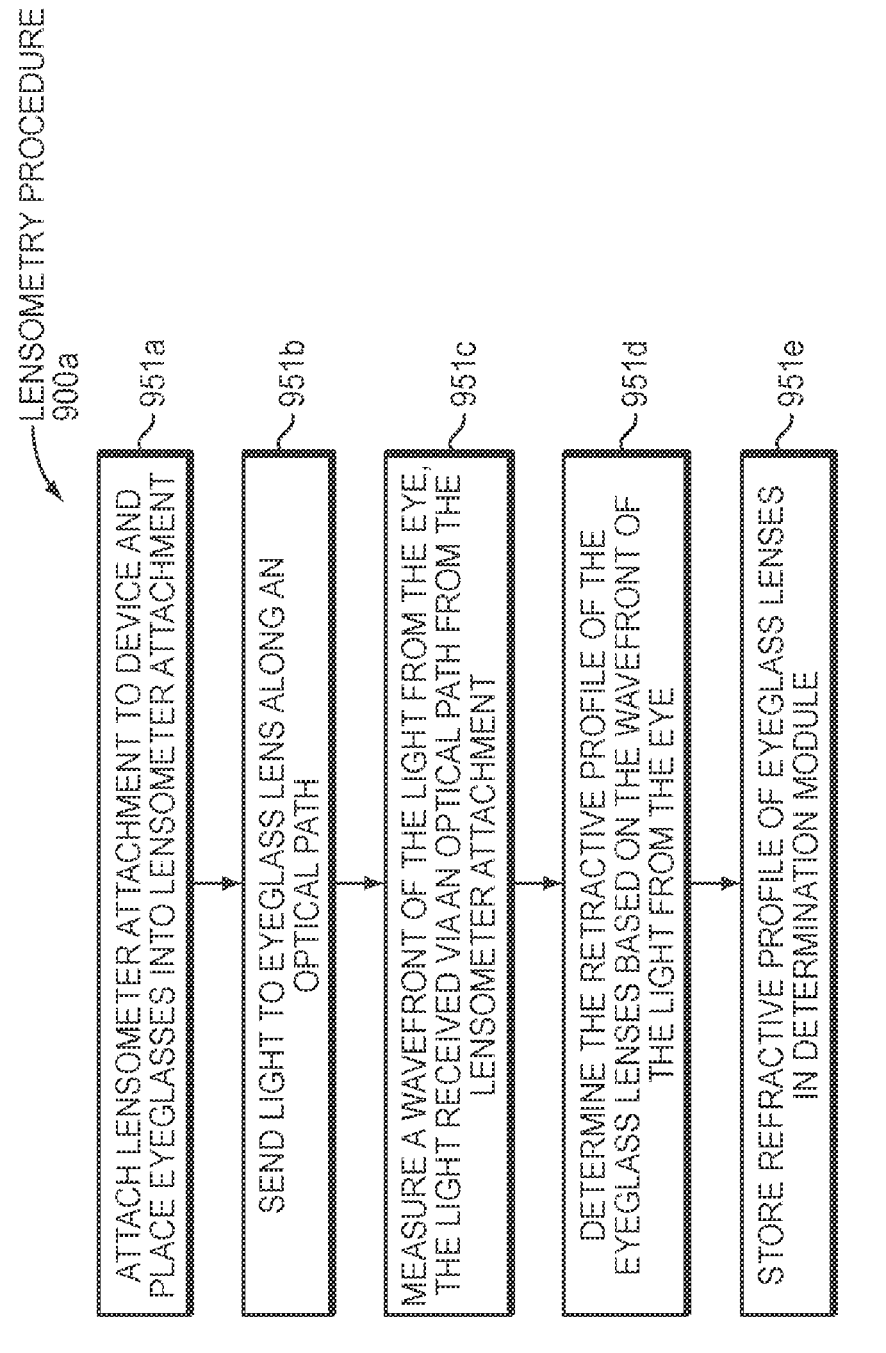

LENSOMETRY PROCEDURE
900a

951a ATTACH LENSOMETER ATTACHMENT TO DEVICE AND PLACE EYEGLASSES INTO LENSOMETER ATTACHMENT

951b SEND LIGHT TO EYEGLASS LENS ALONG AN OPTICAL PATH

951c MEASURE A WAVEFRONT OF THE LIGHT FROM THE EYE, THE LIGHT RECEIVED VIA AN OPTICAL PATH FROM THE LENSOMETER ATTACHMENT

951d DETERMINE THE RETRACTIVE PROFILE OF THE EYEGLASS LENSES BASED ON THE WAVEFRONT OF THE LIGHT FROM THE EYE

951e STORE REFRACTIVE PROFILE OF EYEGLASS LENSES IN DETERMINATION MODULE

FIG. 9A (PRIOR ART)

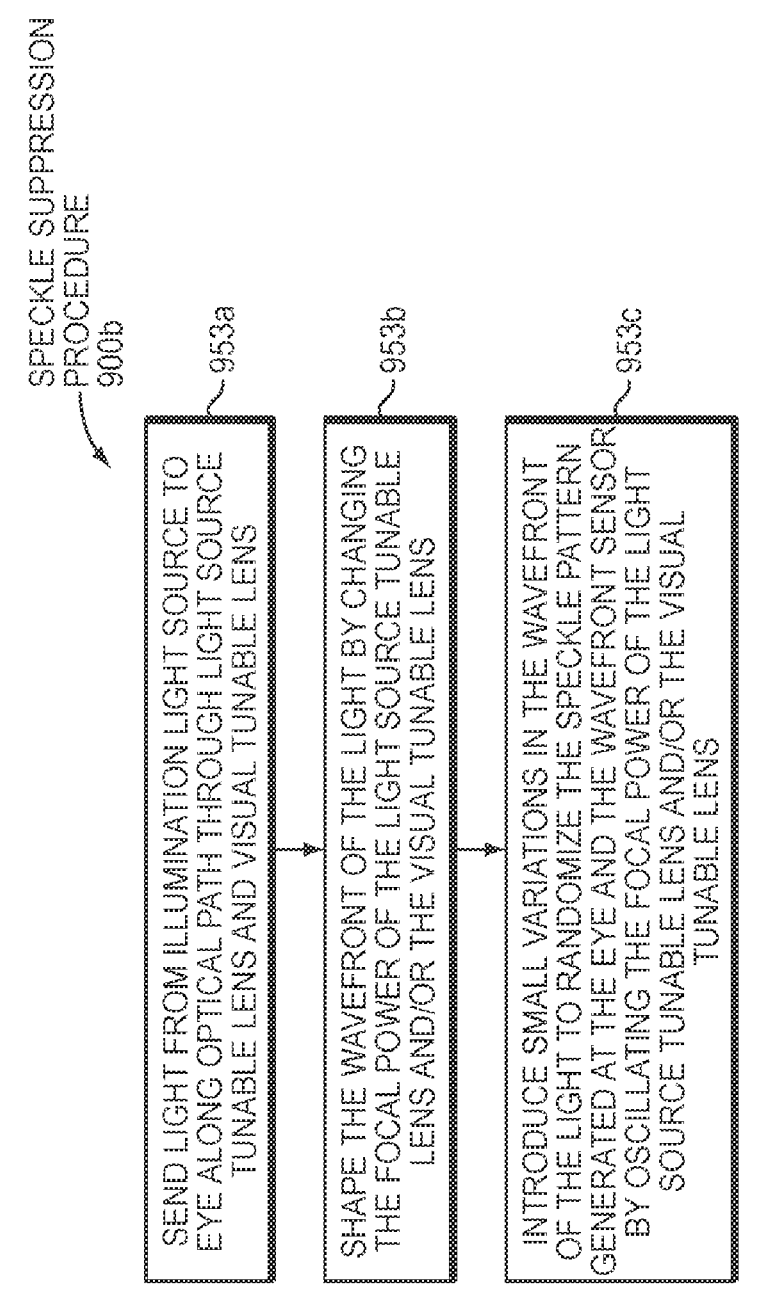

SPECKLE SUPPRESSION
PROCEDURE
900b

953a

SEND LIGHT FROM ILLUMINATION LIGHT SOURCE TO EYE ALONG OPTICAL PATH THROUGH LIGHT SOURCE TUNABLE LENS AND VISUAL TUNABLE LENS

953b

SHAPE THE WAVEFRONT OF THE LIGHT BY CHANGING THE FOCAL POWER OF THE LIGHT SOURCE TUNABLE LENS AND/OR THE VISUAL TUNABLE LENS

953c

INTRODUCE SMALL VARIATIONS IN THE WAVEFRONT OF THE LIGHT TO RANDOMIZE THE SPECKLE PATTERN GENERATED AT THE EYE AND THE WAVEFRONT SENSOR BY OSCILLATING THE FOCAL POWER OF THE LIGHT SOURCE TUNABLE LENS AND/OR THE VISUAL TUNABLE LENS

FIG. 9B (PRIOR ART)

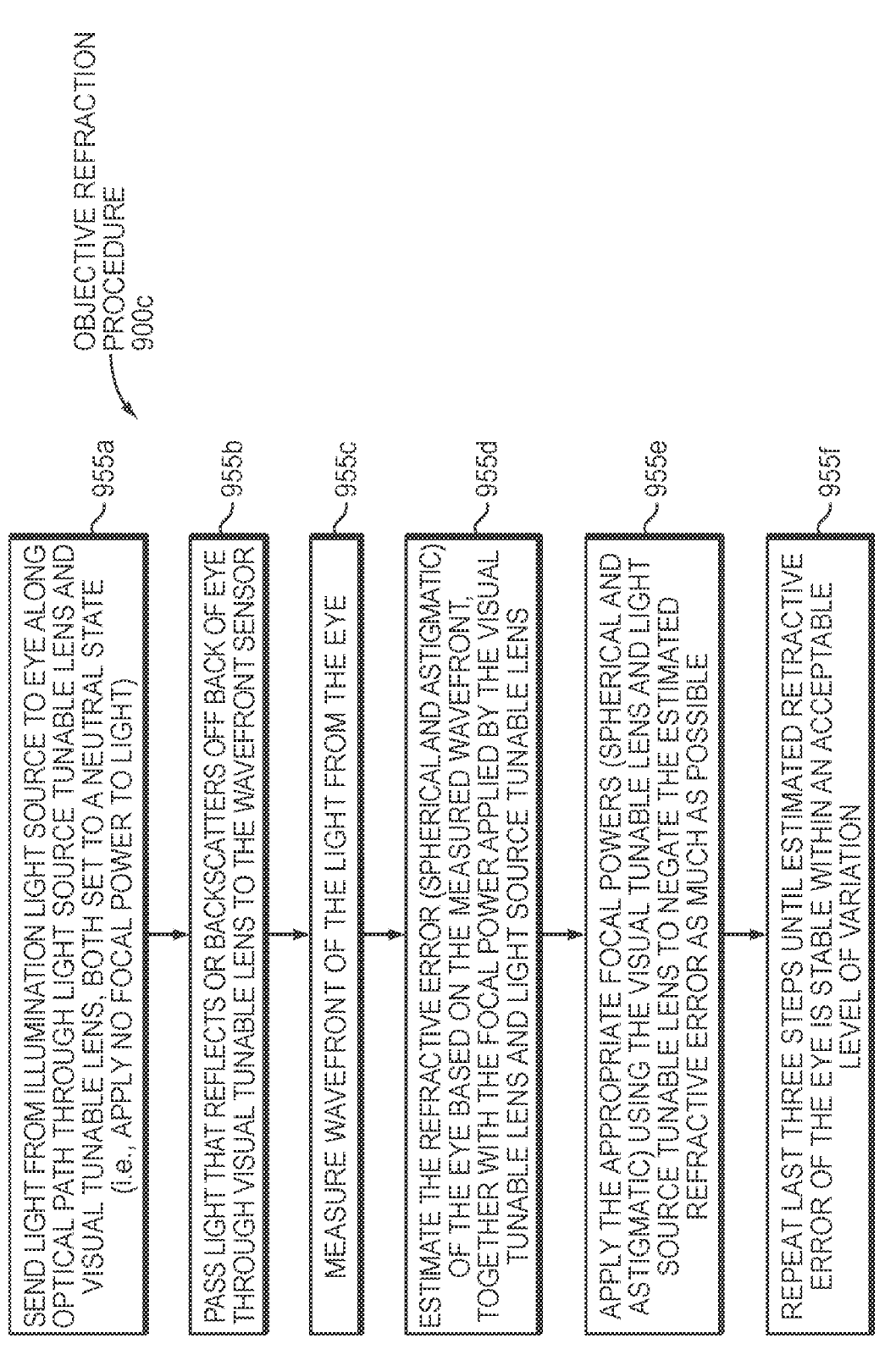

OBJECTIVE REFRACTION
PROCEDURE
900c

955a SEND LIGHT FROM ILLUMINATION LIGHT SOURCE TO EYE ALONG OPTICAL PATH THROUGH LIGHT SOURCE TUNABLE LENS AND VISUAL TUNABLE LENS, BOTH SET TO A NEUTRAL STATE (i.e., APPLY NO FOCAL POWER TO LIGHT)

955b PASS LIGHT THAT REFLECTS OR BACKSCATTERS OFF BACK OF EYE THROUGH VISUAL TUNABLE LENS TO THE WAVEFRONT SENSOR

955c MEASURE WAVEFRONT OF THE LIGHT FROM THE EYE

955d ESTIMATE THE REFRACTIVE ERROR (SPHERICAL AND ASTIGMATIC) OF THE EYE BASED ON THE MEASURED WAVEFRONT, TOGETHER WITH THE FOCAL POWER APPLIED BY THE VISUAL TUNABLE LENS AND LIGHT SOURCE TUNABLE LENS

955e APPLY THE APPROPRIATE FOCAL POWERS (SPHERICAL AND ASTIGMATIC) USING THE VISUAL TUNABLE LENS AND LIGHT SOURCE TUNABLE LENS TO NEGATE THE ESTIMATED REFRACTIVE ERROR AS MUCH AS POSSIBLE

955f REPEAT LAST THREE STEPS UNTIL ESTIMATED REFRACTIVE ERROR OF THE EYE IS STABLE WITHIN AN ACCEPTABLE LEVEL OF VARIATION

FIG. 9C (PRIOR ART)

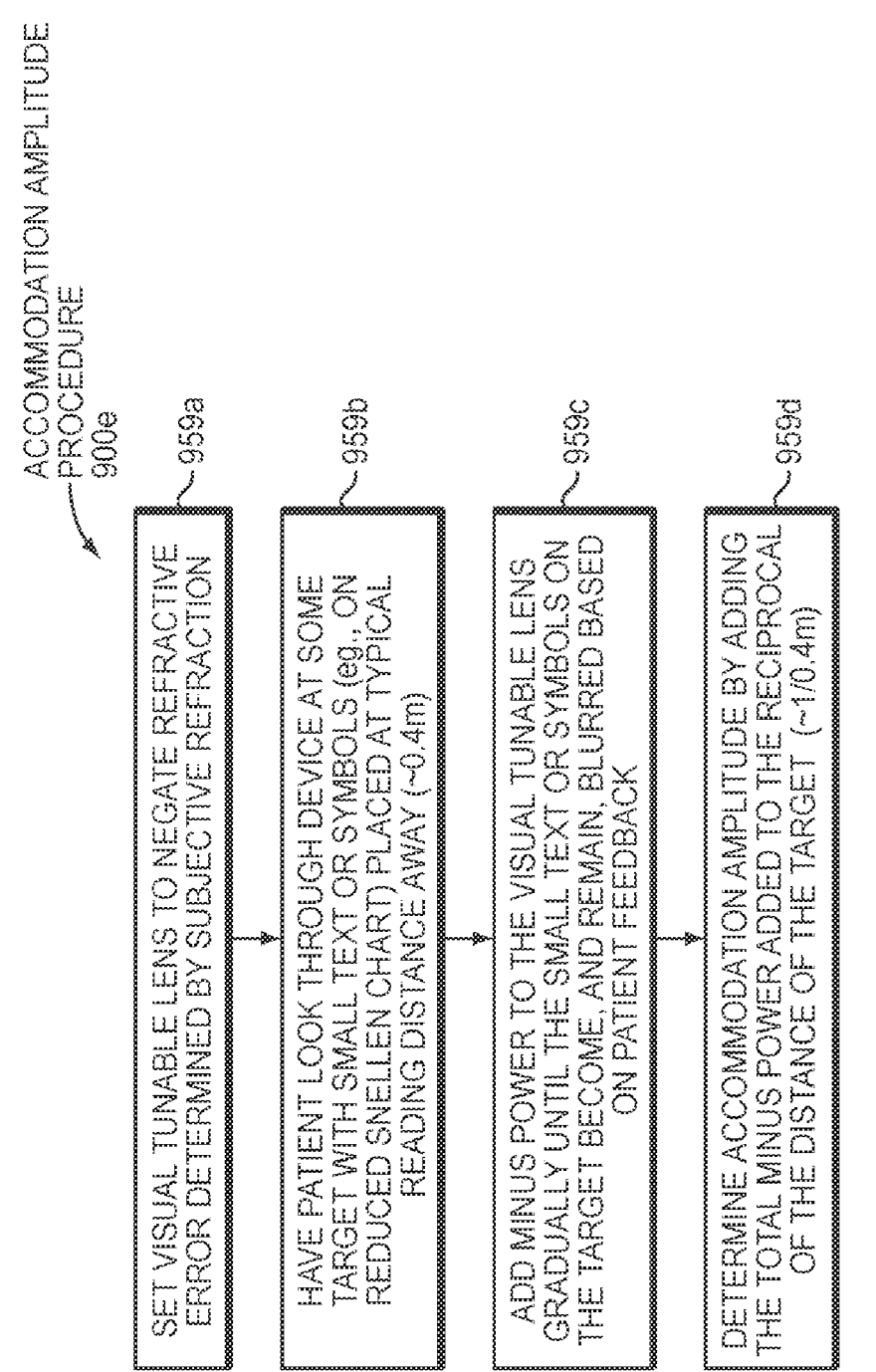

ACCOMMODATION AMPLITUDE
PROCEDURE
900e

959a
SET VISUAL TUNABLE LENS TO NEGATE REFRACTIVE ERROR DETERMINED BY SUBJECTIVE REFRACTION

959b
HAVE PATIENT LOOK THROUGH DEVICE AT SOME TARGET WITH SMALL TEXT OR SYMBOLS (eg., ON REDUCED SNELLEN CHART) PLACED AT TYPICAL READING DISTANCE AWAY (~0.4m)

959c
ADD MINUS POWER TO THE VISUAL TUNABLE LENS GRADUALLY UNTIL THE SMALL TEXT OR SYMBOLS ON THE TARGET BECOME, AND REMAIN, BLURRED BASED ON PATIENT FEEDBACK

959d
DETERMINE ACCOMMODATION AMPLITUDE BY ADDING THE TOTAL MINUS POWER ADDED TO THE RECIPROCAL OF THE DISTANCE OF THE TARGET (~1/0.4m)

FIG. 9E (PRIOR ART)

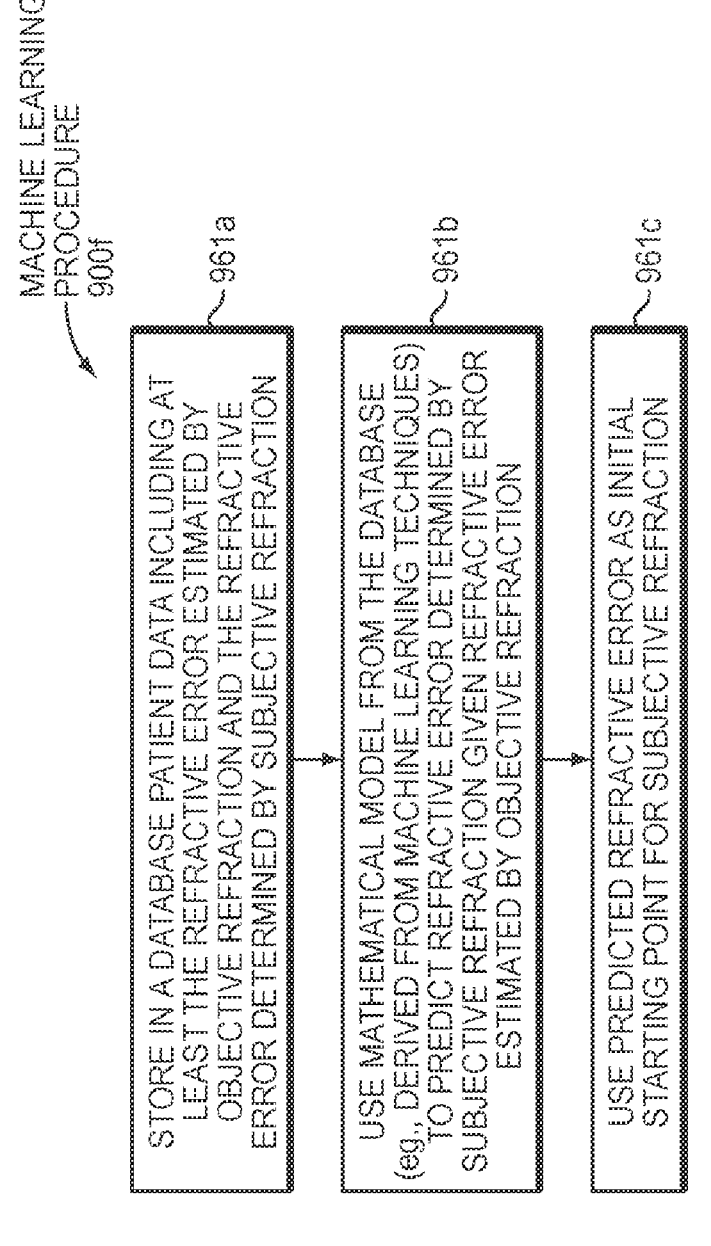

MACHINE LEARNING
PROCEDURE
900f

961a

STORE IN A DATABASE PATIENT DATA INCLUDING AT LEAST THE REFRACTIVE ERROR ESTIMATED BY OBJECTIVE REFRACTION AND THE REFRACTIVE ERROR DETERMINED BY SUBJECTIVE REFRACTION

961b

USE MATHEMATICAL MODEL FROM THE DATABASE (eg., DERIVED FROM MACHINE LEARNING TECHNIQUES) TO PREDICT REFRACTIVE ERROR DETERMINED BY SUBJECTIVE REFRACTION GIVEN REFRACTIVE ERROR ESTIMATED BY OBJECTIVE REFRACTION

961c

USE PREDICTED REFRACTIVE ERROR AS INITIAL STARTING POINT FOR SUBJECTIVE REFRACTION

FIG. 9F (PRIOR ART)

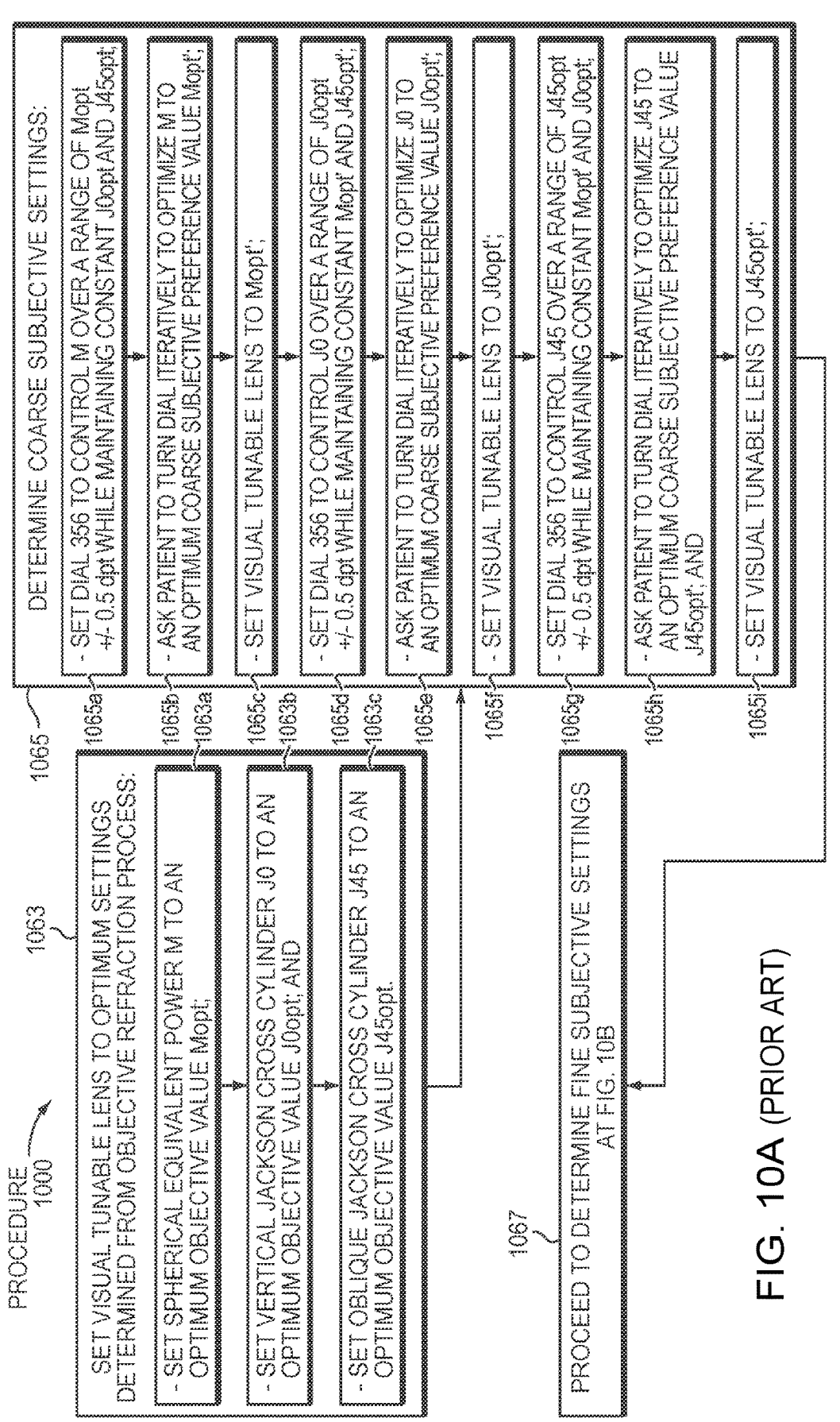

PROCEDURE 1000

1063

SET VISUAL TUNABLE LENS TO OPTIMUM SETTINGS DETERMINED FROM OBJECTIVE REFRACTION PROCESS:

- SET SPHERICAL EQUIVALENT POWER M TO AN OPTIMUM OBJECTIVE VALUE Mopt;

1063a

- SET VERTICAL JACKSON CROSS CYLINDER J0 TO AN OPTIMUM OBJECTIVE VALUE J0opt; AND 1063b

- SET OBLIQUE JACKSON CROSS CYLINDER J45 TO AN OPTIMUM OBJECTIVE VALUE J45opt.

1063c

1065

DETERMINE COARSE SUBJECTIVE SETTINGS:

1065a
- SET DIAL 356 TO CONTROL M OVER A RANGE OF Mopt +/- 0.5 dpt WHILE MAINTAINING CONSTANT J0opt AND J45opt;

1065b
- ASK PATIENT TO TURN DIAL ITERATIVELY TO OPTIMIZE M TO AN OPTIMUM COARSE SUBJECTIVE PREFERENCE VALUE Mopt';

1065c
- SET VISUAL TUNABLE LENS TO Mopt';

1065d
- SET DIAL 356 TO CONTROL J0 OVER A RANGE OF J0opt +/- 0.5 dpt WHILE MAINTAINING CONSTANT Mopt' AND J45opt;

1065e
- ASK PATIENT TO TURN DIAL ITERATIVELY TO OPTIMIZE J0 TO AN OPTIMUM COARSE SUBJECTIVE PREFERENCE VALUE J0opt';

1065f
- SET VISUAL TUNABLE LENS TO J0opt';

1065g
- SET DIAL 356 TO CONTROL J45 OVER A RANGE OF J45opt +/- 0.5 dpt WHILE MAINTAINING CONSTANT Mopt' AND J0opt;

1065h
- ASK PATIENT TO TURN DIAL ITERATIVELY TO OPTIMIZE J45 TO AN OPTIMUM COARSE SUBJECTIVE PREFERENCE VALUE J45opt'; AND 1065i
- SET VISUAL TUNABLE LENS TO J45opt';

1067

PROCEED TO DETERMINE FINE SUBJECTIVE SETTINGS AT FIG. 10B

FIG. 10A (PRIOR ART)

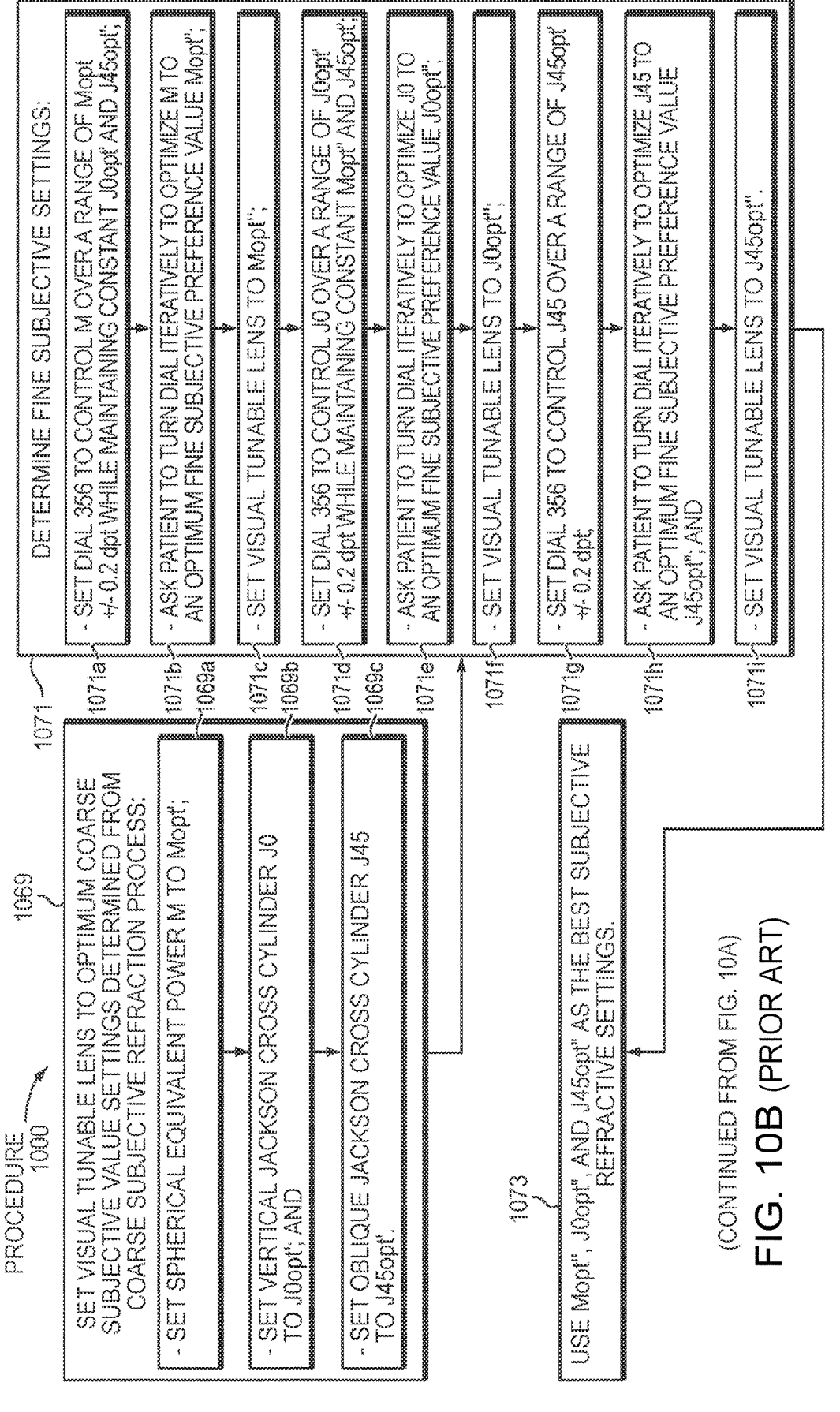

PROCEDURE
1000

SET VISUAL TUNABLE LENS TO OPTIMUM COARSE SUBJECTIVE VALUE SETTINGS DETERMINED FROM COARSE SUBJECTIVE REFRACTION PROCESS:

1069

- SET SPHERICAL EQUIVALENT POWER M TO Mopt';

- SET VERTICAL JACKSON CROSS CYLINDER J0 TO J0opt'; AND

- SET OBLIQUE JACKSON CROSS CYLINDER J45 TO J45opt'.

DETERMINE FINE SUBJECTIVE SETTINGS:

1071

- SET DIAL 356 TO CONTROL M OVER A RANGE OF Mopt' +/- 0.2 dpt WHILE MAINTAINING CONSTANT J0opt' AND J45opt';    1071a

- ASK PATIENT TO TURN DIAL ITERATIVELY TO OPTIMIZE M TO AN OPTIMUM FINE SUBJECTIVE PREFERENCE VALUE Mopt";    1071b
1069a

- SET VISUAL TUNABLE LENS TO Mopt";    1071c
1069b

- SET DIAL 356 TO CONTROL J0 OVER A RANGE OF J0opt' +/- 0.2 dpt WHILE MAINTAINING CONSTANT Mopt" AND J45opt';    1071d
1069c

- ASK PATIENT TO TURN DIAL ITERATIVELY TO OPTIMIZE J0 TO AN OPTIMUM FINE SUBJECTIVE PREFERENCE VALUE J0opt";    1071e

- SET VISUAL TUNABLE LENS TO J0opt";    1071f

- SET DIAL 356 TO CONTROL J45 OVER A RANGE OF J45opt' +/- 0.2 dpt;    1071g

- ASK PATIENT TO TURN DIAL ITERATIVELY TO OPTIMIZE J45 TO AN OPTIMUM FINE SUBJECTIVE PREFERENCE VALUE J45opt"; AND    1071h

- SET VISUAL TUNABLE LENS TO J45opt".    1071i

USE Mopt", J0opt", AND J45opt" AS THE BEST SUBJECTIVE REFRACTIVE SETTINGS.

1073

(CONTINUED FROM FIG. 10A)

FIG. 10B (PRIOR ART)

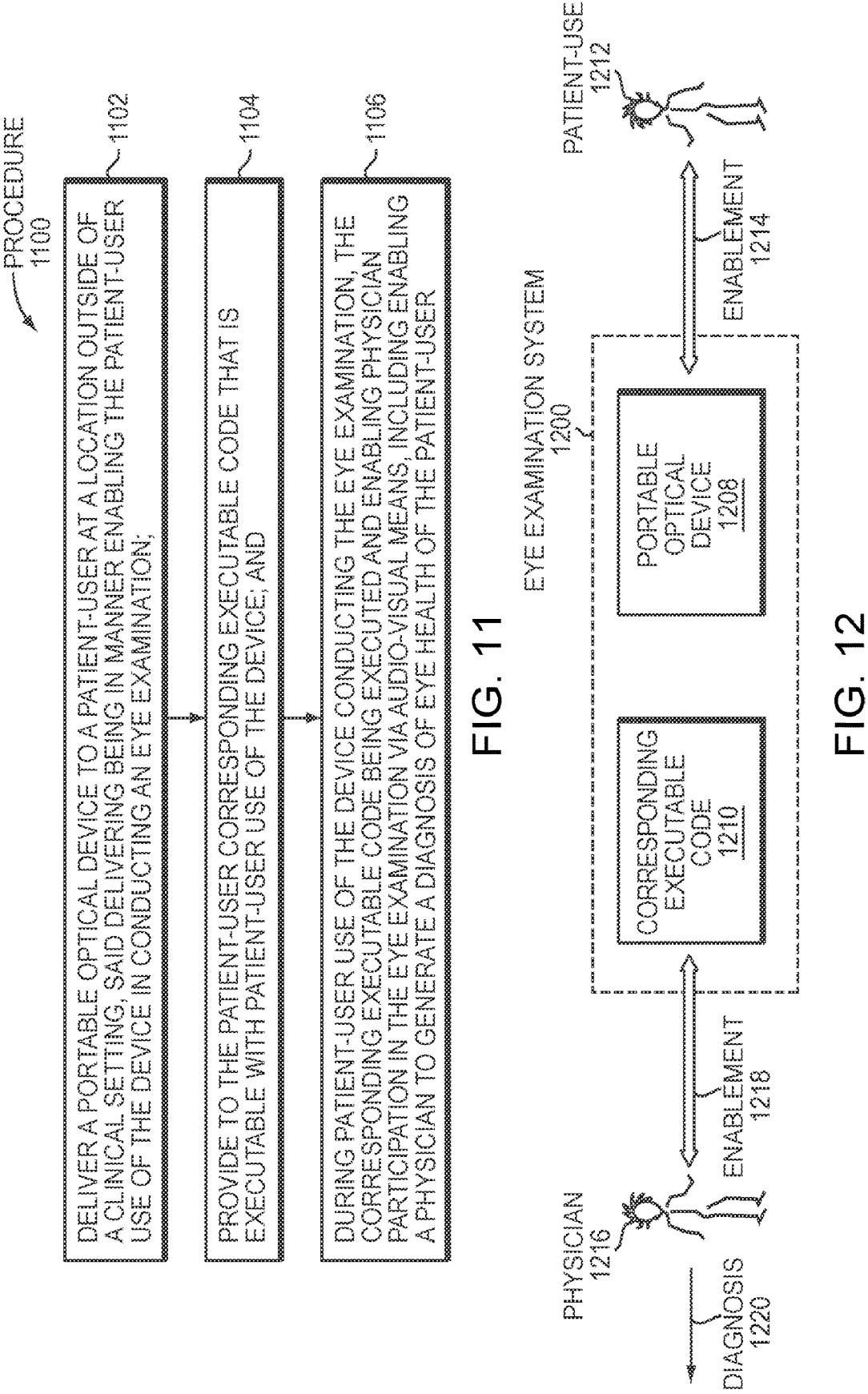

EYE EXAMINATION PROCEDURE 1100

DELIVER A PORTABLE OPTICAL DEVICE TO A PATIENT-USER AT A LOCATION OUTSIDE OF A CLINICAL SETTING, SAID DELIVERING BEING IN MANNER ENABLING THE PATIENT-USER USE OF THE DEVICE IN CONDUCTING AN EYE EXAMINATION; 1102

PROVIDE TO THE PATIENT-USER CORRESPONDING EXECUTABLE CODE THAT IS EXECUTABLE WITH PATIENT-USER USE OF THE DEVICE; AND 1104

DURING PATIENT-USER USE OF THE DEVICE CONDUCTING THE EYE EXAMINATION, THE CORRESPONDING EXECUTABLE CODE BEING EXECUTED AND ENABLING PHYSICIAN PARTICIPATION IN THE EYE EXAMINATION VIA AUDIO-VISUAL MEANS, INCLUDING ENABLING A PHYSICIAN TO GENERATE A DIAGNOSIS OF EYE HEALTH OF THE PATIENT-USER 1106

FIG. 11

PATIENT-USER 1212

EYE EXAMINATION SYSTEM 1200

ENABLEMENT 1214

PORTABLE OPTICAL DEVICE 1208

CORRESPONDING EXECUTABLE CODE 1210

ENABLEMENT 1218

PHYSICIAN 1216

DIAGNOSIS 1220

FIG. 12

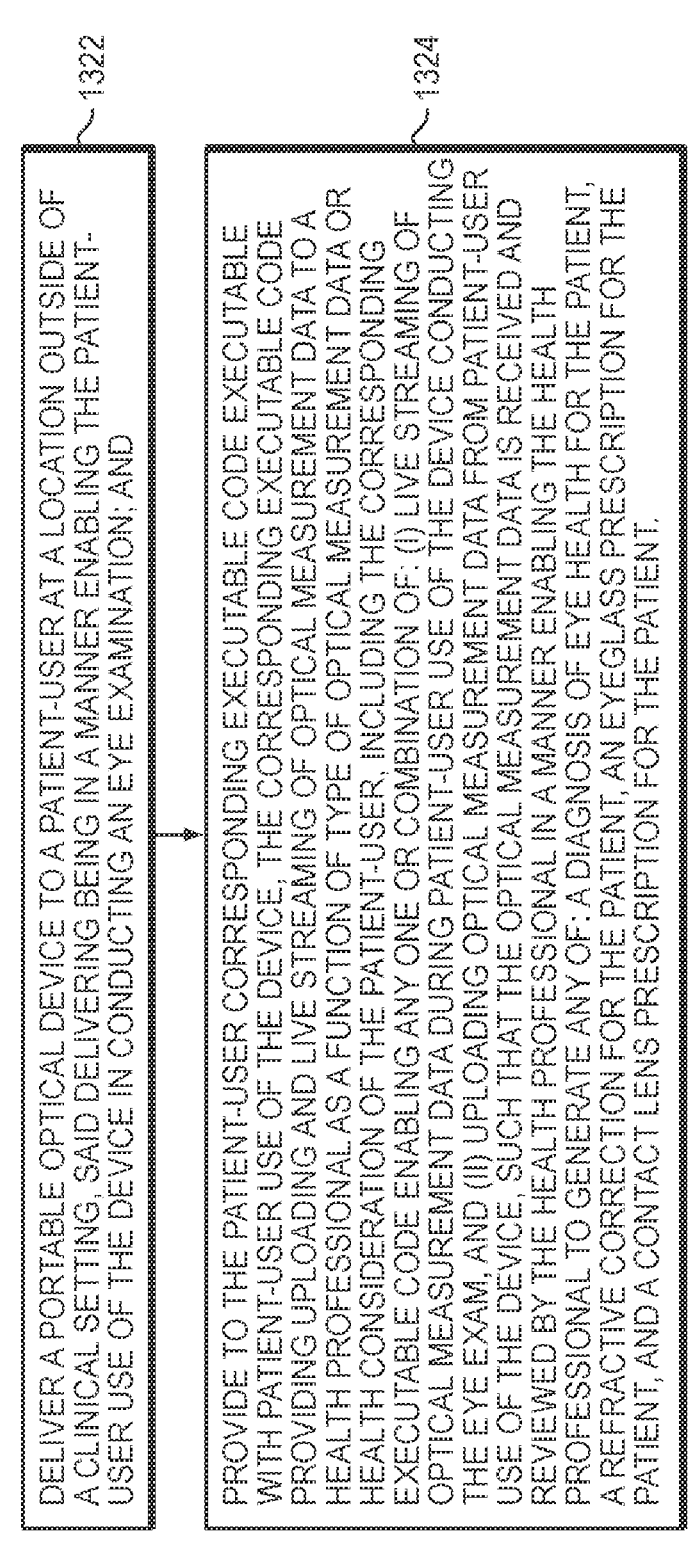

EYE EXAMINATION PROCEDURE 1300

1322

DELIVER A PORTABLE OPTICAL DEVICE TO A PATIENT-USER AT A LOCATION OUTSIDE OF A CLINICAL SETTING, SAID DELIVERING BEING IN A MANNER ENABLING THE PATIENT-USER USE OF THE DEVICE IN CONDUCTING AN EYE EXAMINATION; AND

1324

PROVIDE TO THE PATIENT-USER CORRESPONDING EXECUTABLE CODE EXECUTABLE WITH PATIENT-USER USE OF THE DEVICE, THE CORRESPONDING EXECUTABLE CODE PROVIDING UPLOADING AND LIVE STREAMING OF OPTICAL MEASUREMENT DATA TO A HEALTH PROFESSIONAL AS A FUNCTION OF TYPE OF OPTICAL MEASUREMENT DATA OR HEALTH CONSIDERATION OF THE PATIENT-USER, INCLUDING THE CORRESPONDING EXECUTABLE CODE ENABLING ANY ONE OR COMBINATION OF: (I) LIVE STREAMING OF OPTICAL MEASUREMENT DATA DURING PATIENT-USER USE OF THE DEVICE CONDUCTING THE EYE EXAM, AND (II) UPLOADING OPTICAL MEASUREMENT DATA FROM PATIENT-USER USE OF THE DEVICE, SUCH THAT THE OPTICAL MEASUREMENT DATA IS RECEIVED AND REVIEWED BY THE HEALTH PROFESSIONAL IN A MANNER ENABLING THE HEALTH PROFESSIONAL TO GENERATE ANY OF: A DIAGNOSIS OF EYE HEALTH FOR THE PATIENT, A REFRACTIVE CORRECTION FOR THE PATIENT, AN EYEGLASS PRESCRIPTION FOR THE PATIENT, AND A CONTACT LENS PRESCRIPTION FOR THE PATIENT.

FIG. 13

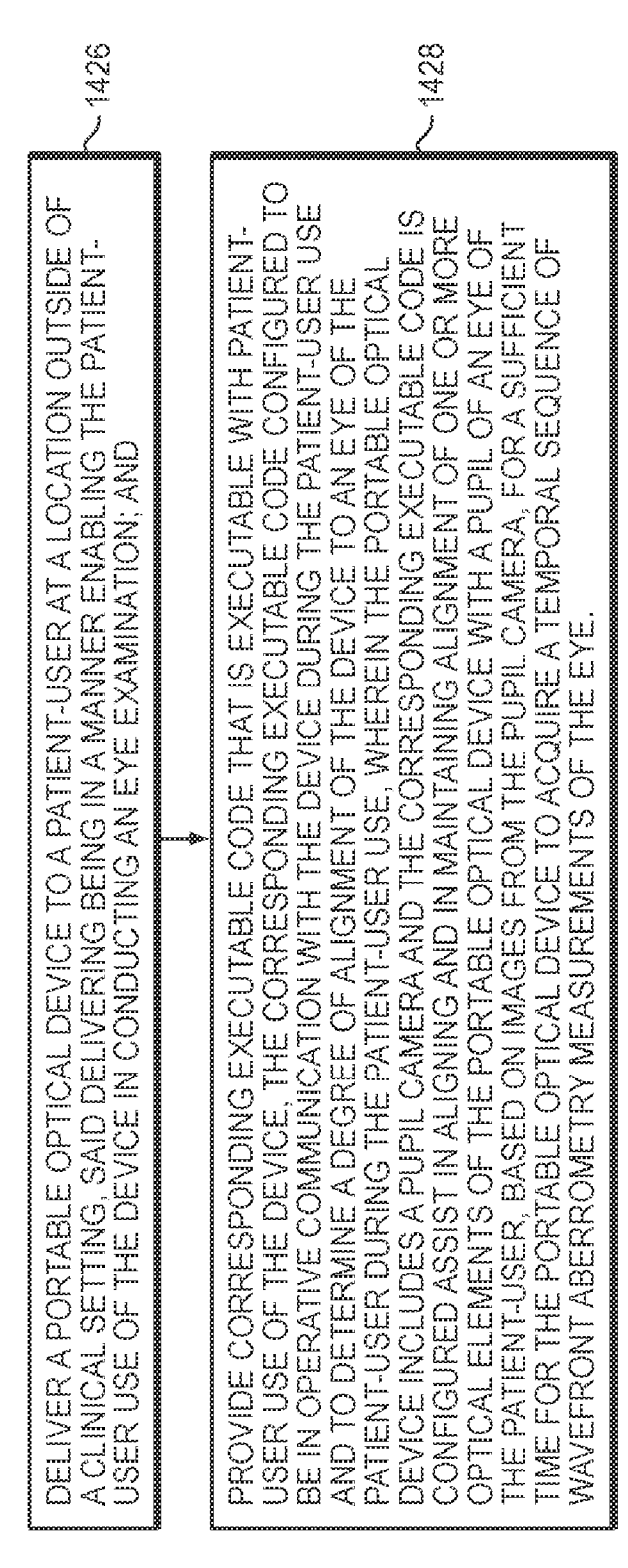

EYE EXAMINATION PROCEDURE 1400

1426

DELIVER A PORTABLE OPTICAL DEVICE TO A PATIENT-USER AT A LOCATION OUTSIDE OF A CLINICAL SETTING, SAID DELIVERING BEING IN A MANNER ENABLING THE PATIENT-USER USE OF THE DEVICE IN CONDUCTING AN EYE EXAMINATION; AND

1428

PROVIDE CORRESPONDING EXECUTABLE CODE THAT IS EXECUTABLE WITH PATIENT-USER USE OF THE DEVICE, THE CORRESPONDING EXECUTABLE CODE CONFIGURED TO BE IN OPERATIVE COMMUNICATION WITH THE DEVICE DURING THE PATIENT-USER USE AND TO DETERMINE A DEGREE OF ALIGNMENT OF THE DEVICE TO AN EYE OF THE PATIENT-USER DURING THE PATIENT-USER USE, WHEREIN THE PORTABLE OPTICAL DEVICE INCLUDES A PUPIL CAMERA AND THE CORRESPONDING EXECUTABLE CODE IS CONFIGURED ASSIST IN ALIGNING AND IN MAINTAINING ALIGNMENT OF ONE OR MORE OPTICAL ELEMENTS OF THE PORTABLE OPTICAL DEVICE WITH A PUPIL OF AN EYE OF THE PATIENT-USER, BASED ON IMAGES FROM THE PUPIL CAMERA, FOR A SUFFICIENT TIME FOR THE PORTABLE OPTICAL DEVICE TO ACQUIRE A TEMPORAL SEQUENCE OF WAVEFRONT ABERROMETRY MEASUREMENTS OF THE EYE.

FIG. 14

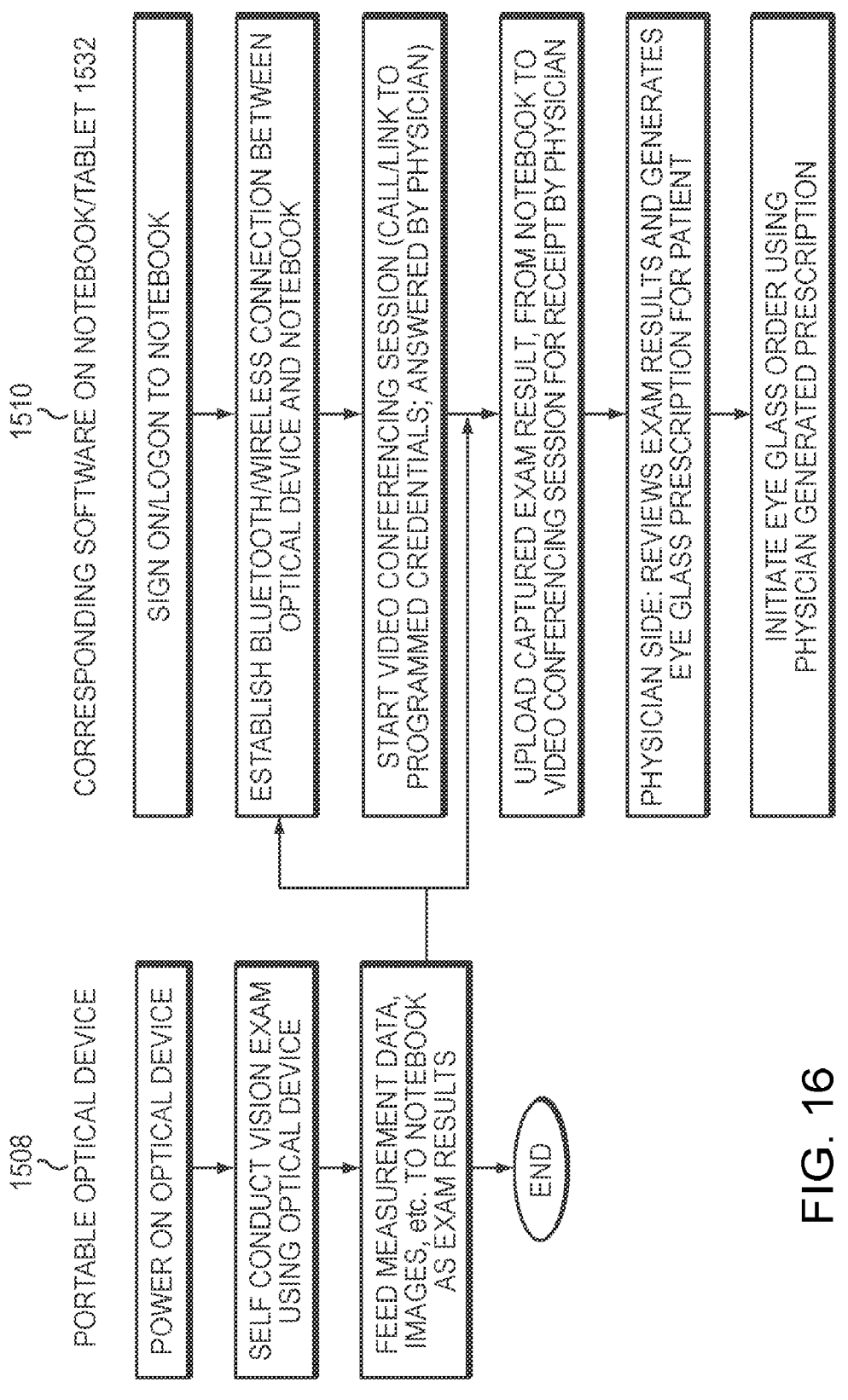

1510

CORRESPONDING SOFTWARE ON NOTEBOOK/TABLET 1532

SIGN ON/LOGON TO NOTEBOOK

ESTABLISH BLUETOOTH/WIRELESS CONNECTION BETWEEN OPTICAL DEVICE AND NOTEBOOK

START VIDEO CONFERENCING SESSION (CALL/LINK TO PROGRAMMED CREDENTIALS; ANSWERED BY PHYSICIAN)

UPLOAD CAPTURED EXAM RESULT, FROM NOTEBOOK TO VIDEO CONFERENCING SESSION FOR RECEIPT BY PHYSICIAN

PHYSICIAN SIDE: REVIEWS EXAM RESULTS AND GENERATES EYE GLASS PRESCRIPTION FOR PATIENT

INITIATE EYE GLASS ORDER USING PHYSICIAN GENERATED PRESCRIPTION

1508

PORTABLE OPTICAL DEVICE

POWER ON OPTICAL DEVICE

SELF CONDUCT VISION EXAM USING OPTICAL DEVICE

FEED MEASUREMENT DATA, IMAGES, etc. TO NOTEBOOK AS EXAM RESULTS

END

FIG. 16

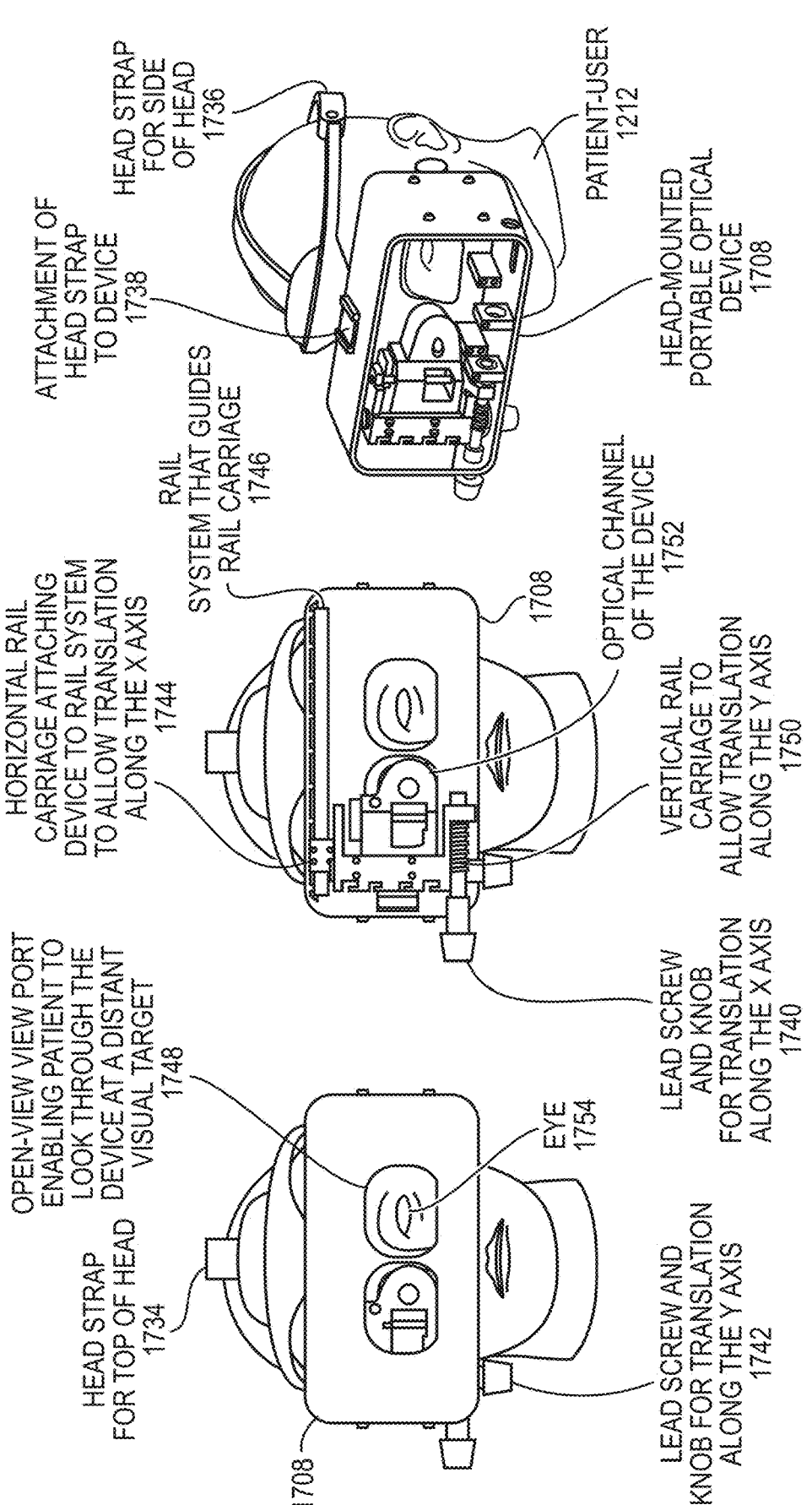

ATTACHMENT OF HEAD STRAP TO DEVICE 1738

HEAD STRAP FOR SIDE OF HEAD 1736

PATIENT-USER 1212

HEAD-MOUNTED PORTABLE OPTICAL DEVICE 1708

RAIL SYSTEM THAT GUIDES RAIL CARRIAGE 1746

HORIZONTAL RAIL CARRIAGE ATTACHING DEVICE TO RAIL SYSTEM TO ALLOW TRANSLATION ALONG THE X AXIS 1744

1708

OPTICAL CHANNEL OF THE DEVICE 1752

VERTICAL RAIL CARRIAGE TO ALLOW TRANSLATION ALONG THE Y AXIS 1750

LEAD SCREW AND KNOB FOR TRANSLATION ALONG THE X AXIS 1740

OPEN-VIEW VIEW PORT ENABLING PATIENT TO LOOK THROUGH THE DEVICE AT A DISTANT VISUAL TARGET 1748

HEAD STRAP FOR TOP OF HEAD 1734

EYE 1754

LEAD SCREW AND KNOB FOR TRANSLATION ALONG THE Y AXIS 1742

HEAD-MOUNTED PORTABLE OPTICAL DEVICE 1808

1740

1742

SUPPORT STRUCTURE TO HOLD DEVICE IN FRONT OF PATIENT'S FACE 1858

SUPPORT STRUCTURE TO STABILIZE AND SUPPORT WEIGHT OF THE DEVICE ON THE PATIENT'S SHOULDERS 1860

1212

SUPPORT STRUCTURE TO STABILIZE THE DEVICE AND THE MOUNTING APPARATUS AGAINST THE PATIENT'S BACK AND NECK 1856

SHOULDER 1813

STAND-MOUNTED PORTABLE OPTICAL DEVICE 1908

FRONT OF THE DEVICE WHICH IS OPEN VIEW SO THAT PATIENT CAN LOOK THROUGH IT 1966

CLAMP TO SECURE DEVICE TO TRIPOD, MONOPOD, OR STAND 1968

EYECUP WHERE PATIENT WILL REST THEIR FACE AGAINST TO LOOK THROUGH THE OPEN-VIEW DEVICE 1964

TRIPOD, MONOPOD, OR OTHER STAND 1962

KERATOMETRY IMAGES AT A CLOSER DISTANCE (LEFT), MEDIUM DISTANCE (MIDDLE), AND FURTHER DISTANCE (RIGHT)

CORNEAL REFLECTION OF THE LEDs USED FOR PUPIL IMAGING AND KERATOMETRY 2170

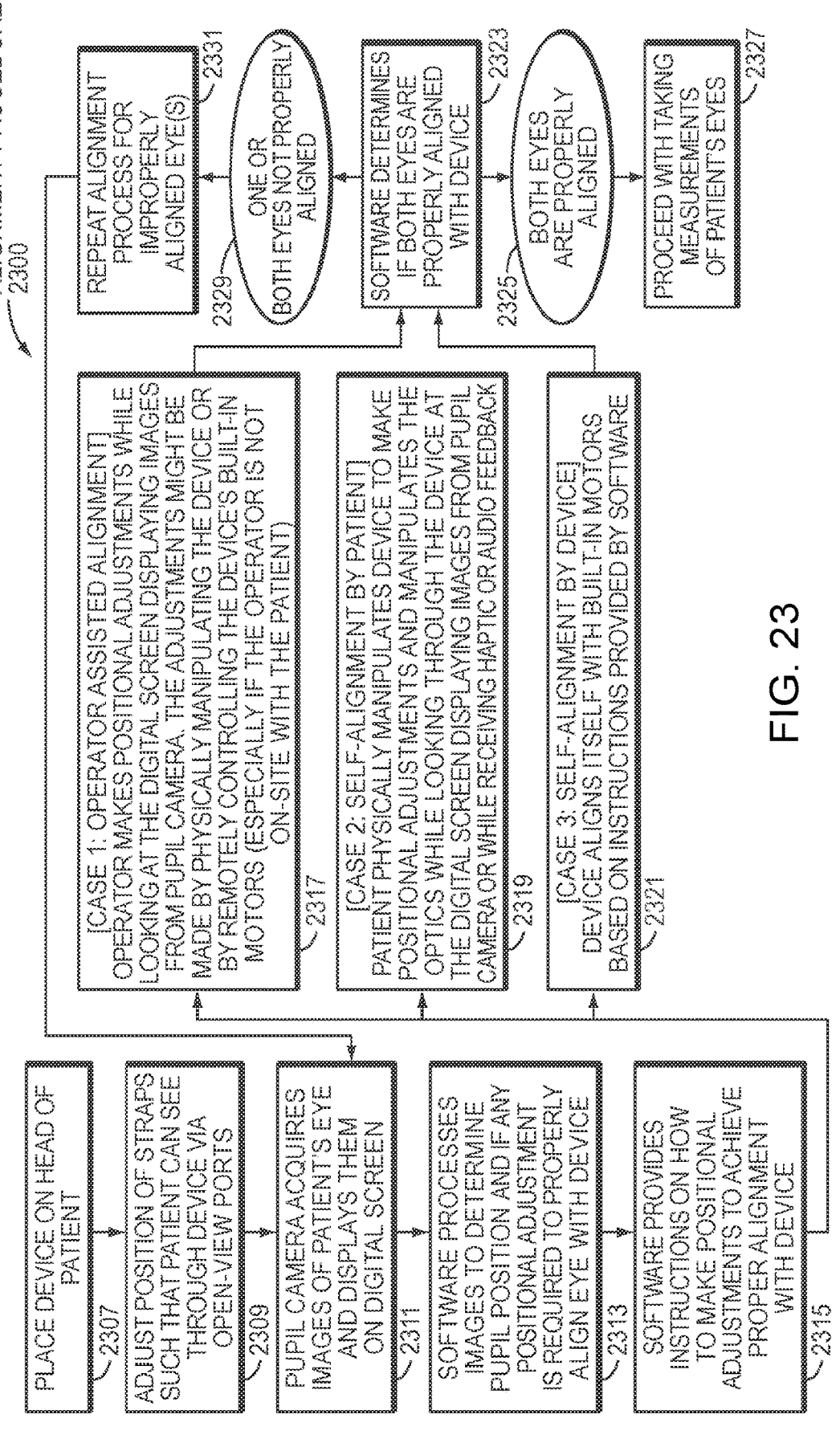

FIG. 23

ALIGNMENT PROCEDURE
2300

PLACE DEVICE ON HEAD OF PATIENT
2307

ADJUST POSITION OF STRAPS SUCH THAT PATIENT CAN SEE THROUGH DEVICE VIA OPEN-VIEW PORTS
2309

PUPIL CAMERA ACQUIRES IMAGES OF PATIENT'S EYE AND DISPLAYS THEM ON DIGITAL SCREEN
2311

SOFTWARE PROCESSES IMAGES TO DETERMINE PUPIL POSITION AND IF ANY POSITIONAL ADJUSTMENT IS REQUIRED TO PROPERLY ALIGN EYE WITH DEVICE
2313

SOFTWARE PROVIDES INSTRUCTIONS ON HOW TO MAKE POSITIONAL ADJUSTMENTS TO ACHIEVE PROPER ALIGNMENT WITH DEVICE
2315

[CASE 1: OPERATOR ASSISTED ALIGNMENT] OPERATOR MAKES POSITIONAL ADJUSTMENTS WHILE LOOKING AT THE DIGITAL SCREEN DISPLAYING IMAGES FROM PUPIL CAMERA. THE ADJUSTMENTS MIGHT BE MADE BY PHYSICALLY MANIPULATING THE DEVICE OR BY REMOTELY CONTROLLING THE DEVICE'S BUILT-IN MOTORS (ESPECIALLY IF THE OPERATOR IS NOT ON-SITE WITH THE PATIENT)
2317

[CASE 2: SELF-ALIGNMENT BY PATIENT] PATIENT PHYSICALLY MANIPULATES DEVICE TO MAKE POSITIONAL ADJUSTMENTS AND MANIPULATES THE OPTICS WHILE LOOKING THROUGH THE DEVICE AT THE DIGITAL SCREEN DISPLAYING IMAGES FROM PUPIL CAMERA OR WHILE RECEIVING HAPTIC OR AUDIO FEEDBACK
2319

[CASE 3: SELF-ALIGNMENT BY DEVICE] DEVICE ALIGNS ITSELF WITH BUILT-IN MOTORS BASED ON INSTRUCTIONS PROVIDED BY SOFTWARE
2321

REPEAT ALIGNMENT PROCESS FOR IMPROPERLY ALIGNED EYE(S)
2331

ONE OR BOTH EYES NOT PROPERLY ALIGNED
2329

SOFTWARE DETERMINES IF BOTH EYES ARE PROPERLY ALIGNED WITH DEVICE
2323

BOTH EYES ARE PROPERLY ALIGNED
2325

PROCEED WITH TAKING MEASUREMENTS OF PATIENT'S EYES
2327

OPEN VIEW CHANNEL
OF THE DEVICE
1748

PORTABLE
OPTICAL DEVICE
2508

PATIENT-USER
1212

OPERATOR
1530

IMAGE 2565 FROM PUPIL CAMERA ON THE DEVICE TO
FACILITATE ALIGNMENT OF THE MEASUREMENT
OPTICS WITH THE PATIENT'S PUPIL

OPEN VIEW CHANNEL 1748 OF THE DEVICE

PATIENT'S FIELD OF VIEW 2669 WHEN LOOKING THROUGH THE OPEN VIEW CHANNEL OF THE DEVICE

PUPIL CAMERA IMAGES (AS SEEN THROUGH THE OPEN-VIEW CHANNEL OF THE DEVICE) ON THE DIGITAL DISPLAY TO FACILITATE SELF-ALIGNMENT OF THE MEASUREMENT OPTICS WITH THE PATIENT'S PUPIL 2565

DIGITAL DISPLAY 2667

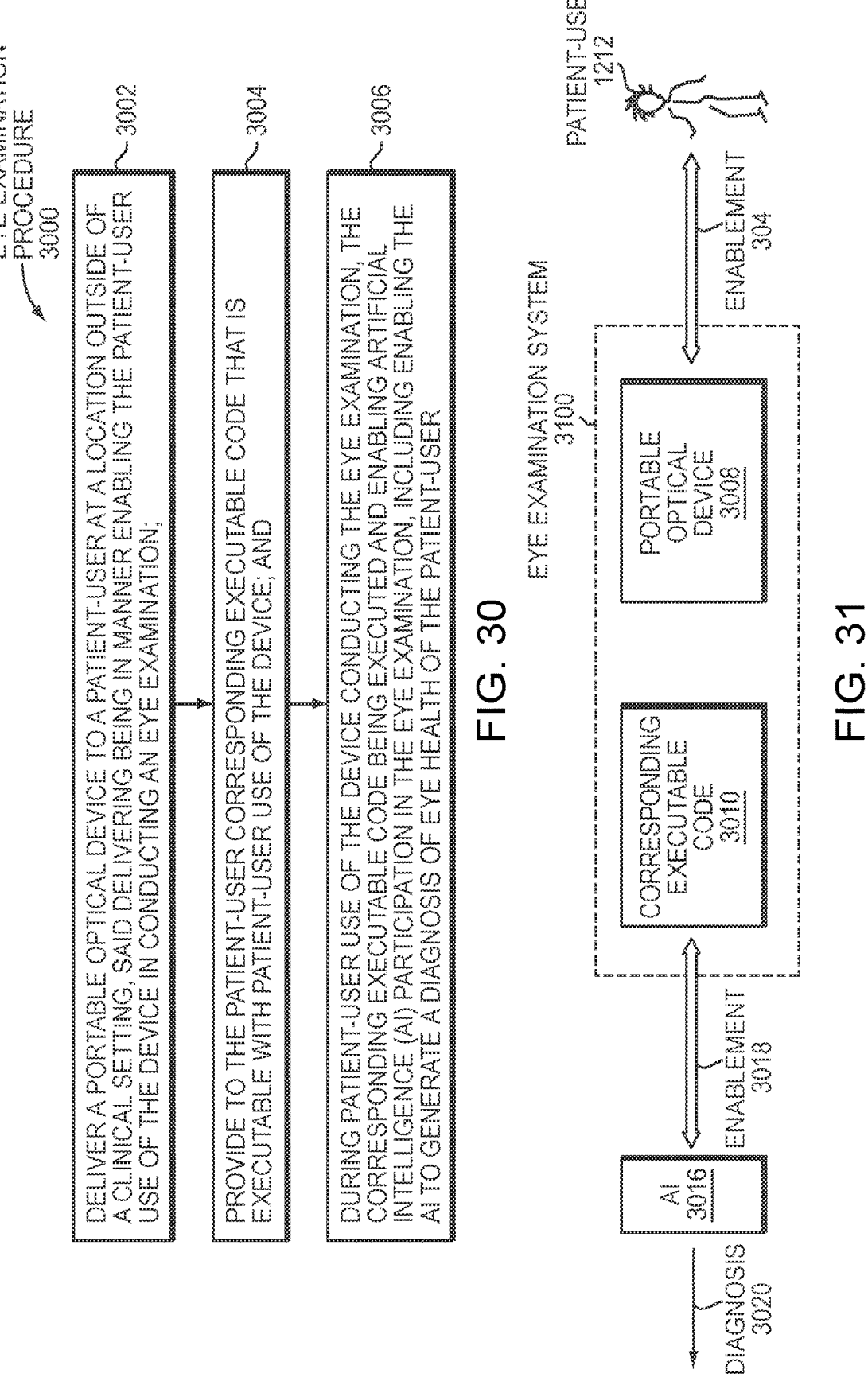

EYE EXAMINATION PROCEDURE 3000

DELIVER A PORTABLE OPTICAL DEVICE TO A PATIENT-USER AT A LOCATION OUTSIDE OF A CLINICAL SETTING, SAID DELIVERING BEING IN MANNER ENABLING THE PATIENT-USER USE OF THE DEVICE IN CONDUCTING AN EYE EXAMINATION; 3002

PROVIDE TO THE PATIENT-USER CORRESPONDING EXECUTABLE CODE THAT IS EXECUTABLE WITH PATIENT-USER USE OF THE DEVICE; AND 3004

DURING PATIENT-USER USE OF THE DEVICE CONDUCTING THE EYE EXAMINATION, THE CORRESPONDING EXECUTABLE CODE BEING EXECUTED AND ENABLING ARTIFICIAL INTELLIGENCE (AI) PARTICIPATION IN THE EYE EXAMINATION, INCLUDING ENABLING THE AI TO GENERATE A DIAGNOSIS OF EYE HEALTH OF THE PATIENT-USER 3006

FIG. 30

PATIENT-USER 1212

EYE EXAMINATION SYSTEM 3100

CORRESPONDING EXECUTABLE CODE 3010

PORTABLE OPTICAL DEVICE 3008

ENABLEMENT 304

AI 3016

ENABLEMENT 3018

DIAGNOSIS 3020

FIG. 31

EYE EXAMINATION METHOD AND SYSTEM

RELATED APPLICATIONS

This application is the U.S. National Stage of International Application No. PCT/US2022/072186, filed May 6, 2022, which designates the U.S., published in English, and claims the benefit of U.S. Provisional Application No. 63/185,158, filed on May 6, 2021. The entire teachings of the above applications are incorporated herein by reference.

GOVERNMENT SUPPORT

This invention was made with government support under R44 EY025452 from the National Institutes of Health. The government has certain rights in the invention.

BACKGROUND

There is a strong need to improve (make more convenient) access to clinical-quality vision exams. Digital health approaches hold promise to achieve this but have several limitations.

Typical teleoptometry applications are limited to measuring the patient with clinical equipment inside of a clinic, in the physical presence of a clinical practioner (technician or optician) where the doctor remotes in on a video screen. This is because most clinical equipment for testing the eye, and in particular vision, are large stationary pieces of equipment (e.g., desktop autorefractor, phoropter) and require operation by someone other than the patient (are not self-operable by the patient). Furthermore, portable autorefractors or trial frames (analog versions of phoropters) are typically not telecommunications connected, or self-operable by the patient.

SUMMARY

Certain prior art has explored having an arrangement wherein the patient is physically in the clinic, the clinical equipment is operated by a technician or remotely by the doctor (via remote control), and the doctor is present via a telecommunication system. Other prior art has explored providing a vision or eye health exam for a patient outside of a clinic, through the screen of a computer, tablet, or smartphone, synchronous or asychronously. However, these appproaches are not able to take clinical-quality optometric measurements of the eye (e.g., autorefraction, intraocular pressure, dry eye status, retinal images, anterior segment images), in part because particular optics, execuatable code, and peripheral components and techniques have not been available.

Embodiments of the present invention provide advantages and efficiencies lacking in the art. In particular, Applicants address long felt needs pertaining to administration of clinical eye examinations (i.e., vision exams) and generation of a diagnosis, a refractive correction, and/or eye glass prescriptions in rural areas or to patient populations who live relatively far from clinical settings.

Embodiments provide a clinical-quality eye examination method, inside or outside a clinic, comprising:
- a) delivering a portable optical device to the patient-user at a location outside of a clinical setting, the device configured for self-operation by the patient-user, or to be remotely operated by an eye care professional or by artificial intelligence, in conducting of eye (vision) exams;
- b) providing to the patient-user a corresponding software program executable with the patient-user use of the device; and
- c) during patient-user use of the device conducting an eye exam, running (executing) the corresponding software program which enables physician or qualified health professional (such as an optometric technician or ophthalmic technician, and the like) participation in the eye exam by audio-visual means. The physician, health professional, technician, or artificial intelligence participation in the eye exam can result in, or otherwise include, physician/health professional generation of a diagnosis, a refractive correction, and/or an eye glass prescription for the patient-user.

As used herein "self-operating" or "self-conducting" an eye (vision) exam using the portable optical device may include another onsite operator assisting the patient-user in taking measurements using the optical device on the patient-user (e.g., a parent, relative, caregiver, technician, and the like using the optical device on a child patient or patient in need of assistance).

In embodiments, the delivery location (of the portable optical device to the patient-user) is a random and remote location with respect to the physician/health professional. The delivery location is patient-user selectable and/or specified by the patient-user or his caregiver, parent, relative, etc. In this way, Applicants provide clinical eye or vision examinations at a patient's home, school, locations in the patient's community or neighborhood (e.g., public library, community center, etc.), clinics without an attending health professional, optical retail stores, patient-user workplace, kiosk, and the like as convenient for the patient-user.

Additionally, the corresponding software program may be provided to the patient-user preloaded on a computer, laptop, notebook, tablet, digital health wearable device (e.g., digital health watch), mobile phone, or other portable digital processing device shipped with the portable optical device. Likewise, the corresponding software program may be provided to the patient-user via a cloud server, through a website, or through an online platform accessed by a mobile device (e.g., mobile phone), digital health wearable device (e.g., digital health watch), or other camera-and-microphone-equipped computer at the disposal of the patient-user.

The physician/health professional, technician, or artificial intelligence participation by audio-visual means (that is, mechanisms of the mobile device/portable digital processing device running the corresponding software) utilizes common video and audio conferencing technology or videotelephony technology such as found in FaceTime (by Apple Inc), Zoom (by Zoom Video Communications, Inc.), Microsoft Teams, third party software, proprietary software, etc. In some embodiments, physician/health professional or artificial intelligence participation is by phone conference or audial means without a two-way video component.

In embodiments, the portable optical device determines optical properties of the eye. In addition, the portable optical device is self-operable (patient side operable) and of a hand-held, or equivalent, configuration and design for use by the patient-user. That is, the size and shape configuration of the optical device are conducive to operating and using the optical device by holding it in one's hands, or by removably securing it to a stand (for table top or floor), other similar bracketing system, or a head- or shoulder-mounted system, and the like. The portable optical device may thus be positioned and operated by the patient-user in conducting his own eye exam, or may be positioned and operated by an assisting operator conducting the eye exam on the patient-user. In some embodiments, the portable optical device includes a wavefront aberrometer and is of a binocular or monocular, open-view (or open field) design. Embodiments can include a tunable-lens based phoropter system, pupil camera, keratometer, retinal imaging capability, and other features. Non-limiting examples of such portable optical devices are described in: US Application Publication no. 2020/0046222 by Shivang R. Dave et al., U.S. Pat. No. 9,854,965 by Nicholas J. Durr et al., and U.S. Pat. No. 10,786,150 by Nicholas J. Durr et al., each incorporated herein in their entireties.

Embodiments include clinical eye examination or vision examination systems, kits, assemblies, and the like carrying out the disclosed method. In some embodiments, the corresponding software uploads optical measurement data generated by the portable optical device to the physician/health professional or artificial intelligence outside of, and possibly unrelated to, a video conference session. The corresponding software thus provides uploading and livestreaming of the optical measurement data (generated by the portable optical device) to the physician/health professional or artificial intelligence as a function of type of measurement data and/or health condition of the patient.

BRIEF DESCRIPTION OF THE DRAWINGS

FIG. 5B shows eyeglasses outside of the lensometer module, while FIG. 5C shows the eyeglasses inserted into the lensometer attachment.

FIG. 5F is a side-view illustration of the assembly, FIG. 5G is a perspective-view of the assembly, and FIG. 5H is an end-view illustration of the assembly; FIGS. 5I-5K are various illustrations showing the calibration cradle attached to the apparatus illustrated in FIGS. 5A-5C.

FIG. 7 (prior art) is a flow diagram illustrating an embodiment procedure for determining a property of an eye.

FIG. 9A (prior art) is a flow diagram illustrating how embodiment devices and methods can be used to perform lensometry.

FIG. 9B (prior art) is a flow diagram illustrating how embodiment apparatus and methods can be used to suppress speckle in wavefront measurements.

FIG. 9C (prior art) is a flow diagram illustrating how embodiment devices and methods can be used to perform objective refraction measurements.

FIG. 9E (prior art) is a flow diagram illustrating how embodiment devices and methods can be used to measure accommodation amplitude for evaluation of presbyopia.

FIG. 9F (prior art) is a flow diagram illustrating how machine learning can be implemented in embodiment devices and methods to predict subjective refractive preferences of an eye patient based on objective measurements.

FIGS. 10A-10B (prior art) are flow diagrams illustrating parts of a single procedure for determining subjective refractive measurements (phoroptry) for refractive eye correction using embodiment devices directly interacting with a patient.

FIG. 11 is a flow diagram illustrating an embodiment eye examination procedure enabling physician participation in an eye exam via remote audiovisual means.

FIG. 12 is a schematic block diagram illustrating an embodiment eye examination system corresponding to the procedure illustrated in FIG. 11.

FIG. 13 is a flow diagram illustrating an alternative embodiment eye examination procedure in which uploading and live streaming of optical measurement data are provided remotely to a health professional as a function of a type of optical measurement data or health consideration of a patient-user.

FIG. 14 is an alternative embodiment eye examination procedure that includes executable code assisting in alignment and maintaining alignment such that involvement of a healthcare professional or operator is not necessarily required.

FIG. 16 is a flow diagram of an embodiment eye examination method.

FIG. 17 is a color diagram illustrating how a head-mounted portable optical device may be used for remote measurements according to embodiments.

5

Figure 20:
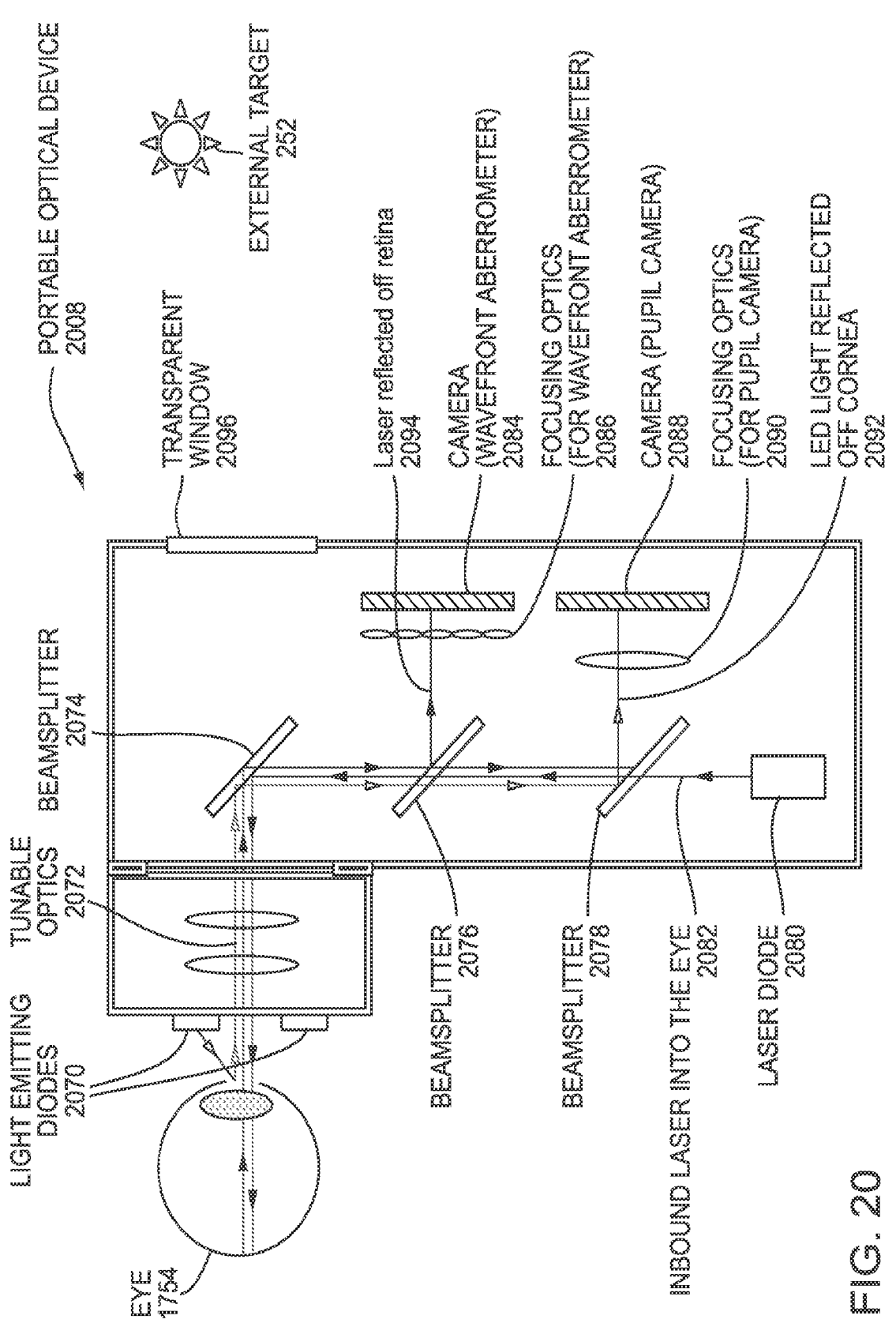
FIG. 20 is a schematic diagram illustrating a portable optical device that includes a pupil camera, consistent with various embodiments.
Figure 21:
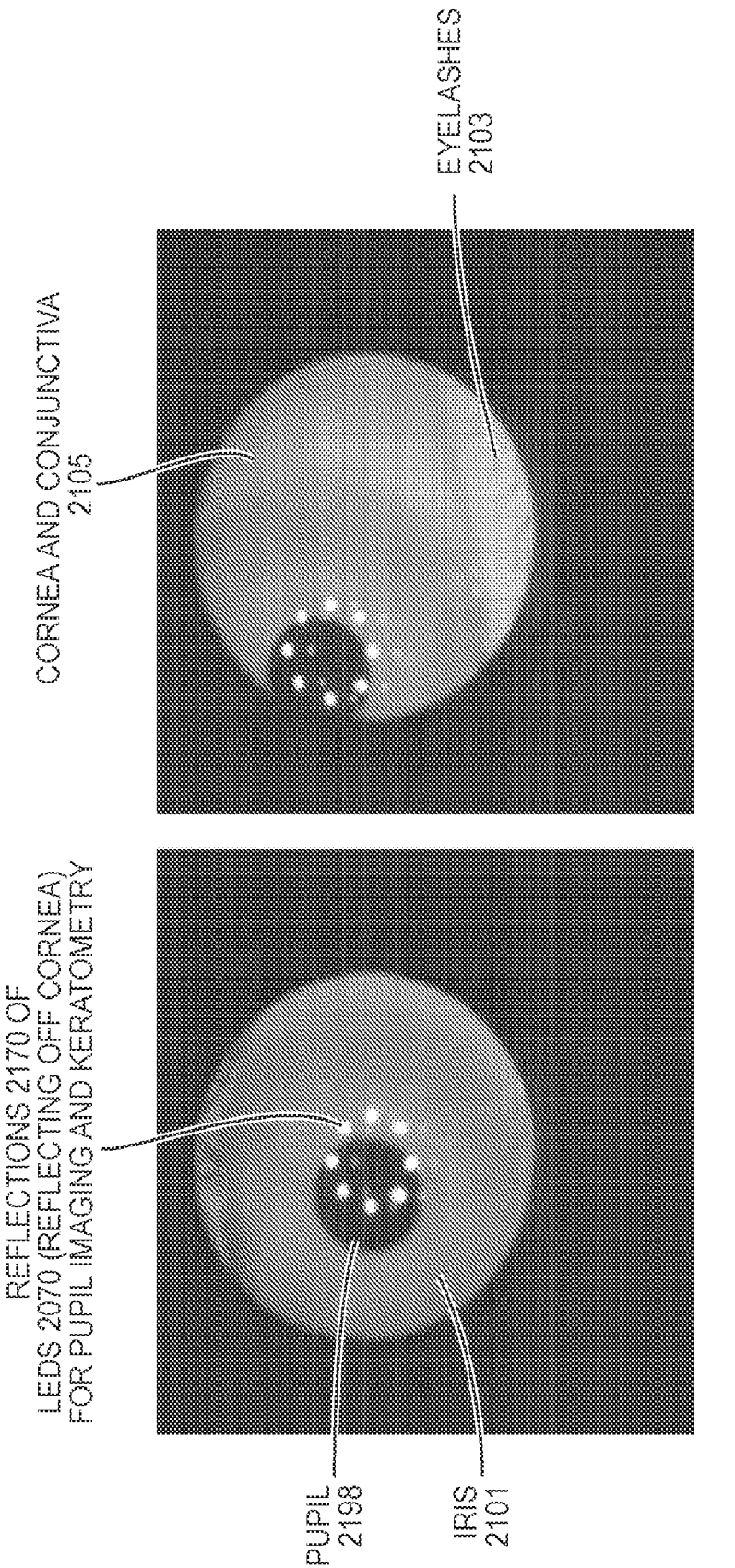

FIG. 21 is a pair of images of a human pupil imaged with a device that is similar to that of FIG. 20 having a pupil camera.

Figure 22:
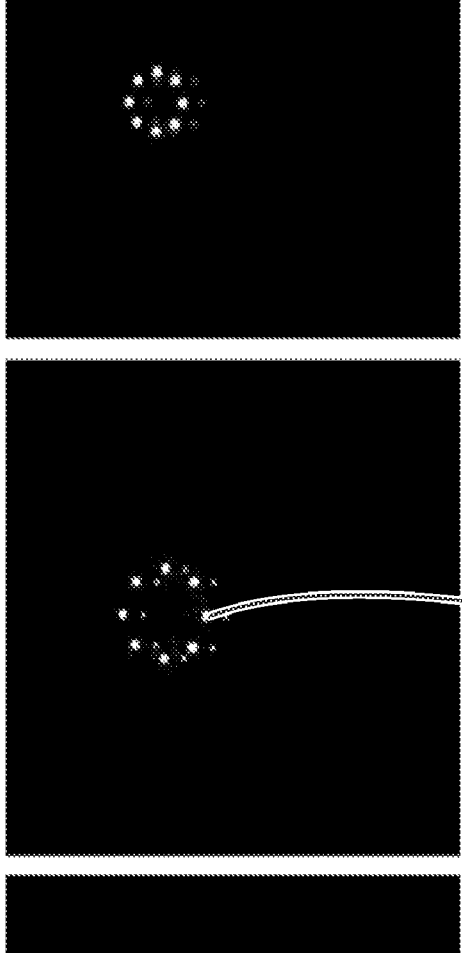

FIG. 22 is a series of three keratometry images illustrating how keratometry data can be derived by using a pupil camera such as the one described in FIG. 20 according to embodiments.

FIG. 23 is a flow diagram illustrating a procedure for alignment of device optics to a patient's pupil according to embodiments.

Figure 24:
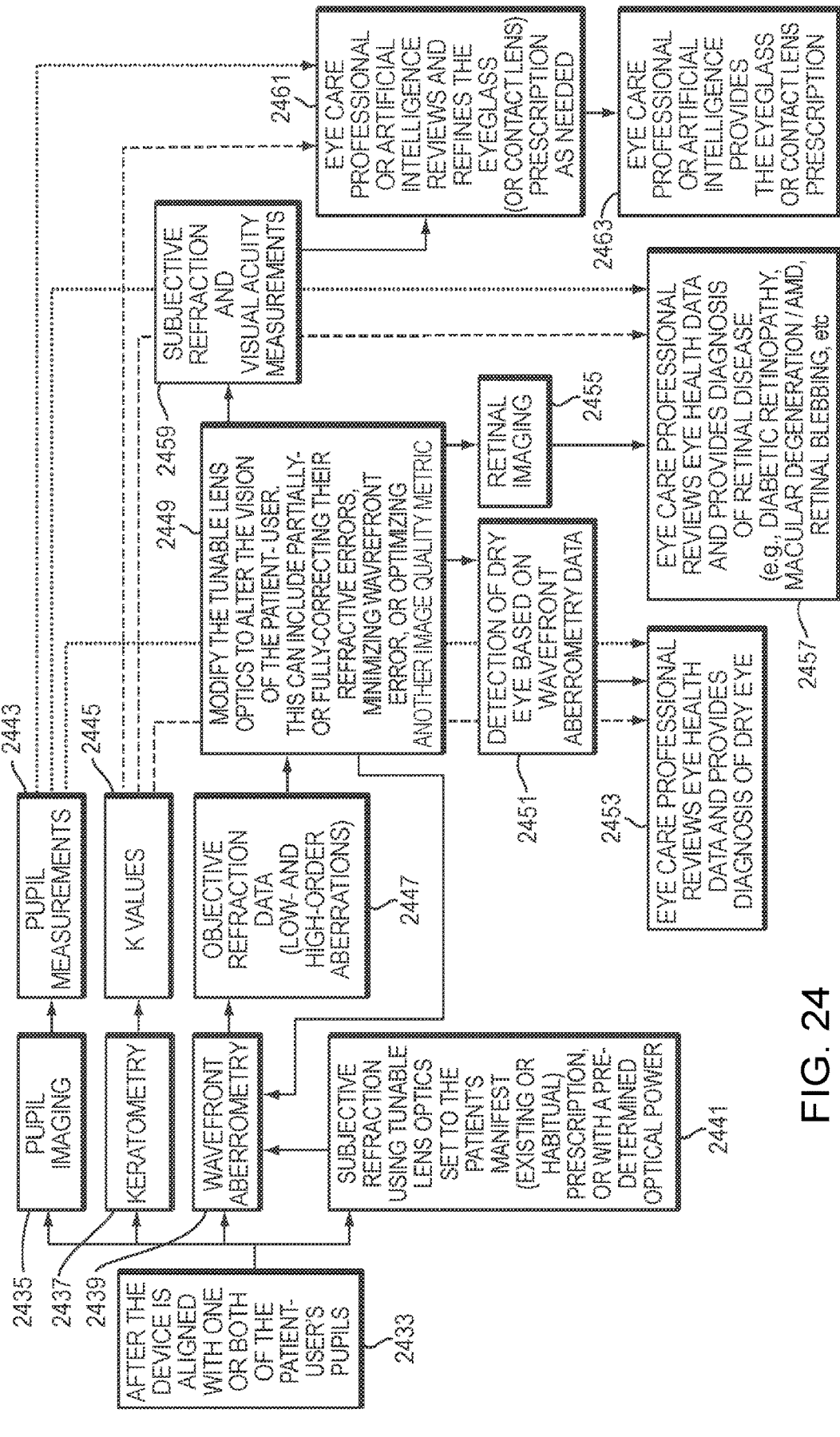

FIG. 24 is a flow diagram illustrating an example process for obtaining various eye health parameters from portable optical devices according to embodiments devices, systems, and methods.

Figure 25:
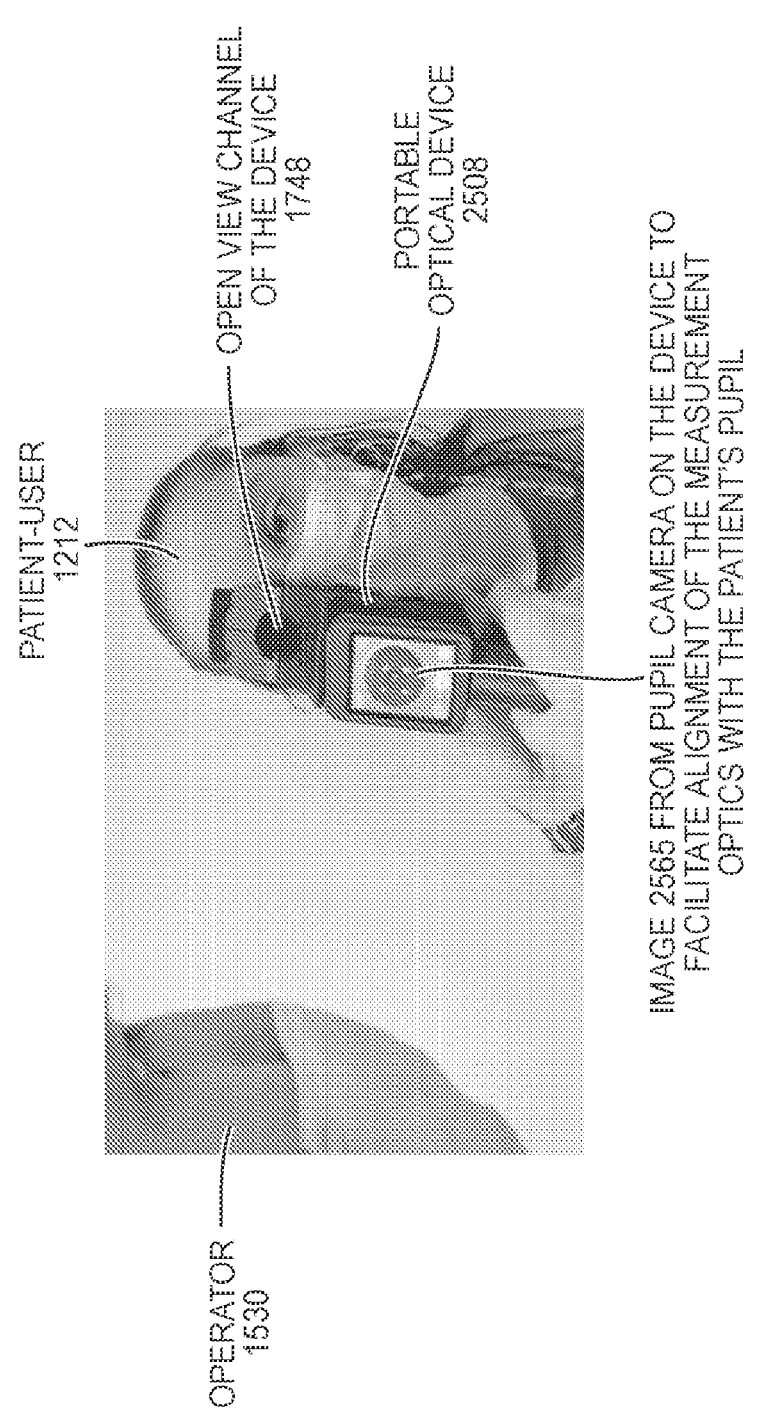

FIG. 25 is a photograph illustrating how an operator may use an image provided by a pupil camera on a portable optical device in order to align the device to a patient-user's eye for further measurements.

Figure 26:
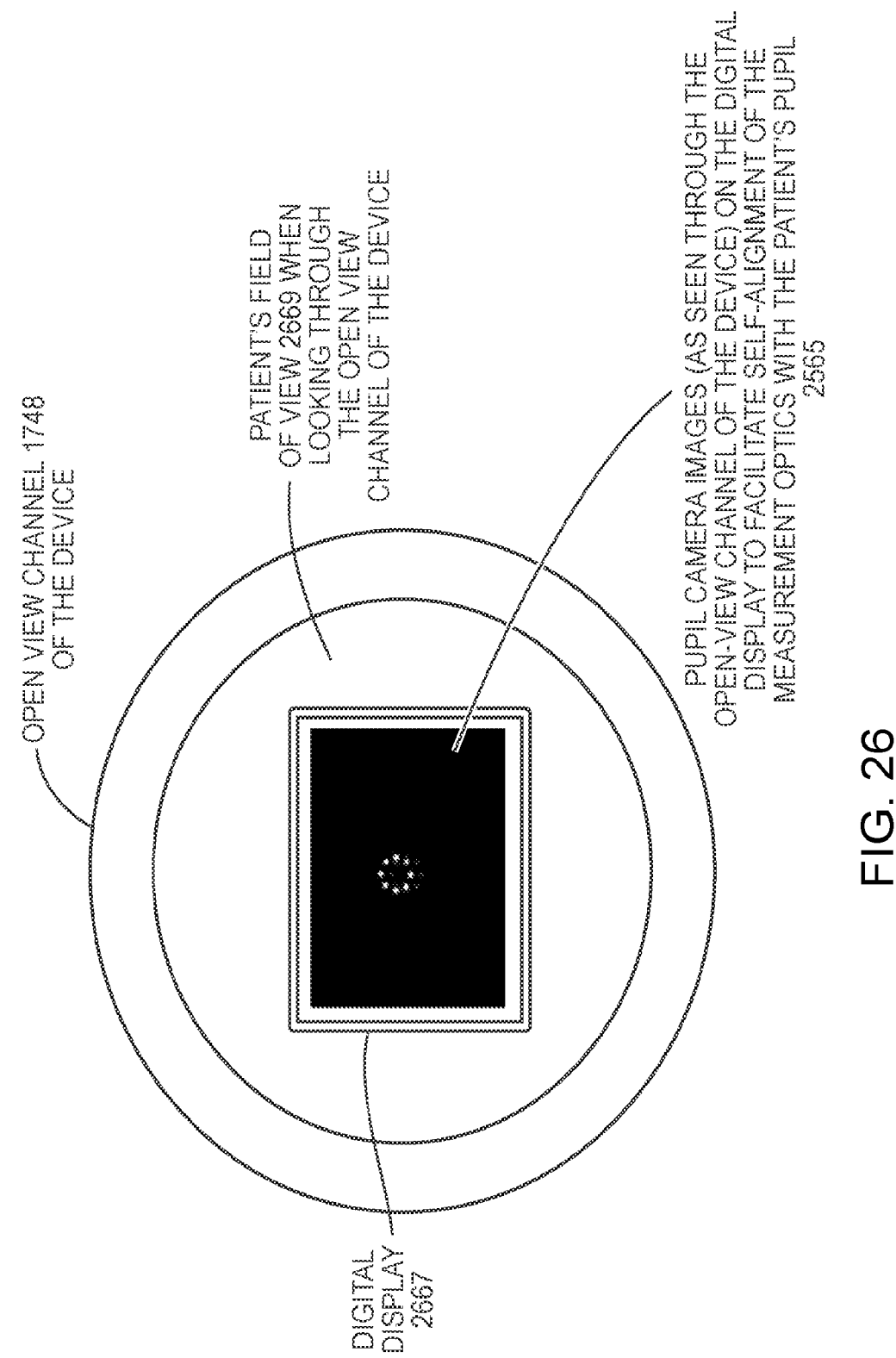

FIG. 26 is an example photograph illustrating how an operator can manually align a portable optical device to a patient-user's pupil using a pupil camera image displayed on the device.

Figure 27:
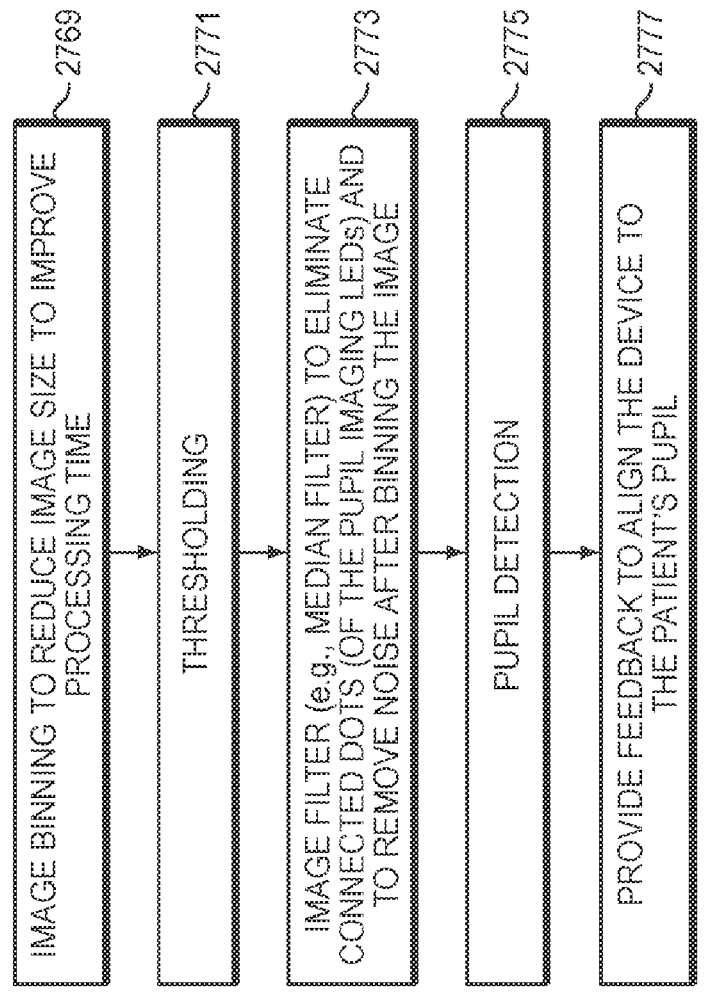

FIG. 27 is a flow diagram illustrating how people camera images can be processed in order to determine position of the pupil and provide alignment feedback according to embodiments.

Figure 28:
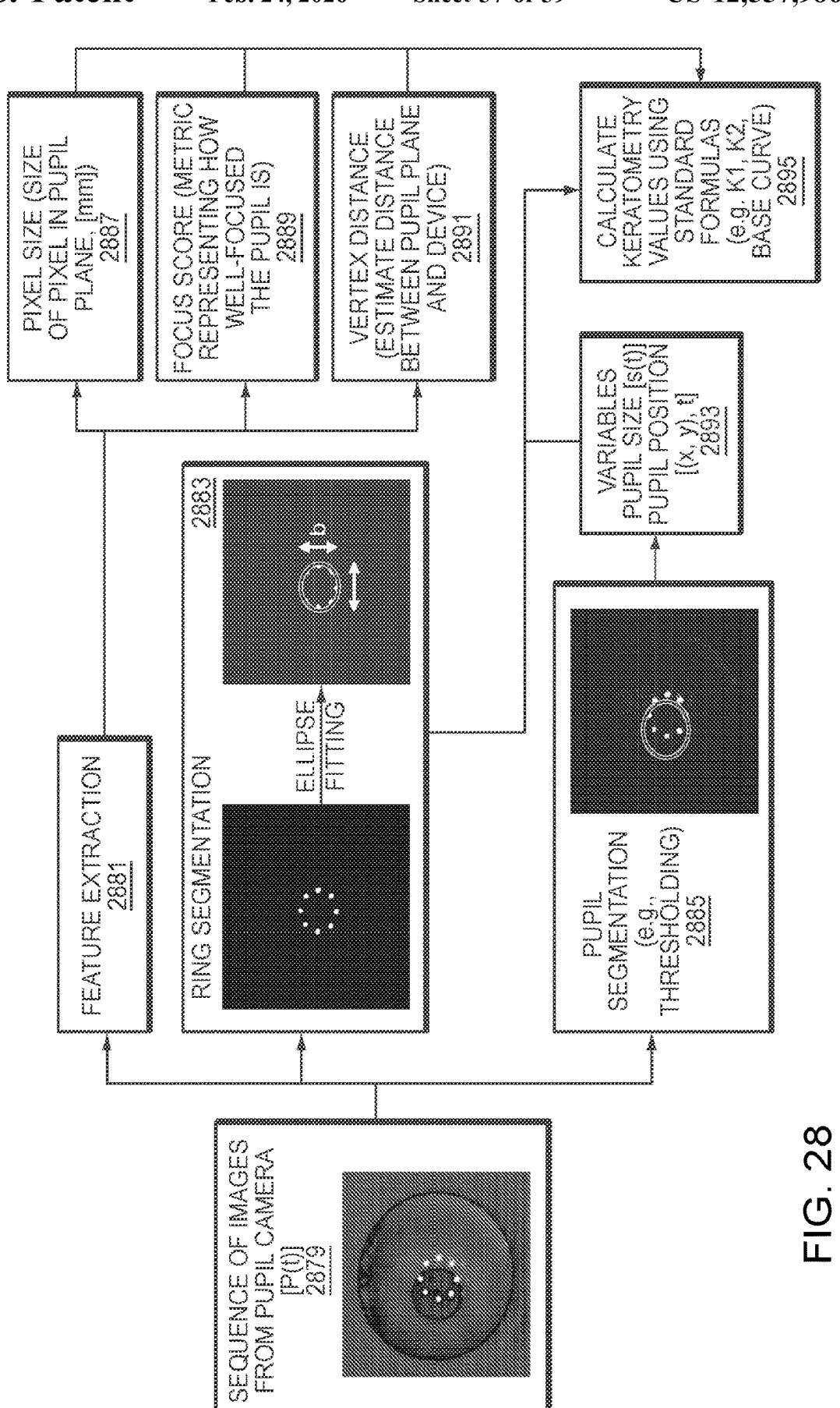

FIG. 28 is a flow diagram illustrating how a sequence of images captured by a pupil camera on a portable optical device can be processed to obtain keratometry values for an eye.

Figure 29:
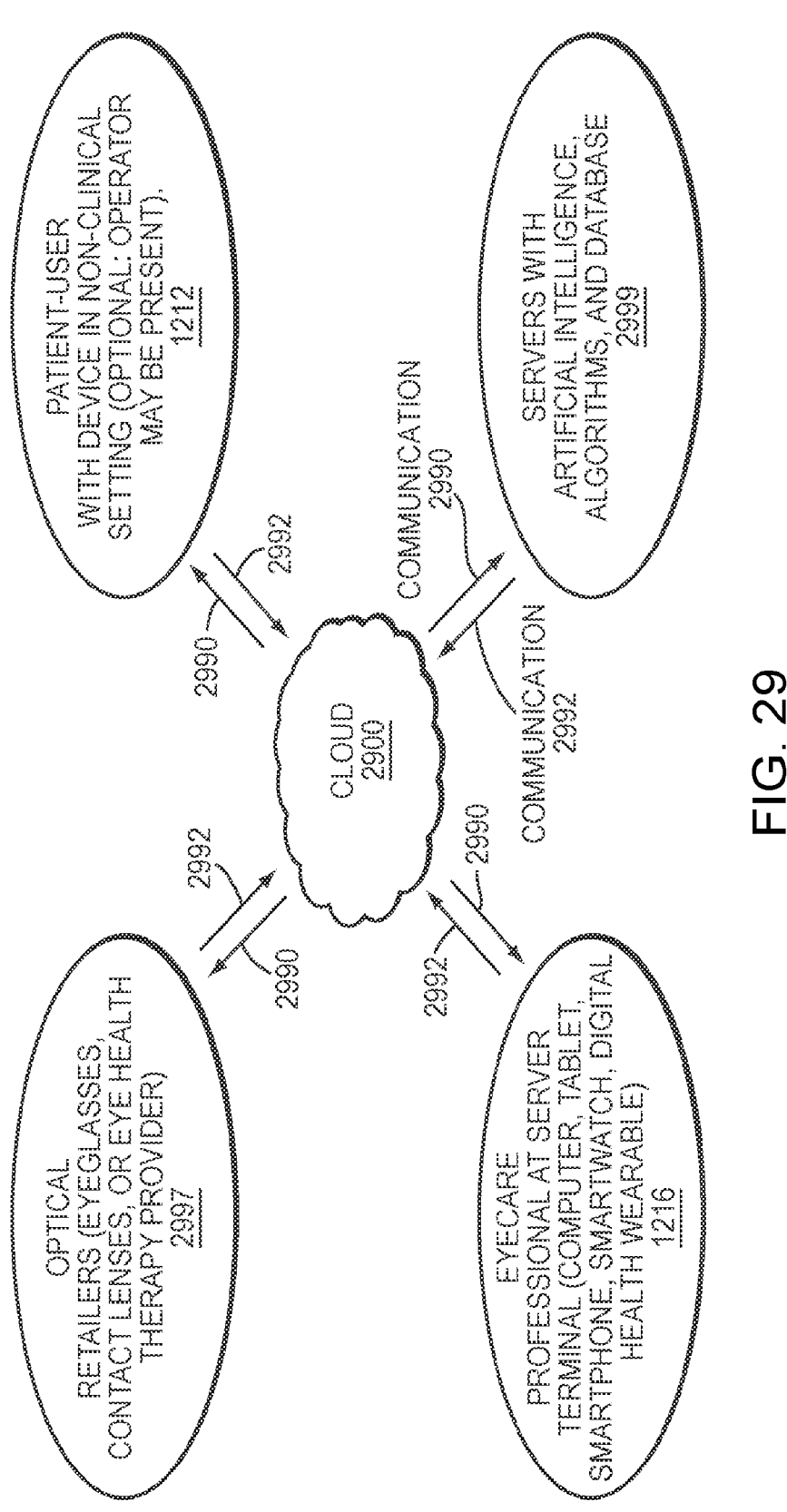

FIG. 29 is a schematic diagram of a cloud environment interconnecting a patient and portable optical device with other entities.

FIG. 30 is a flow diagram illustrating an embodiment procedure or eye examination using artificial intelligence.

FIG. 31 is schematic block diagram illustrating an embodiment system for eye examination using artificial intelligence, corresponding to the procedure of FIG. 30.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

U.S. Pat. No. 11,096,576

FIGS. 1-10B (prior art) are drawings from U.S. Pat. No. 11,096,576, granted on Aug. 24, 2021, which is hereby incorporated by reference in its entirety. U.S. Pat. No. 11,096,576 teaches various features that may be advantageously used in embodiments of the present application, and to which reference may advantageously be made in understanding the scope and details of the present embodiments. The teaching of U.S. Pat. No. 11,096,576 and corresponding description of FIGS. 1-10B follow in the next subjection.

Background of U.S. Pat. No. 11,096,576

Optometrists or ophthalmologists performing eye examinations in a clinic typically use a phoropter (or equivalently, a trial lens set) to determine which of many fixed lens settings produces the best eyesight, subjectively, for a given patient. However, this is a lengthy process due to the iterative nature of the subjective refraction. To speed up the process, objective measurements using a separate instrument are often used to reduce the number of iterations needed for subjective refraction with the phoropter. The relatively quick objective measurement of the refractive status of the eye serves as a good starting point for subjective refraction. Autorefractors are a common tool to perform such objective measurements of the eye. Wavefront aberrometers are a type of autorefractor which have been used in clinics to make objective determinations of eye aberrations. However, because wavefront aberrometers are typically more complex and expensive than other types of autorefractors, they have not typically been used for providing an initial starting for subjective refraction. Besides typical aberrations used for prescribing eyeglasses (defocus and astigmatism), wavefront aberrometry can also determine aberrations of higher order than phoroptry.

More recently, portable devices for performing wavefront aberrometry have been developed. These devices have the potential advantage of making refractive eye care more available and affordable, particularly in locations with few eye care providers.

Summary of U.S. Pat. No. 11,096,576

Existing portable wavefront aberrometers have several disadvantages. First, they do not allow a patient to view through the device so that the patient's eyes can automatically tend toward a relaxed, unaccommodated state. To counter this, cycloplegic drops can be used to disable accommodation. However, this treatment includes side effects and requires waiting time between treatment and aberrometry measurements. Another approach to relaxing accommodation is to "fog" the eye. However, this approach also has limitations and is not effective for all eye patients.

Furthermore, existing portable wavefront aberrometers (i) do not provide phoroptry measurements, which take into account a patient's subjective preference, which is typically slightly different from the correction indicated by purely objective measurements, or (ii) are not open view, allowing a patient to see through the device to a target external and spaced away from the device. Phoropters are typically large, bulky, heavy, and involve motion and vibration when lenses are switched, and all of these characteristics are undesirable in environments where handheld devices are used. While subjective refraction is considered the "gold" standard in evaluating patients for refractive correction, the phoropter is usually not used in environments where handheld portable wavefront aberrometers are employed. Instead, trial frames and lenses are used, which can be slower and more cumbersome to use.

While tunable lenses have been proposed for use with certain worn or portable devices, it is known that tunable lenses in many instances lack the precision of fixed lenses. Yet even with a multiple-fixed-lens phoropter-type system, wavefront aberrometry is still highly desirable for determining both lower- and higher-order corrections objectively, and the phoroptry and wavefront aberrometry functions have conventionally been performed using separate devices.

Embodiments described herein can overcome the limitations of existing, separate phoroptry and wavefront aberrometry systems by performing the same functions in the same unit. Furthermore, in many respects, better eye analysis and examination is possible using embodiment apparatuses and methods than is possible with two separate instruments for phoroptry and wavefront aberrometry, whether in a clinical setting or a field-use setting. Example advantages of embodiments include increased examination speed, more accurate refractive results, increased flexibility in patient and clinician use, and the ability to obtain wavefront aberrometry measurements at arbitrary times during phoroptry and accommodation measurements. Moreover, embodiments including portable apparatuses can even be configured to perform lensometry measurements. Embodiment apparatuses and methods can also provide patients with an indication of how their vision will improve with lenses having refractive corrections that are determined by the same system based on objective wavefront aberrometry, subjective phoroptry measurements, or both.

Furthermore, embodiments described herein can overcome the limitations of existing portable wavefront aberrometers by providing open-view, binocular configurations that do not necessarily require the use of cycloplegic drops or fogging. Embodiment devices and methods can include using one or more tunable lenses incorporated into a device to improve the accuracy of wavefront aberrometry measurements, perform subjective phoroptic measurements, simulate final refractive correction for the patient, and perform lensometry measurements. Thus, by combining a wavefront sensor and a tunable lens, embodiments described herein can achieve many advantages that have not been achievable with existing devices that seek to use either one or the other, and these advantages will become more apparent throughout the description hereinafter.

In one embodiment, an apparatus for determining a property of an eye, and corresponding method, includes a housing having a port configured to receive an eye (i.e., to serve as a viewing port through which an eye being assessed can view) and to receive light from the eye. Light can be received from the eye by directing a source of eye illumination light from the apparatus into the eye and then collecting light that is thereby reflected or backscattered from the eye, for example. The property of the eye can be a refractive property such as a lower- or higher-order refractive aberration, a refractive prescription, an accommodation range, or another refractive property related to eyesight.

The apparatus further includes a visual tunable lens mounted to, or configured to be mounted to, the housing to apply a variable focal power to the light from the eye and to pass the light along an optical path. The apparatus also includes a wavefront sensor within the housing, the wavefront sensor being configured to receive the light from the eye via the optical path and to measure a wavefront of the light from the eye. The apparatus still further includes a determination module configured to determine a property of the eye based on the wavefront. The property of the eye can be a refractive prescription needed to correct the vision of the eye, a spherical aberration, a cylindrical aberration, an axis for cylindrical aberration, a refractive error of higher order than spherical or cylindrical aberrations (i.e., defocus and astigmatism), a range of accommodation, an objective refractive measurement, a subjective refractive preference of a person having the eye, or other property of the eye.

The housing can be configured to be gripped by at least one hand of the person having the eye (i.e., the person whose eye is to be assessed using the apparatus) to support a full weight of the apparatus during use. The port can be further configured to receive a corrective lens applied to the eye, and the wavefront sensor can be further configured to measure the wavefront of the light from the eye in combination with the corrective lens. The port can be a first port, the eye can be a first eye, and the housing can further include a second port configured to receive a second eye of the same person (whose eye is to be assessed using the apparatus), wherein the housing defines a binocular configuration.

The visual tunable lens can be a first visual tunable lens, and the apparatus can further include a second visual tunable lens configured to be mounted to the housing and to apply a variable focal power to light from the second eye.

The port can be a proximal port, and the housing can further includes a distal port, the proximal and distal ports together forming a visual channel from the proximal port through the distal port, the visual channel providing an open view to enable the eye to see target indicia external to and spaced away from the housing through the visual channel.

The apparatus may also include a target light source mounted to the housing and configured to produce the target indicia external to and spaced away from the housing, the target indicia being viewable by the eye through the visual channel. The target light source can be further configured to produce the target indicia at a distance of effective infinity from the eye.

The apparatus can further include an eye illumination light source in the housing, and the eye illumination light source can be configured to direct light through the proximal port and into the eye to produce the light from the eye via reflection or backscattering from the eye. A light source tunable lens can also be included in the apparatus and can be configured to apply a variable focal power to light from the eye illumination light source. The light source tunable lens can be further configured to randomize a speckle pattern produced by the eye illumination light source at the eye or a speckle pattern produced by the light from the eye at the wavefront sensor. The port may be further configured to receive the light from the eye non-collinearly with respect to the light from the illumination light source directed through the port and into the eye. Light from the eye illumination light source can be restricted by an aperture that can be included in the apparatus, and a diameter of the aperture can be between about 50 μm and about 500 μm.

The visual tunable lens can be configured to randomize a speckle pattern produced by the eye illumination light source at the eye or a speckle pattern produced by the light from the eye at the wavefront sensor. The visual tunable lens can be further configured to be situated at a spectacle plane of the eye with the proximal port having received the eye.

The determination module may be further configured to determine a refractive correction to be applied to the eye, or to determine one or more wavefront errors of higher order than defocus and astigmatism. The determination module can be further configured to determine a lens wavefront error due to the visual tunable lens for calibration, or to determine an accommodation range of the eye as a function of a plurality of wavefront measurements of the light from the eye.

The housing can be configured to receive a lensometer attachment, and the lensometer attachment may be configured to support a corrective lens intended to be worn by a person, or a lens blank intended to be manufactured into a corrective lens. The determination module can be further configured to determine to determine a refractive property of the corrective lens or lens blank based on a lens wavefront of light received through the corrective lens or lens blank.

The apparatus can further include a closed-loop control circuit configured to adjust the variable focal power of the visual tunable lens iteratively in response to successive wavefront measurements to minimize a wavefront error of the light from the eye. The apparatus can further include a control circuit configured to adjust the visual tunable lens in accordance with a subjective refractive preference of a person having the eye. The apparatus can also include a manual control configured to be adjustable by a person having the eye, or someone else helping the person having the eye, to adjust the variable focal power of the visual tunable lens in accordance with a subjective refractive preference of a person having the eye.

The apparatus can include a reporting interface configured to report a prescription for refractive correction of the eye. The apparatus can also include a communication interface configured to query a person having the eye, or receive a response from the person, regarding a subjective, refractive preference. The apparatus can also include a fixed lens configured to be attached to the housing and to apply a fixed focal power to the light from the eye to shift a range of refractive correction measurement of the apparatus, or a fogging lens configured to be attached to the housing and to fog a view of the eye.

The sensor module or determination module can include a cellular phone, or the apparatus can further include a cellular phone configured to be attached to the housing or to display a representation of the wavefront of the light from the eye. The wavefront sensor can include a pixel array of a cellular phone.

The apparatus can also include cross-polarizers disposed within the optical path.

The visual tunable lens can be further configured to apply a variable spherical power, astigmatic power, and axis mutually independently. The visual tunable lens can be further configured to apply a spherical equivalent power, vertical Jackson cross cylinder, and oblique Jackson cross cylinder mutually independently. The visual tunable lens can include at least one of a liquid-filled lens, an electro-wetting lens, an Alvarez lens pair, spatial light modulator, deformable mirror, lens with power that varies spatially, a multi-lens system that changes lens distances to tune optical power, or a tunable Fresnel lens. The visual tunable lens can include a two-element optic configured to apply the variable focal power as a function of lateral or rotational displacement of the two elements with respect to each other.

The property of the eye can be an objective property based on the wavefront, and the determination module can be further configured to predict a subjective refractive preference of a person having the eye based on the objective property. The determination module can be further configured to predict the subjective refractive preference based further on a demographic or physical attribute of a person having the eye. Demographic attributes can include at least one of an age, gender, ethnicity, weight, height, occupation, or another demographic attribute of the person having the eye. Physical attributes can include at least one of a retinal image quality, axial length, iris color, topography, corneal curvature, aberration of higher order than spherical or cylindrical aberration, or another attribute of the eye. The determination module can be further configured to predict the subjective refractive preference using a correlation developed from a database including respective demographic or physical attributes and respective objective eye properties of a plurality of eye patients.

In another embodiment, a method for determining a property of an eye, and corresponding apparatus, includes applying a variable focal power to light received from an eye, via a port of a housing configured to receive the eye, using a visual tunable lens. The method also includes passing the light from the eye along an optical path, as well as measuring a wavefront of the light from the eye, the light received via an optical path from the port. The method further includes determining a property of the eye based on the wavefront of the light from the eye.

Detailed Description of U.S. Pat. No. 11,096,576

A description of example embodiments of the invention follows.

Refractive eye examinations by an optometrist or ophthalmologist typically involve using a phoropter to determine which of many fixed lens settings produces the best eyesight, subjectively, for a given patient. Clinical phoropters are usually binocular (enabling both of a patient's eyes to view through separate sets of lenses) and open-view (enabling a patient to view, through the phoropter lenses, a distant target pattern). Typically, the patient is asked to focus on a target pattern situated a distance of about 20 feet from the patient's eye. The open-view design also performs the important function of encouraging the patient's eyes to remain unaccommodated (relaxed and as optimized as possible for long-distance viewing) during the measurement. The unaccommodated state is an important clinical prerequisite for accurate measurements for refractive correction of distance vision. Thus, using typical clinical phoropters, a prescription for refractive correction can be obtained that both (i) corrects for important types of optical aberrations of the eyes and (ii) takes into account a patient's subjective feedback about which correction is preferable.

Wavefront aberrometers, in contrast to clinical phoropters, determine a refractive correction for a patient objectively, without input from the patient, based on sensing a wavefront of near infrared (near-IR) directed into the eye and reflected or scattered from the retina of the eye. Wavefront aberrometry in an eye clinic can provide information about aberrations of the eye of higher order than just sphere and cylinder and is considered a valuable tool in determining refractive correction.

Handheld devices have been developed more recently to perform wavefront aberrometry. A goal of these devices is to enable refractive examination of people in remote areas without access to standard clinics or eye care professionals, as well as to decrease cost of examination and limit the number of expensive instruments required, as well as to streamline the refractive examination in high-resource settings. Handheld wavefront aberrometer devices have some limitations, in that they do not take into account subjective feedback from an eye patient. Further, high-quality clinical phoropters may not be available to supplement handheld device measurements, due to the cost, size, weight, and mobility limitations of standard phoropters.

Moreover, an important clinical requisite for an accurate measurement is that the patient's eye should be relaxed while the measurement is made. Since existing handheld devices do not allow a patient to view through them and focus on a distant object to cause eye relaxation, there are a number of other techniques that have been used to induce relaxation using existing non-open view devices. For example, cycloplegic drops can be placed in the eye to paralyze accommodative control. While effective, these drugs may often have side effects that can be undesirable for the patient and can require 15 minutes or more for their effects to occur. Another approach is to place lenses in front of the patient's eyes to simulate myopia (i.e. shortsightedness), referred to as "fogging" the patient, so that the patient's eye(s) are coerced into relaxing their accommodation so as to bring a fixation target into focus. While fogging can be effective for many patients, some others may not respond well to this technique. Furthermore, these techniques, even when effective, still do not produce exactly the same results as actually allowing a patient to view a distant target through an open view lens, as is done with standard clinical phoropters.

Including a set of physical lenses, similar to those of a phoropter, with a handheld device has been attempted. However, this increases cost, weight, and system complexity, and this solution also has feasibility challenges because switching between lenses requires at least some mechanical motion or disturbance of a portable handheld device. Thus, this approach would be less mechanically robust and prone to breaking or mis-alignment. Alternative optical approaches such as adaptive optics (e.g., deformable mirrors, spatial light modulators) are prohibitively expensive for application in low-cost diagnostics.

Embodiment apparatus examples can include one or more tunable lenses integrated into a handheld wavefront aberrometer to act effectively as an on-board phoropter. Wavefront aberrometer measurements can be used as feedback to the tunable lens, in closed-loop fashion, to automatically and quickly adjust a tunable lens through which the patient views to optimize vision objectively. Because the tunable lens can iteratively correct measured wavefront errors until the measured wavefront is nominally parallel, objective wavefront evaluations can be made with greater accuracy. As will be understood by those familiar with Hartmann-Shack wavefront sensors, for example, when the wavefront is nominally parallel, a spot pattern produced by the sensor has spots nominally uniformly spaced. In this state, uniformity of the spot pattern (and, hence, wavefront errors) can be more exactly evaluated than if the spot pattern is very distorted.

After objective autorefraction, feedback from a patient can be used to further adjust the tunable lens in accordance with subjective patient preference to improve the proposed correction. An apparatus can communicate with a patient through a variety of methods to obtain the subjective feedback, even automatically or semi-automatically. This feedback can be obtained and implemented in embodiment devices with or without the assistance of a technician or other eye professional. Embodiments can be designed to be self-usable by a single user (i.e., eye patient) without assistance from a clinician (e.g., an ophthalmologist, optometrist, clinical assistant, field technician, or any other person working to assist an eye patient to obtain a corrective prescription).

Self-usable embodiments are made possible in part because the eye can be aligned with the optics of the device via an external or internal fixation target, or visual or audio cues from the device, or both. Self-usable embodiments can be further enabled by automated or semiautomated operation of embodiment apparatuses and interactive instruction to a patient and saving settings made by a patient. FIGS. 10A-10B, as described hereinafter, provide one example of such an interactive procedure consistent with some embodiment apparatuses. However, embodiments disclosed herein may also be modified and used advantageously with clinician assistance to obtain results that are similarly unachievable by other handheld units and further unachievable by using mutually separate phoroptry and aberrometry instruments.

Thus, integrated autorefraction and phoropter functions allow the phoropter core (the tunable lens) to be automatically updated based on the autorefraction wavefront data. Furthermore, when the tunable lens is appropriately situated in or on the device incorporating the wavefront sensor, the tunable lens can serve as an eyeglass simulation to allow a patient to see through a lens at the appropriate location for an eyeglass with the final, proposed correction prescription implemented. Moreover, certain embodiments can be used to take advantage of the tunable lens to measure accommodation and presbyopia, as well as to perform lensometer functions by measuring optical parameters for a set of eyeglasses already owned by the patient or to be offered to the patient, for example. Furthermore, the lenses to be measured using embodiment devices may be lens blanks as well. An optician may want to locate the optical center position and confirm the power of the lenses before cutting the lens blanks to fit an eyeglass frame, for example.

Embodiment devices are preferably "open view," meaning that the patient can see through the device to a distant target to relax any accommodation of the eye. An embodiment apparatus can be designed to measure the aberrations of the user's eye in an unaccommodated state (i.e. the eye is relaxed and focused at infinity). A viewing target may be located at effective optical infinity, about 20 feet from the patient's eye. Viewing targets can include a standard eye chart, a spot of light produced by a target light source on the device, or another object in the surrounding environment. Such open view designs can reduce or eliminate the need for cycloplegic drops, and fogging may also be rendered unnecessary or optional.

By using a relatively low-cost, electronically tunable lens system, expensive approaches such as adaptive optics can be avoided. Embodiment devices can also be more mechanically robust and easier to handle and transport than systems having a set of physical lenses included in a phoropter, for example. A standard phoropter-style or trial frame lens system requires lens switching, which can result in fluctuations of the patient's eye and mechanical disturbances to the wavefront sensor apparatus.

It is noteworthy that available tunable lenses may have lower optical quality than fixed lenses typically used in high-quality optical systems for eye care. For this reason, optical engineers and eye care professionals would not generally be inclined to consider using a tunable lens in a system designed for high-quality eye examination, whether a phoropter or a wavefront aberrometer. However, the inventors have recognized that, where a device is designed for a tunable lens to work in combination with a wavefront sensor, the quality of wavefront aberrometry can be maintained and even enhanced due to iterative wavefront measurements in the presence of automatic, closed-loop, wavefront error cancellation by the tunable lens. Embodiments can provide wavefront measurements that are captured and processed continuously, such as at video rates, for example. Furthermore, a wavefront sensor apparatus can be calibrated with respect to any wavefront error caused by a tunable lens, thus enabling measurement of even high-order wavefront errors of a patient's eye with high accuracy. Furthermore, as noted hereinabove, a tunable lens also enables fast automated or semi-automated phoropter, lensometer, and accommodation measurement functions on the same device that is used for wavefront aberrometry, even with a portable, handheld device, and even when testing is self-administered by the patient.

Embodiments can provide a complete refraction system that enables refractive measurements to be performed anywhere by a minimally-trained technician or even by the subject patient himself or herself. This has significant global health and industrial utility.

Figure 1:
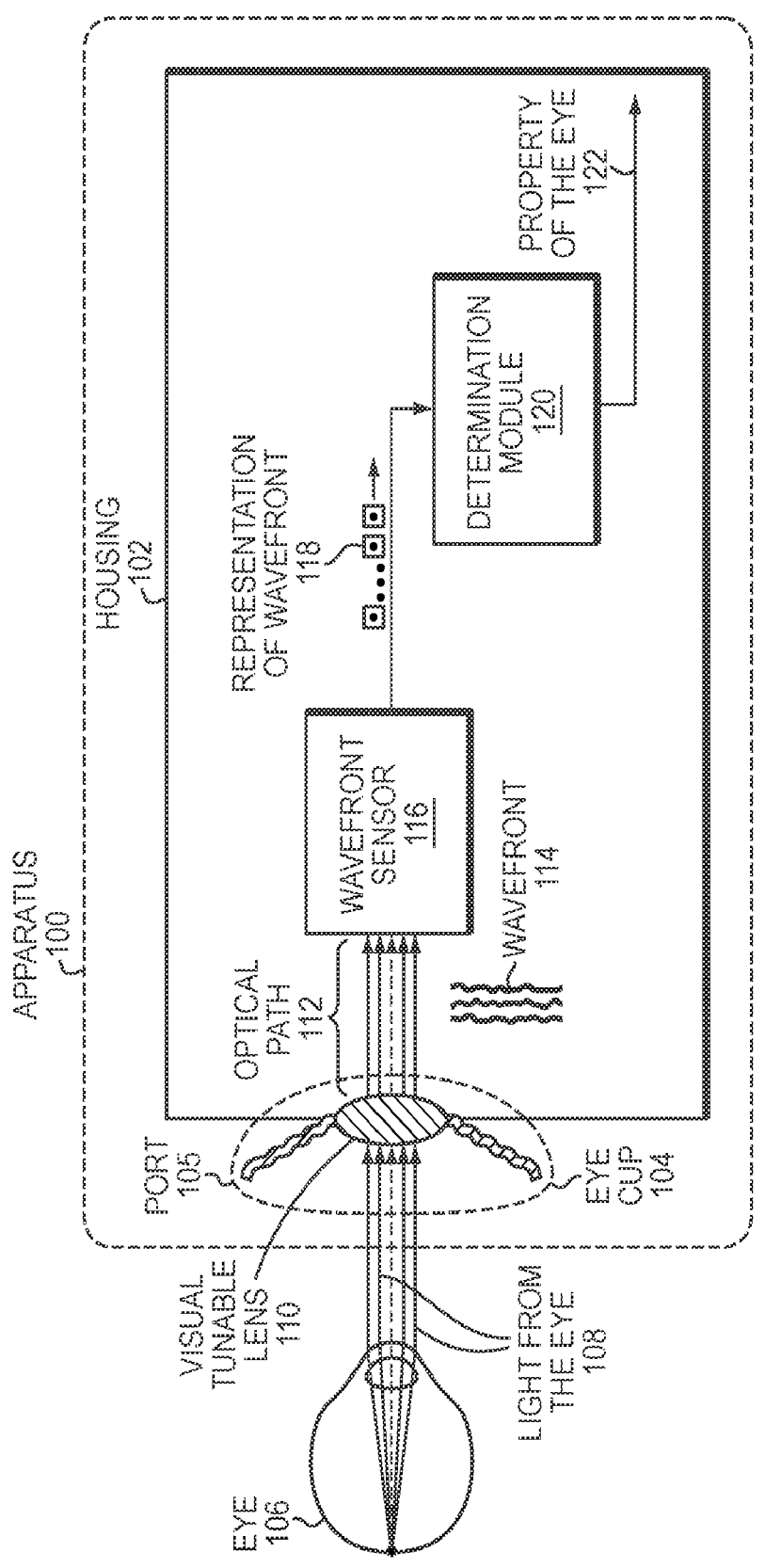
FIG. 1 (prior art) is a schematic block diagram illustrating an embodiment apparatus for determining a property of an eye.

FIG. 1 is a schematic block diagram illustrating an embodiment apparatus 100 for determining a property of an eye 106. The apparatus 100 includes a housing 102 having a port 105 configured to receive the eye 106 and to receive light 108 from the eye. The port 105 is "configured to receive" the eye 106 in the sense that the eye 106 can be placed near enough to, or in contact with, one or more portions of the port such that the light 108 from the eye can be received through the port 105. Thus, while the eye 106 is not required to be in contact with the port 105, in various embodiments, the eye 106 is an eye of a person whose forehead and cheek are placed against an eyecup 104 for registration and mechanical fixation with respect to the port 105. As a further example, another embodiment device having an eyecup configured to come into contact with a person's forehead and cheek is described hereinafter in connection with FIGS. 5A-5C. Some embodiments defining a binocular configuration may include two ports, also referred to herein as "first" and "second" ports, that include similar configurations and provide for similar functionalities for first and second respective eyes of a patient, as described in connection with FIGS. 5A-5C, for example.

The apparatus 100 in FIG. 1 also includes a visual tunable lens 110 mounted to the housing as part of the port 105. The visual tunable lens 110 is designated "visual" because it is possible for the eye 106 to see through the visual tunable lens 110. The visual tunable lens 110 is also configured to focus or defocus light received from the eye 106 to be passed via an optical path 112 to a wavefront sensor 116, which measures a wavefront of the light 108 from the eye. The "visual" tunable lens 110 is also closer to the eye 106, when the apparatus 100 is in use than an optional "light source tunable lens" that will be described in connection with FIG. 2, and which can be a similar tunable lens at a different location in the apparatus. In various embodiments, the visual tunable lens 110 mounted in the apparatus such that it is relatively close to the eye 106 when the apparatus is brought into proximity with the eye for examination. A smaller relative separation between the tunable lens and the eye can result in the tunable being smaller and less expensive than would otherwise be needed.

The visual tunable lens 110 has a focal length f and an optical power P=1/f that are variable. In some embodiments, the visual tunable lens 110 is configured to apply a variable spherical power (focus/defocus) to the light 108 from the eye. In other embodiments, the visual tunable lens 110 can also apply astigmatic power (cylinder) and also vary axis of the cylindrical (astigmatic) power applied to the light. In some embodiments, the visual tunable lens can be configured to apply variable spherical and astigmatic optical powers, as well as apply axis orientation for the astigmatic power, mutually independently. In some embodiments, the visual tunable lens 110 is further configured to apply a spherical equivalent power, vertical Jackson cross cylinder, and oblique Jackson cross cylinder mutually independently.

It should be understood that any "tunable lens," as used herein, can include a plurality of individual tunable lenses arranged (optically stacked) in series, along the same optical axis, for example. Individual tunable lenses can be stacked in series (along the same optical axis) in order to increase the range of lens powers that can be simulated by the system. Stacking of tunable lenses may also improve the dynamic range or reduce the overall aberrations of the system. For example, a visual tunable lens may include a first individual tunable lens with a wide range of coarse tunability for a given optical correction such as sphere, as well as a second individual tunable lens with a narrow range of fine tunability for the given optical correction. Further, the optional mutual independence of spherical and astigmatic powers with variable axis may be achieved by applying the powers and axis using respective individual tunable lenses. This same method of using individual tunable lenses can be used to apply spherical equivalent power, vertical Jackson cross cylinder, and oblique Jackson cross cylinder mutually independently.

In some embodiments, the visual tunable lens 110 can be at least one of a liquid-filled lens, an electro-wetting lens, an Alvarez lens, spatial light modulator, deformable mirror, a lens with power that varies spatially (e.g., a progressive lens), a multi-lens system that changes lens distances to tune optical power (e.g., optical trombone, Badal system), or a tunable Fresnel lens. In some embodiments, the visual tunable lens can include a two-element object configured to apply the variable focal power as a function of lateral or rotational displacement of the two elements with respect to each other. For example, an Alvarez lens pair can include two such optical elements configured to be laterally displaced with respect to each other, in a direction perpendicular to an optical axis of the elements, to apply the variable focal power. Another embodiment includes a lens that is tunable by virtue of being asymmetrical having different focal powers along different points on the lens. Such an asymmetrical lens can be displaced along a plane perpendicular to an optical axis of the system in order to vary the focal power of the lens. Asymmetrical lenses of this type have been termed "hybrid Fresnel lenses" and have been used in virtual reality headsets, for example.

Example tunable lenses that can be used in embodiments described herein can include, for example, the Optotune® EL-10-30 series of liquid-filled tunable lenses. This series has focal lengths and corresponding optical powers that can be tuned within milliseconds, providing fast response for iterative wavefront measurements performed in a closed loop fashion, as further described hereinafter. One model of the Optotune® EL-10-30 can be tuned between +8.3 and +20 diopters (dpt) of optical power, corresponding to +120 to +50 mm in focal length, for example. Furthermore, the Optotune® EL-10-30 series is available with near-infrared (NIR) optimization, which is useful for detecting NIR light received from the eye, as is preferably done in some embodiments. Tunable lenses can also cover negative power ranges to be used with myopic patients. The Optotune® EL-10-30-C-NIR-LD-MV, for example, can be tuned between −1.5 and +3.5 dpt. Another example tunable lens that can be used includes the Varioptic Visayan® 80S0 electro-wetting tunable lens, which can apply variable focus (−12 to +12) and astigmatism (−6 to +0 dpt) powers.

In FIG. 1, the visual tunable lens 110 is also configured to pass the light 108 from the eye along the optical path 112 toward the wavefront sensor 116. The wavefront sensor 116 is configured to receive the light from the eye and to measure a wavefront 114 of the light 108 from the eye. The wavefront sensor 116 can be, for example, a Hartmann-Shack wavefront sensor comprising an array of lenslets having the same focal length and configured to focus light received, at various points in a cross-section of a beam of light, onto a photon sensor, which can be a CCD or CMOS array, for example. As is known and understood in the art of wavefront sensing, such a wavefront sensor produces a pattern of spots, from which a wavefront of the light being measured can be determined with high precision.

The wavefront sensor 116 provides a representation 118 of the wavefront of the light 108 to a determination module 120. The representation 118 of the wavefront can include, for example, an image in the form of pixel values for a sensor array of the wavefront sensor 116. However, in other embodiments, the wavefront sensor 116 can be configured to provide the representation 118 in other forms, such as a compressed image or a series of spot separations or spot center positions on the sensor array, for example.

The determination module 120 is configured to determine a property 122 of the eye 106 based on the measured wavefront from the sensor 116. The property 122 can include an optical property such as one or more values for aberrations of the eye, an eyeglass or contact lens prescription for the eye, objectively or subjectively determined correction parameters, accommodation amplitude or presbyoptic prescription, lensometer data for eyeglasses worn or intended to be worn by a patient, or other related data. Moreover, in some embodiments, the determination module 120 can be configured to output other data, such as a spot pattern produced by the wavefront sensor 116. Such spot patterns can be used advantageously in some embodiments to provide live images for alignment of the eye and other purposes, as described further hereinafter.

In some embodiments, the housing 102 is configured to be gripped by at least one hand of the person having the eye 106 to support a full weight of the apparatus during use. An example of such a configuration is included in FIGS. 5A-5C, for example. These embodiments can enable a person having the eye to use the apparatus 100 portably, even in the absence of a doctor, operator, or other assistance to obtain eye data such as a prescription for eyeglasses.

In some embodiments, the port 105 can include an optical window in the housing 102 or can be an opening in a modular attachment to the housing. In some embodiments, the eyecup 104, the visual tunable lens 110, and the port 105 can be physically separate. In some embodiments, port 105 can be described as a "proximal" port, and an additional "distal" port can also be provided in the housing, such that the device is "open view," enabling the eye 106 to see all the way through the apparatus 100 to an object or feature external to the apparatus 100. The apparatus 100 is monocular, in the sense that it is configured to receive one eye. However, in other embodiments, an apparatus can be binocular, as described hereinafter in connection with FIGS. 5A-5C, for example. In some binocular configurations, a second visual tunable lens can be configured to be mounted to the housing and to apply a variable focal power to light from the second eye. The second visual tunable lens can perform functions similar to those of the first visual tunable lens 110, or separate functions, as will be described further hereinafter.

In some embodiments, an apparatus can include a visual tunable lens configured to be adjusted iteratively to optimize the wavefront 114. For example, the visual tunable lens 110 can be adjusted to make the wavefront 114 as close as possible to a plane wavefront, such that aberrations produced by the eye 106 can be minimized, and the visual tunable lens 110 can simulate an eyeglass lens worn by a person having the eye 106.

In some embodiments, the eye 106 is a living eye of a person. However, in other embodiments, the eye 106 is an artificial eye that can be used for calibration purposes, for example, or for determining the prescription of a pair of eyeglasses in accordance with lensometer functions, as further described hereinafter in connection with FIGS. 5A-5C.

Figure 2:
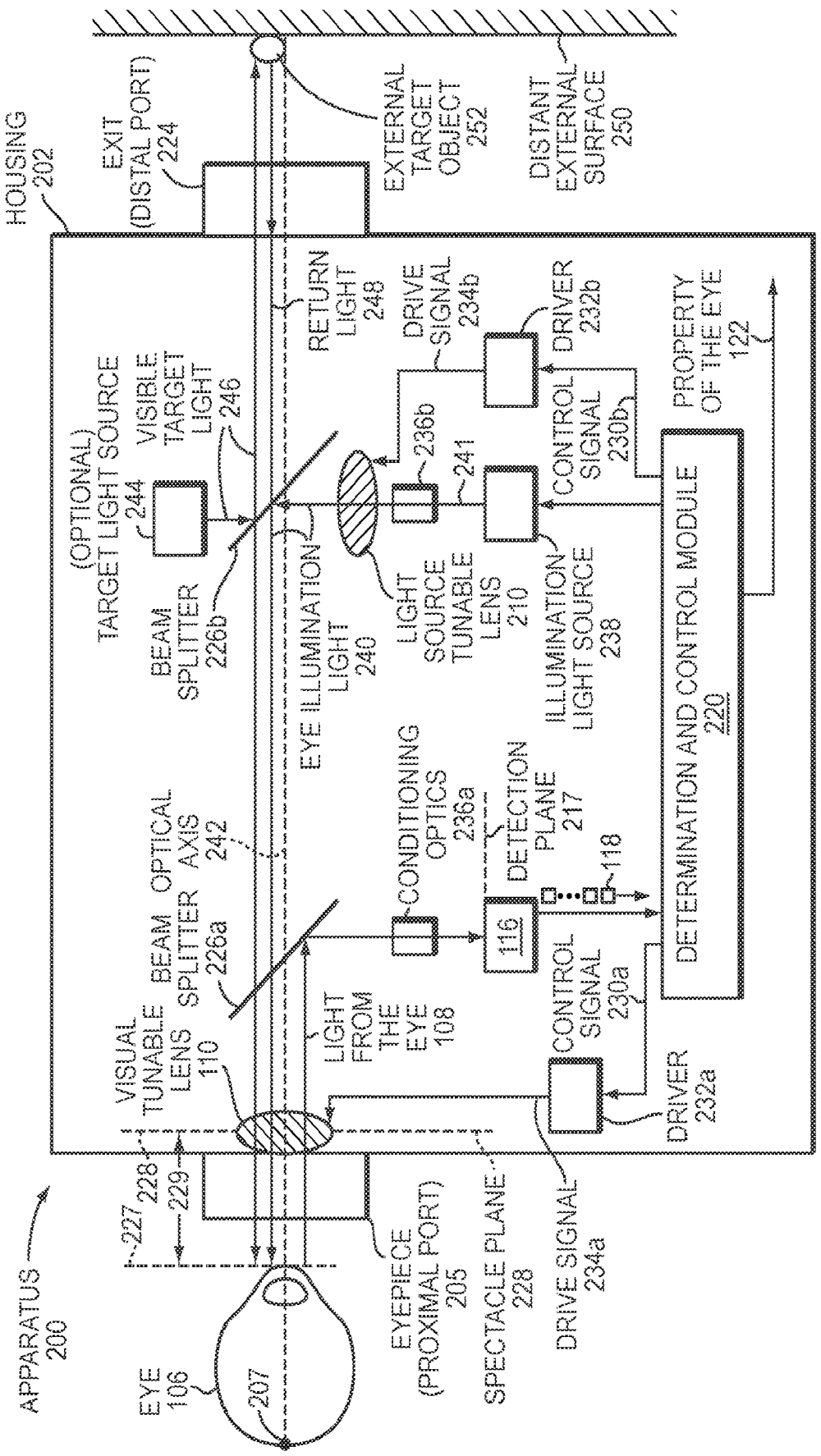
FIG. 2 (prior art) is a schematic block diagram illustrating an alternative embodiment apparatus that is open view and also includes other optional features.

FIG. 2 is a schematic block diagram illustrating an embodiment apparatus 200 that is configured to be open view and also include other optional features. Open view embodiments have the advantage that the eye 106 can view target indicia external to, and spaced away from, a housing 202 of the apparatus 200 through a visual channel between two sides of the apparatus, as further described hereinafter.

Provided an external target object 252 at a distant external surface 250, or other target indicia, are spaced away from the eye 106 at effective infinity (greater than or equal to 20 feet from the eye), the eye 106 can remain substantially unaccommodated and relaxed, such that refractive measurements performed by the apparatus 200 can be improved. It has been shown that wavefront aberrometry with a closed view configuration induces more instrument myopia (0.3 dpt) compared to an open view system (e.g., A. Cervino et al., Journal of Refractive Surgery, 2006).

The apparatus 200 is configured to have the visual tunable lens 110 mounted within close proximity to an eyepiece 205 serving as a proximal port configured to receive the light 108 from the eye 106 through the housing 202. The eyepiece 205 is detachable from the housing 202, such that it is modular and can allow the housing 202 to receive other modular attachments. Example modular attachments can include a lensometer attachment, as described hereinafter in connection with FIGS. 5A-5C, a calibration attachment, as described hereinafter in connection with FIGS. 5D-5K, or other eyepieces having different focal ranges.

As is known, different eyes can have widely varying optical aberrations and require widely varying prescriptions. A given visual tunable lens having a given tunability range, such as the Varioptic Visayan® 80S0 tunable lens described hereinabove, which has an adjustment range from −12 to +12 dpt, will be able to simulate eyeglass corrections for patients having a given range of needed correction. Thus, in some embodiments, the eyepiece 205 with the visual tunable lens 110 covering one range of corrections can be modularly replaced with another eyepiece having a different tunable lens covering a different range of corrections to address patients having a correspondingly different range of correction.

Alternatively, in some embodiments, the eyepiece 205 is configured to accommodate additional lenses and optics for various purposes. For example, the eyepiece 205 can be configured to accommodate a fixed lens, also attached to the housing, to apply a fixed focal power to the light 108 from the eye to shift a range of refractive correction measurement of the apparatus 200. Furthermore, a variety of fixed lenses having various fixed focal powers can be alternately received by the eyepiece 205, or by another portion of the housing 202, or inside the apparatus 200, for example, to address different persons with different refractive corrections. Furthermore, the eyepiece 205 can also be configured to accommodate a fogging lens or optic configured to fog the view of the eye through the apparatus 200. Fogging has the advantage that it is a non-cycloplegic (does not require cycloplegia) approach and also avoids the need for an open view system. Fogging can also be modified according to a given patient's type of refractive error (myopia or hyperopia).

Still further, the eyepiece 205 can be configured to accommodate a visual tunable lens that comprises a series of individual tunable lenses as described hereinabove in relation to FIG. 1. Using a series of individual tunable lenses instead of a single visual tunable lens, for example, may increase the range of lens powers that can be simulated by the system. A series of individual tunable lenses may also improve the dynamic range or reduce the overall optical aberrations of the system. The individual tunable lenses may be arranged (stacked) optically in series with each other, all centered on a common optical axis, for example. The individual tunable lenses may be used to cover separate larger and smaller optical correction ranges, for example. Further, individual tunable lenses in such an arrangement (stack) may be configured to address, separately, different respective optical corrections. A series of individual tunable lenses can separately address spherical power, astigmatic power (cylinder), axis of the cylindrical (astigmatic) power applied to the light, and even aberrations of higher optical order mutually independently, for example. In some embodiments, the series of individual tunable lenses can be configured to apply a spherical equivalent power, vertical Jackson cross cylinder, oblique Jackson cross cylinder, and higher-order corrections mutually independently.

As is understood in the science of refractive care, corrective lenses of eyeglasses are typically situated about 14 mm from the surface of the cornea of a patient's eye. In preferred embodiments, in order to best simulate refractive correction of eyeglasses, the visual tunable lens 110 is configured such that a plane 228 of the lens 110 is configured to be a distance 229 of about 14 mm from a front surface 227 of the cornea. Thus, the plane 228 at which the visual tunable lens 110 is situated, in this case, corresponds to the spectacle plane for the eye 106 when the proximal port has received the eye.

While a refractive measurement is being performed, the eye 106 can see light 248 from the external target object 252 located on the surface 250 at effective infinity. This open view design is facilitated by two beam splitters 226a and 226b that perform various functions within the apparatus and are also largely transparent in the visible spectrum perceived by the eye 106.

The beam splitter 226a is configured to reflect NIR light 108 received from the eye 106 toward the wavefront sensor 116. The optical path between the beam splitter 226a and the wavefront sensor 116 also includes various conditioning optics 236a. The conditioning optics 236a can include, for example, a beam aperture/iris, a narrowband optical filter configured to pass only NIR light of a given wavelength, an attenuation filter, etc. The conditioning optics 236a can also optionally include cross-polarizers disposed in the optical path and configured to minimize unwanted light at the wavefront sensor 116. In the case of a beam aperture, light from the eye illumination light source can be restricted by the aperture, and example aperture sizes may range between about 50 μm and about 500 μm.

The wavefront sensor 116 provides the wavefront representation 118 to a determination and control module 220, which is configured to determine the property 122 of the eye. The determination and control module 220 performs functions similar to those of determination module 120 in FIG. 1, but the module 220 also includes control functions. In particular, the control module 220 outputs a control signal 230a to a lens driver 232a, which outputs a drive signal 234a to the visual tunable lens 110 to set the lens 110 to the appropriate focal power. With appropriate logic in the determination and control module 220, this forms a closed-loop system (circuit), wherein the wavefront representation 118 can be continuously monitored, and wherein the control module 220 can provide appropriate control signals 230a to update the setting of the visual tunable lens 110 continuously. This process can be iterative to minimize wavefront errors of the eye 106 using the visual tunable lens 110. In this manner, the variable focal power of the visual tunable lens may be adjusted iteratively in response to successive wavefront measurements in order to minimize a wavefront error of the light from the eye. Various iterative processes are further described hereinafter in connection with FIGS. 6 and 10A-10B, for example.

The apparatus 200 also includes an illumination light source 238 that is configured to output NIR light (eye illumination light 240) toward the eye. In other embodiments, the eye illumination light and light received from the eye may be visible or infrared. The illumination light 240 is reflected by the beam splitter 226b, passes through the beam splitter 226a, and exits the proximal port 205 through the visual tunable lens 110 to enter the eye 106. The light 240 is intended to form a focused spot 207 at the retina of the eye 106. A portion of the eye illumination light 240 is reflected and scattered by the eye 106 and is received as light 108 from the eye to be detected at the wavefront sensor 116.

When the eye illumination light 240 passes through the visual tunable lens 110, its convergence or divergence is affected by the setting of the tunable lens 110. In order to maintain a focused spot 207 at the retina, the apparatus 200 includes a light source tunable lens 200 that applies variable focal power to the eye illumination light 240 to maintain the focused spot 207 at the retina. Thus, when the determination and control module 220 adjusts the focal power of the visual tunable lens 110, the light source tunable lens 210 can be adjusted to a corresponding value that affects only the eye illumination light 240 and maintains the focused spot 207. As will be understood by those skilled in the art of optics, the corresponding settings between the visual tunable lens and the light source tunable lens 210 can be pre-calibrated such that an appropriate setting for the lens 210 can be known for every setting of the tunable lens 110. In order to make these corresponding adjustments, the determination and control module 220 can store calibration data or receive the calibration data from another source, such as memory illustrated in FIG. 4, to make the appropriate corresponding settings.

In cases in which the visual tunable lens 110 can correct over the refractive error range needed for a given patient, corresponding adjustments to the light source tunable lens 210 may not be required. However, the light source tunable lens 210 can be used to extend the range of measurement for a given visual tunable lens 110 by reducing spot size of illumination light focused onto the retina of the eye, particularly in case the eye has a refractive error greater in magnitude than the maximum refractive error that can be corrected with the visual tunable lens 110. Furthermore, the light source tunable lens 110 can be used to expedite analysis of a patient's eye and determination of a corresponding prescription by sweeping the range before, during, or after tuning the visual tunable lens. For example, if a particular visual tunable lens cannot be tuned as fast as desired for a given set of refractive measurements, then the optical power of the light source tunable lens may be adjusted, in parallel with the optical power of the visual tunable lens, to achieve a particular combined power setting more quickly. Moreover, the light source tunable lens 210 can be used to reduce speckle, as described further hereinafter.

In order to control the light source tunable lens 210 in FIG. 2, the determination and control module 220 outputs a control signal 230b to a lens driver 232b. The driver 232b outputs a drive signal 234b to the light source tunable lens 210 to make the appropriate setting. Preferably, where the visual tunable lens 110 controls sphere, cylinder, and axis independently, the light source tunable lens 210 includes similar, independent adjustments such that the eye illumination light can remain focused on the retina for all visual tunable lens settings.

The optical path between the illumination light source 238 and the beam splitter 226b also includes conditioning optics 236b. The optics 236b can include some functions similar to those of the conditioning optics 236a. For example, the optics 236b can include a narrowband filter configured to pass only light of wavelengths corresponding to the illumination light source 238. The optics 236*b* can also include an iris (aperture) configured to adjust diameter of the eye illumination light 240 or a diaphragm to define the illumination light and to align the light 240 with the beam splitter 226*b*. The illumination light source 238 can be a light emitting diode (LED), but it can also be a diode laser or other collimated, coherent (or semi-coherent, such as a superluminescent diode) light source, for example.

As will be understood by those skilled in the art of optics, a coherent illumination light source 238, such as a laser, can produce some degree of speckle pattern at the eye 106 and at the wavefront sensor 116, depending on the degree of coherence of the light source 238. Random speckle patterns with high contrast may, therefore, be present in a spot diagram produced using the wavefront sensor. These speckle patterns can interfere with the ability of the wavefront sensor 116 to distinguish sensitively between laser speckle and the spot pattern that defines the wavefront of the light 108. Speckle contrast can reduce the accuracy of localizing each spot in a detected spot diagram, which, in, turn can reduce the accuracy of a wavefront that is reconstructed using the detected spot diagram.

One advantage of embodiments is that the determination and control module 220 can be configured to dither (i.e., rapidly apply variable focal power or adjust another refractive setting of) either the visual tunable lens 110, the light source tunable lens 210, or both tunable lenses slightly while spot diagrams are being acquired by the wavefront sensor. In the case of the light source tunable lens being dithered, variable focal power is applied to the light 241 from the light source 210. This dithering can randomize the speckle pattern produced by the eye illumination light 240 at the eye 106, or, equivalently, randomize a speckle pattern produced by the light 108 from the eye at the wavefront sensor 116. This dithering, as described in connection with FIG. 9B, for example, can introduce small variations into the wavefront of the light to randomize the speckle pattern generated at the eye by an eye illumination light source and received at the wavefront sensor.

Such dithering can reduce or eliminate the effects of laser speckle pattern that would otherwise diminish measurement sensitivity of the wavefront sensor 116. If the magnitude of the dithering is sufficiently large, the speckle pattern will be randomized over the course of an acquisition. If the speckle pattern is sufficiently randomized over the course of a single exposure, an averaged-out speckle pattern will be captured. This implies that the spots in the spot diagram can be more accurately localized due to the reduced speckle contrast. Furthermore, a dithering magnitude that is sufficiently large to randomize the speckle pattern can also be small enough to have no appreciable impact on the size of the focal spot 207 or the accuracy of the wavefront measurements. An example spherical dithering magnitude includes, for example, +/−0.01 dpt. However, other example spherical dithering magnitudes are much greater, such as in a range of 0.25-0.5 dpt, for example. Other tunable lens parameters, such as cylinder power, axis, higher order parameters, or parameters such as spherical equivalent power in other known basis sets, for example, may be dithered as an alternative to, or in addition to, dithering sphere. Thus, the ability to eliminate or reduce laser speckle noise is yet another advantage of tunable lenses used in embodiment apparatus and methods.

The apparatus 200 also includes an optional target light source 244 mounted to the housing 202. FIG. 2 illustrates the target light source mounted inside the housing 202, but other embodiments can include outside mounting. The target light source 244 is configured to output visible target light 246, which is reflected by the beam splitter 226*b* and output from the apparatus 200 through a distal port 224 in the housing. Together, the proximal and distal ports form a visual channel parallel to the optical axis 242 through which the eye 106 can see the external target 252. The visible target light 246 creates a spot or other indicia on the distant external surface 250 external to and spaced away from the housing 202. The spot or other indicia can be viewed by the eye 106 to cause the eye to be unaccommodated, with the distant external surface 250 at effective infinity from the eye. The visible target light 246 is reflected or scattered from the surface 250, and a portion returns to the eye 106 as return light 248 through the apparatus 200. However, in other embodiments, the target light source 244 is not used. Instead, the return light 248 viewed by the eye 106 is ambient light scattered or reflected from the external target object 252 and through the apparatus 200.

In the schematic block diagram illustrated in FIG. 2, the light 108 from the eye, visible target light 246, return light 248, and eye illumination light 240 are shown as being offset from the optical axis 242 of the eye. This depiction is for convenience in illustration only, and all of these light beams can be mutually coincident, collinear, and centered on the optical axis 242.

However, in preferred embodiments, the eye illumination light 240 exiting the port 205, and the light 108 from the eye entering the port and received by the tunable lens 110, are non-collinear. This non-collinear orientation can reduce or eliminate eye illumination light 240 that is back-reflected from the surface of the cornea of the eye from being received at the wavefront sensor. This can be very helpful in reducing noise and increasing signal-to-noise ratio for wavefront signals detected by the wavefront sensor.

In conformity with the principle of making the light entering the eye non-collinear with the light exiting the eye, various adjustments can be made to the optical configuration in FIG. 2. For example, a detection plane 217 of the wavefront sensor 116 can be non-perpendicular to an illumination axis 241 of the illumination light source 238. The wavefront sensor 116 can be slightly non-parallel with the optical axis 242 of the eye. In other words, the detection plane 217 of the wavefront sensor can be non-parallel with an illumination axis of the eye illumination light 240 within an optical path between the beam splitter 226*b* and the eye 106, and the detection plane 217 can be non-perpendicular with an axis of illumination of the eye illumination light 240 within an optical path between the eye illumination light source 238 and the beamsplitter 226*b*.

Figure 3:
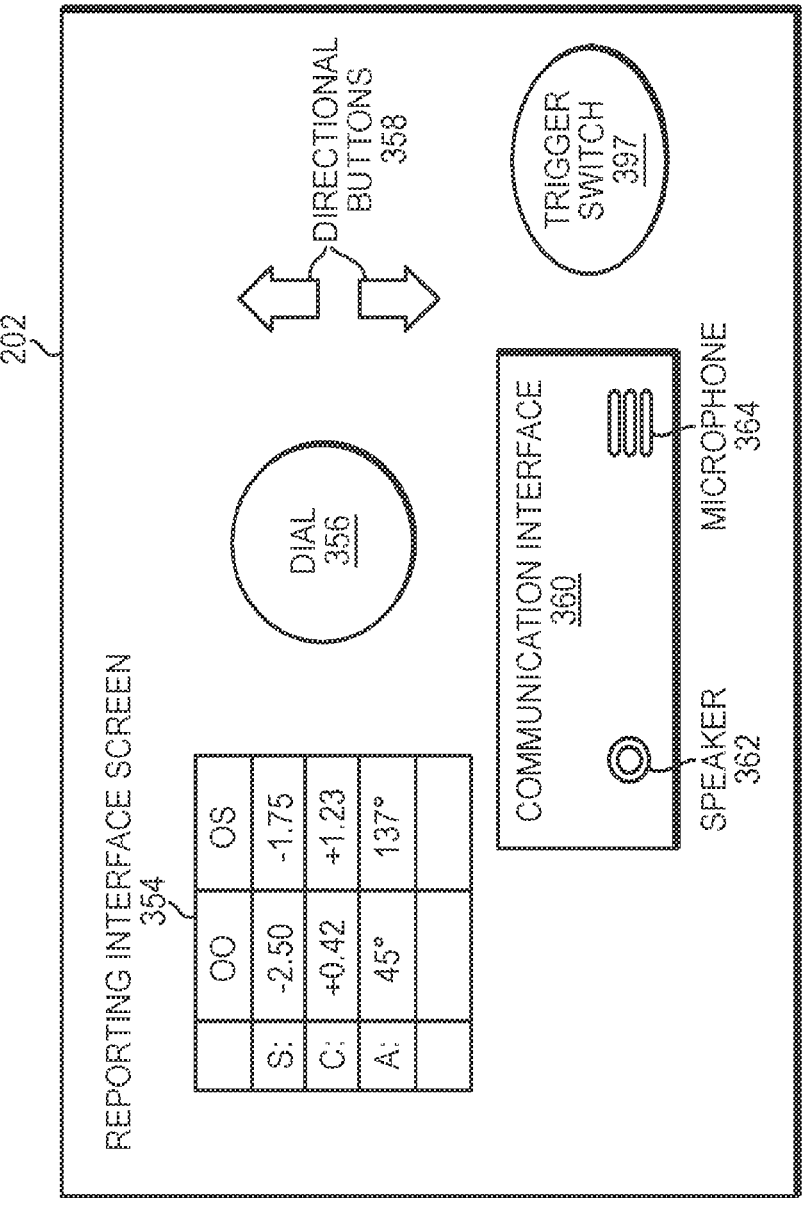
FIG. 3 (prior art) is a schematic diagram illustrating various optional input and output features of embodiment devices, such as those illustrated in FIGS. 1-2.
Figure 4:
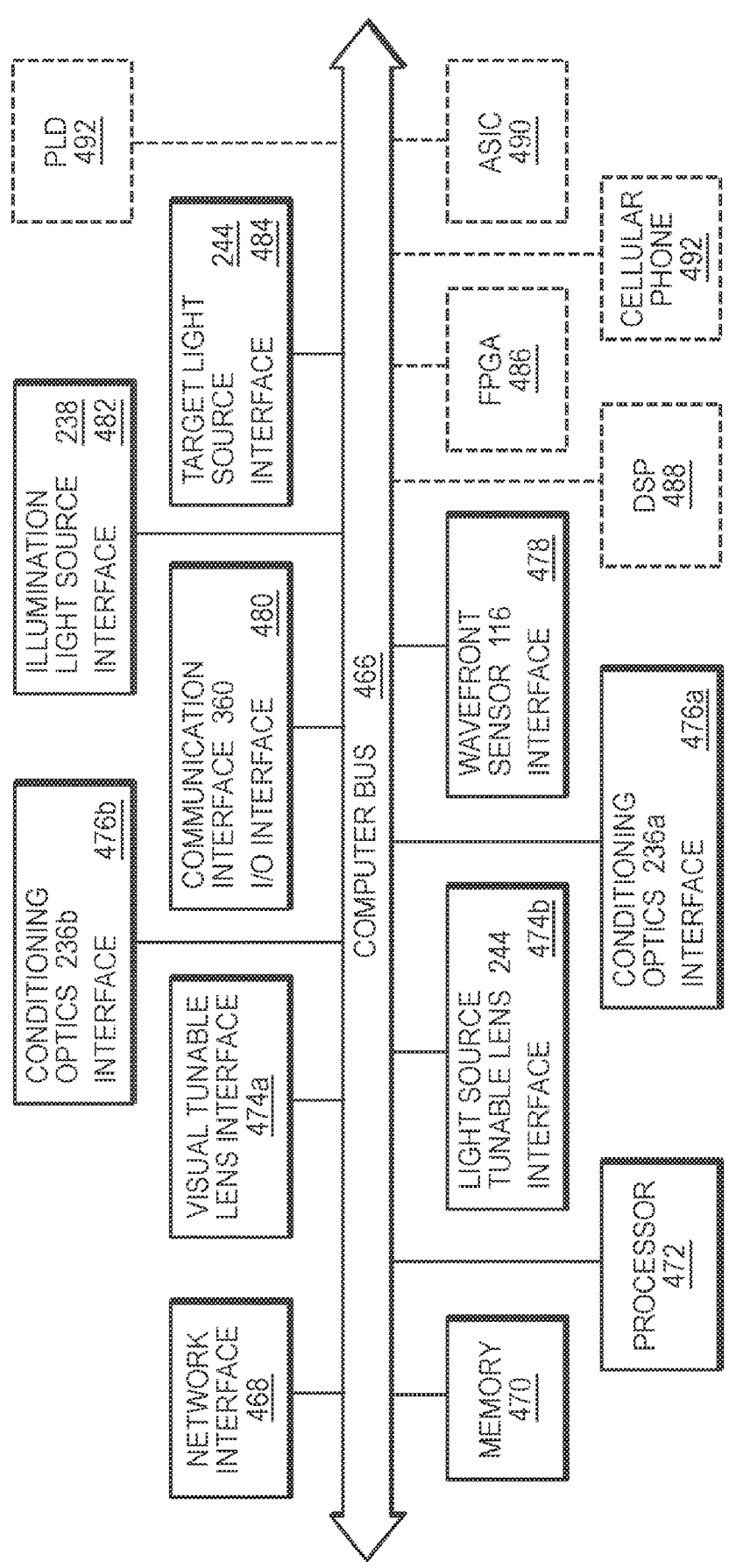
FIG. 4 (prior art) is a computer interconnect diagram illustrating various components of the determination and control module in FIG. 2 and its connections to various components, including some components illustrated in FIG. 2, some optional components shown in FIG. 3, as well as some that are not illustrated in FIGS. 2-3.

FIG. 3 is a schematic diagram illustrating various optional input and output features of embodiment devices, such as those illustrated in FIGS. 1 and 2. In particular, the housing 202 of the apparatus 200 illustrated in FIG. 2 can include a reporting interface screen 354, a dial 356, a communication interface 360, directional buttons 358, and a trigger switch 397. The dial, directional buttons, and trigger switch are examples of manual controls that can be configured to be adjustable by an eye patient, or by a clinician, to adjust the variable focal power of the visual tunable lens in accordance with a subjective refractive preference of the eye patient. In other embodiments, these inputs and outputs are provided by peripheral devices in operational communication with the apparatus 200. Examples of peripheral devices, can include a cellular phone, as illustrated in FIG. 4, or a separate, handheld, wired or wirelessly connected controller that a clinician, patient or other user can use to specify inputs or receive outputs, for example.

Figure 5A:
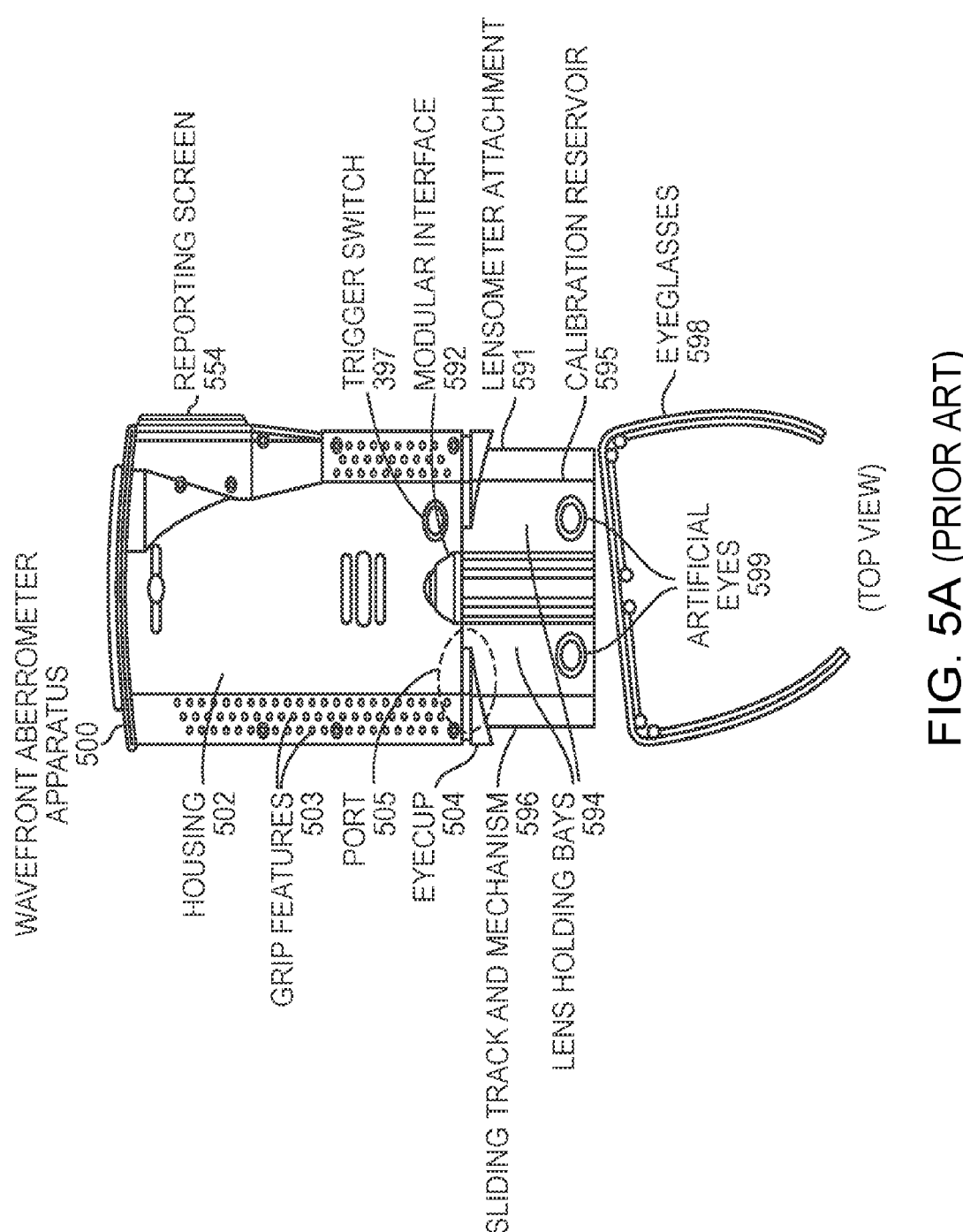
FIG. 5A (prior art) is a top-view illustration of an embodiment, binocular, wavefront aberrometer autorefractor apparatus with a lensometer module attached; the apparatus of FIG. 5A is also referred to as "QuickSee" apparatus herein).
Figures 5B, 5C:
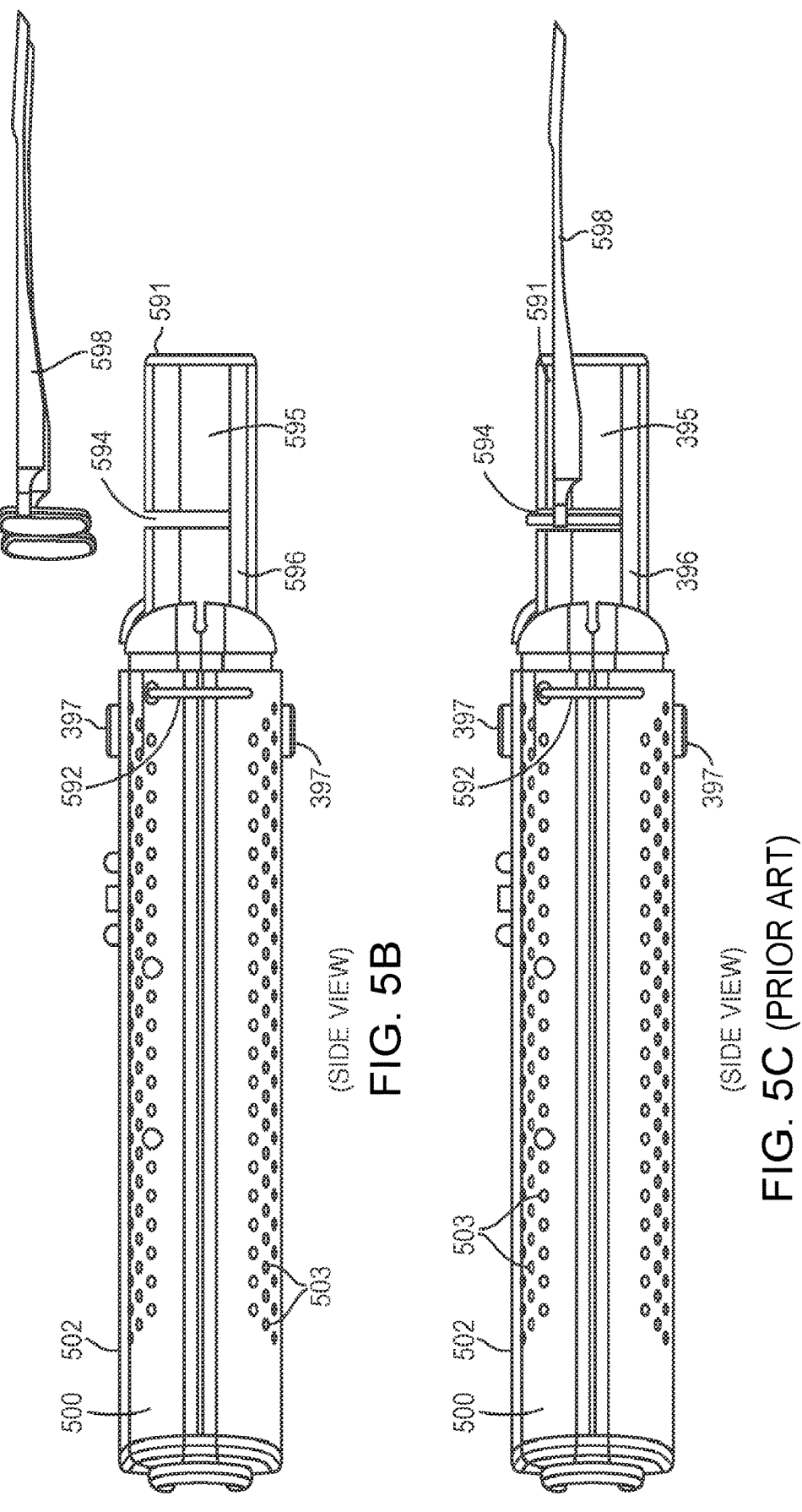
FIGS. 5B-5C (prior art) are side-view illustrations of the apparatus illustrated in FIG. 5A.

The reporting interface 354 can be an LCD screen, for example, on the housing 202 that can be read by a user to obtain a prescription for eyeglasses, as illustrated, or another property of the eye 106. The reporting interface screen 354 provides sphere (S), cylinder (C), and axis (A) measurements for right (OD) and left (OS) eyes after measurements are completed. Various other information can also be presented to a user or operator using the reporting interface screen 354, such as information about higher order aberrations, Zernike polynomial parameters measured for the right and left eyes, a contact lens prescription, alignment information, and other information. As another example, the reporting interface screen 354 can show a live image produced by the wavefront sensor 116 in FIG. 2 to assist with calibration of the apparatus or for eye alignment purposes for initial setup, for example. Further alternative information that can be provided by the reporting interface screen 354 includes static images produced by the wavefront sensor 116, other information representative of the wavefront detected, calibration instructions, operating instructions, etc. Furthermore, in some embodiments, the reporting interface screen 354 is a touchscreen enabling a user to input information, such as selecting a measurement to be performed. Actual placement of the features shown in FIG. 3 onto a device housing or peripheral module may vary in various embodiments. An example placement of the trigger switch 397 is illustrated in FIGS. 5A-5C.

The communication interface 360 includes a speaker 362 configured to provide audible instructions to a user, such as instructions for how to align the eye to an input port of the housing for best measurement accuracy. In some embodiments, the speaker 362 provides step-by-step instructions to the user before and during a measurement of the eye. The interface 360 also includes a microphone 364 that can be used to receive inputs from the user, such as a refractive preference of the user. This feature is particularly useful when the apparatus 200 operates in phoropter mode, as will be described further hereinafter in connection with FIGS. 8A-8B, for example. Thus, the speaker 362 can provide certain instructions such as "tell me which lens setting is best, one or two." The apparatus 200 illustrated in FIG. 2 can then set the visual tunable lens to two different settings, one subsequent to the other, and the speaker 362 can indicate which setting is 1 in which setting is 2. A user can then speak, through the microphone 364, "one" or "two" to indicate which setting of the visual tunable lens 110, simulating an eyeglass correction, is preferable to the user, who is the person whose eye 106 is being measured.

As an alternative to the verbal communication just described for specifying subjective preferences, the directional buttons 358 can be pressed by a user to specify which visual tunable lens 110 setting is preferable. For example, the wavefront sensor 116 can be used to determine an objective refractive correction for the user. The visual tunable lens 110 can then be set to simulate a corrective lens applied to the eye 106. The user can then be given the opportunity to specify various changes to refractive settings of the visual tunable lens 110, using the directional buttons 358, in accordance with a subjective preference. This range of adjustment can be a fine adjustment over a relatively small range, such as a spherical correction adjustment range of +/−0.25-0.50 dpt. Once the user has specified spherical correction to the subjective preference, the buttons 358 can then be used to optimize cylinder and axis in turn according to subjective preferences, in a similar fashion. After the visual tunable lens 110 is set to all the preferred settings for sphere, cylinder, and axis, the process can be repeated iteratively for greater precision or to evaluate repeatability of subjective preference settings.

The dial 356 can be used as an alternative to the directional buttons 358. For example, the user can turn the dial 356 to adjust the spherical correction over the limited range of +/−0.25 dpt or +/−0.50 dpt, for example. The dial 356 can be preferable to the directional buttons 358 since rotational motion of the dial 356 can be smoother and cause less disturbance to the housing 202 than pressing buttons. The dial 356 may also be easier to use for other reasons, such as the user's ability to turn the dial 356 quickly or slowly, in accordance with the user's preference and the degree of adjustment required.

The trigger switch 397 provides another means of input by the user to the apparatus. In particular, as further described hereinafter in connection with FIG. 5A and FIGS. 8A-8B, for example, the trigger switch 397 can be pressed by the user when the user is ready for a measurement to occur, and then the user can release the trigger switch 397 once a simulated refractive correction provided by the visual tunable lens 110 operating in closed-loop fashion with the wavefront sensor is completely satisfactory. An example location for the trigger switch 397 is shown on the embodiment device illustrated in FIG. 5A.

FIG. 4 is a computer interconnect diagram illustrating various components of the determination and control module 220 in FIG. 2 and its connections to various components, including some internal components shown in FIG. 2 and other optional components shown in FIG. 3, as well as some other optional components that are not illustrated in FIGS. 2-3. In the apparatus embodiment illustrated in FIG. 2, the determination and control module 220 performs all necessary computing and control functions for the apparatus 200. It should be noted that in other embodiments, these functions can be distributed between a determination and control module and other processors or controllers, as will be understood by those skilled in electrical and computer engineering.

The determination and control module 220 includes a computer bus 466 used as an interconnect for various components. The module 220 includes memory 470 and a processor 472 that are used to store data and program instructions and perform necessary processing functions, processing functions can include determining the property of the eye, such as optical properties including a refractive correction prescription to be applied to the eye, based on the measured wavefront, the tunable lens setting, and any objective preference information obtained. The representations 118 of the wavefront entering the module 220 in FIG. 2 can be stored in the memory 470 for analysis by the processor 472. The module 220 also includes a network interface 468 coupled to the computer bus 466 for communicating with outside computers or networks if desirable. The network interface 468 can be used to report refractive results to an external computer or network for eyeglass ordering purposes, for example, or allow the functioning of the apparatus 200 to be monitored by an external or even remote computer, for example.

The processor 472 is coupled to a visual tunable lens interface 474a that controls the driver 232a illustrated in FIG. 2. Thus, through the visual tunable lens interface 474a, the processor 472 can control the settings for the visual tunable lens 110. In a similar fashion, the processor 472 is coupled to a light source tunable lens interface 474b for control of the light source tunable lens 210 illustrated in FIG. 2. It should be understood that, where either the visual tunable lens 110 or the light source tunable lens 210 includes a series of individual tunable lenses, as described herein-above in relation to FIG. 1, either interface 474a or 474b may correspondingly include a series of individual inter-faces for mutually independent control of the respective, individual tunable lenses.

The module 220 also includes interfaces 476a and 476b to control the conditioning optics 236a and 236b, respectively. The interfaces 476a-b are particularly useful in cases in which the conditioning optics are adjustable. For example, the conditioning optics 236a-b can include such features as variable attenuation and adjustable diaphragms and irises for beam conditioning.

The module 220 also includes a wavefront sensor inter-face 478 for receiving data from the wavefront sensor 116 in FIG. 2. A communication interface 480 in the module 220 allows the module 220 to communicate data to and from the communication interface 360 illustrated in FIG. 3. While not shown in FIG. 4, other interfaces can be provided in the determination and control module 220 for sending data to, and receiving data from, the reporting interface screen 354, dial 356, directional buttons 358, and trigger switch 397, which are illustrated in FIG. 3. Interfaces 482 and 484 are also included in the module 220 for controlling the illumi-nation light source 238 and the target light source 244, respectively, which are illustrated in FIG. 2. For example, these light sources may be turned off when not in use, and their intensity may also be adjustable in certain embodi-ments.

The network interface 468 can include a wired or wireless interface, such as a universal serial bus (USB) interface, a wired Ethernet interface, a bluetooth communication mod-ule, a wireless infrared (IR) interface, a wireless local area network (WLAN) interface, or a wireless cellular data interface. Through such example interfaces, the processor 472 can communicate with an external or remote device that is outfitted with a similar communication interface. Such an interface can be used to print eye measurement results, store results on a thumb drive or other storage medium, send measurement results to a personal computer, cellular phone, smart phone, or cloud-based server, send prescription orders for eyeglass or contact lens prescriptions via any of these or other known means, communicate in other ways, or provide other output data. In one example, objective refraction results, subjective refraction results, lensometry results, accommodation measurements, another eye property, machine learning results, or a combination thereof, as deter-mined by any one or more of the procedures illustrated in FIGS. 7, 8, 9A, 9C-9F, and 10A-10B, may be communicated directly or indirectly to a desired location or device with the network interface 468 being configured appropriately.

One or more of the interfaces illustrated in FIG. 4 can be replaced or have its functions augmented by a suitably programmed device, such as an optional field-programmable gate array (FPGA) 486 or a digital signal processor (DSP) 488. Furthermore, an application-specific integrated circuit (ASIC) 490 or programmable logic device (PLD) 492 can also be used.

As also illustrated in FIG. 4, the module 220 can include an interface used to communicate with a cellular phone 492. In some embodiments, the cellular phone can be configured to be attached to the housing 202 or can be otherwise programmed to perform some of the functions described in connection with FIG. 2 for the determination and control module 220. Furthermore, in some embodiments, the cellu-lar phone 492 is used to display a representation of the wavefront of the light from the eye. Such a representation can be used for alignment of the eye to the apparatus 200 or for other subjective or objective analytical purposes, for example. In some embodiments, the cellular phone 492 can be used to perform the functions of the reporting interface screen 354 shown in FIG. 3, as well as other input or output functions of the dial 356, communication interface 360, directional buttons 358, or trigger switch 397. Furthermore, in some embodiments, the cellular phone can be used as a Hartmann-Shack wavefront sensor. For example, a standard multi-pixel sensor array on the cellular phone that is used to acquire photographs can be adapted to perform the functions of the light sensor array of the Hartmann-Shack wavefront sensor, and a separate lenslet array can be used to focus the light 108 received from the eye onto the sensor array. In some embodiments, the cellular phone includes two multi-pixel sensor arrays that are used as respective Hartmann-Shack wavefront sensors for respective eyes of a patient. Further, a first one of the two sensor arrays may be used as a wavefront sensor, while a second one of the two sensor arrays may be used to perform one or more of pupil measurements, keratometry, iris imaging, or other known ophthalmic imaging functions.

FIG. 5A is a top-view illustration of an embodiment, binocular, wavefront aberrometer apparatus 500. The appa-ratus 500 is particularly configured to enable not only wavefront aberrometer measurements using the visual tun-able lens 110 as illustrated in FIG. 2, but also to enable lensometer measurement functions. The apparatus 500 includes a housing 502, which includes grip features 503 configured to be gripped by at least one hand of a person having the eye 106 to support a full weight of the apparatus 500 during use.

Connected to the housing 502 is an eyecup 504 configured to provide mechanical registration of the apparatus 500 against a forehead and cheek of a person (user, patient) having the eye 106. A port 505 in the housing is configured to receive the eye 106 and to receive light from the eye, as described in connection with FIG. 2. The trigger switch 397 is mounted to the housing 502 as illustrated in FIG. 5A. The switch 397 performs the functions as described in connec-tion with FIG. 3. In particular, when a user is ready for the apparatus 500 to perform a measurement, the user presses the trigger switch 397. After the trigger switch is pressed, successive wavefront measurements are obtained by the wavefront sensor 116 illustrated in FIG. 2, and the determi-nation and control module 220 adjusts the visual tunable lens 110 to simulate eyeglass correction.

Each time the visual tunable lens 110 is adjusted, the light source tunable lens 210 can be adjusted by a compensating amount to cause the eye illumination light 240 to form a focused spot 207 at the retina of the eye 106. These adjustments can be performed iteratively, as further illus-trated hereinafter in connection with FIG. 6, until the user is satisfied with the simulated refractive correction. Once the user is satisfied, the user can again press the trigger switch 397 to indicate that the correction is satisfactory. In other embodiments, the user or a technician or other person assisting can press and hold a trigger switch while iterative adjustments are performed, and release of the trigger switch can indicate that a user is satisfied with the correction.

The apparatus 500 also includes reporting screen 554 that is configured to display a lens prescription intended for the patient (user). In various embodiments, the reporting screen 554 can be configured to display a contact lens prescription, a wavefront spot pattern for alignment or other purposes, or other information described in connection with the reporting interface screen 354 illustrated in FIG. 3, for example.

FIG. 5A also shows a lensometer attachment 591, modularly attached to the apparatus 500 via a modular interface 592, for performing lensometer measurements for eyeglasses 598. The housing 502 is thus configured to receive a lensometer attachment 591 that is configured to receive and support a corrective lens intended to be worn by a person. The lensometer attachment 591 can also be configured to support a lens blank that is intended to be manufactured into a corrective lens; in this way, the lensometer attachment 591 is useful for both lensometer measurements in a clinical setting and for analysis of lenses and lens blanks during a lens manufacturing process. The wavefront sensor can measure the wavefront of the light received through the corrective lens or lens blank. A determination module, such as module 120 in FIG. 1 or module 220 in FIG. 2, can be configured to determine a refractive property of the corrective lens or lens blank based on a lens wavefront of light received through the corrective lens or lens blank.

In FIG. 5A, the lensometer attachment 591 includes lens holding bays 594 for placement of the pair of eyeglasses 598, with each lens in its own isolated bay. A calibration reservoir 595 including artificial eyes (model eyes) 599 is also included in the attachment 591 for aligning two optical components of known optical wavefront properties to two respective optical channels in the apparatus 500. The calibration reservoir 595 may also be referred to as calibration holder or calibration bay.

The attachment 591 in FIG. 5A also includes a sliding track and mechanism 596 between the modular interface 592 and the calibration reservoir 595 to clamp the optical components of the eyeglasses 598 in a manner to minimize movement and stabilize the eyeglasses for lensometer measurements. The sliding track and mechanism 596 can be used to set a distance between the two channels of the binocular apparatus 500. When the apparatus 500 is used to determine a refractive correction for someone's eye, the sliding track and mechanism 596 can be used to adjust the binocular apparatus 500 to match the interpupillary distance (i.e., the distance between the eyes of the user). When the apparatus 500 is used for lensometry on a pair of eyeglasses, then the sliding track and mechanism 596 can be used to match the binocular apparatus 500 to a distance between respective optical centers of the two lenses of the eyeglasses. The trigger switch 397 also causes the apparatus 500 to trigger a lensometer measurement through the initiation of a software calibration sequence.

The artificial eyes 599 are shown included in the calibration reservoir 595 for calibration purposes. The artificial eyes 599 can act as known aberrations so that aberrations due to the eyeglasses can be determined. The lensometer attachment 591 can be similar in some of its internal structure to a calibration cradle 517 described further hereinafter in connection with FIGS. 5D-5K. In particular, there can be reservoirs in which to hold the artificial eyes and slots in which eyeglass lenses can be placed.

The tunable lens 110, which is used in the apparatus 500 for eye measurement purposes as further described herein, can be optionally used or removed from the apparatus for lensometer purposes. Where the tunable lens 110 is used, it can be held at a fixed optical power so as to shift the measuring range of the apparatus 500 in case the eyeglass lens being measured fall outside the base range of the apparatus.

Figures 5D, 5E:
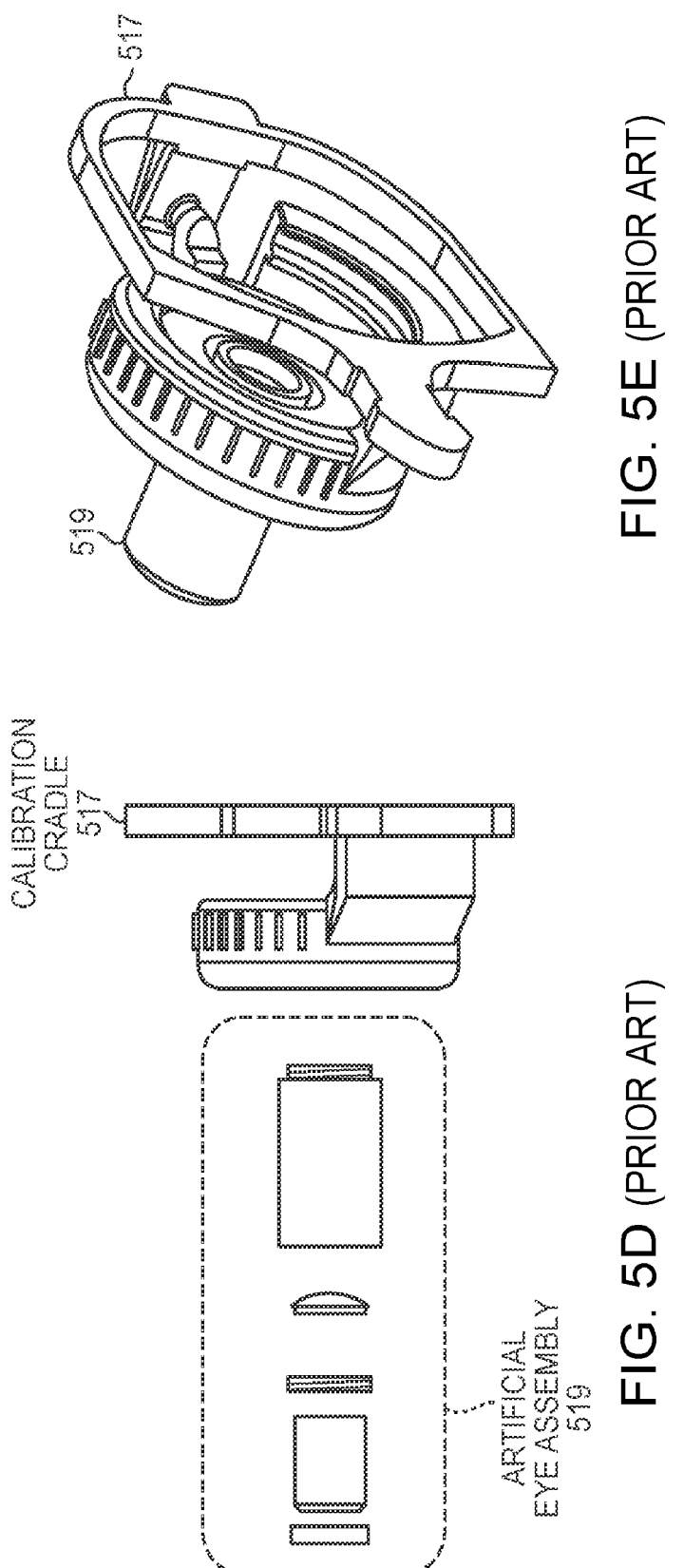
FIG. 5D (prior art) is an exploded, side-view illustration of a calibration cradle and artificial eye that can be used to calibrate the apparatus illustrated in FIGS. 5A-5C.
FIG. 5E (prior art) is a perspective view of the calibration cradle illustrated in FIG. 5D, with the artificial eye assembly attached thereto.

FIGS. 5B-5C are side-view illustrations of the apparatus 500 illustrated in FIG. 5A. In particular, FIG. 5D shows the eyeglasses 598 outside of the lensometer attachment 591, while FIG. 5C shows the eyeglasses 598 inserted into the lensometer attachment. These side-view illustrations also show that the apparatus 500 includes a second trigger switch 397 at the bottom side of the housing 502.

It will be noted from FIG. 5A that the apparatus 500 is binocular in design. In some binocular embodiments, both sides of the apparatus, addressing opposite eyes of a person using the apparatus, are designed to include optical elements similar to those illustrated in FIG. 2. In this way, measurements can be obtained for both eyes of a person using the apparatus at the same time. Embodiment apparatuses similar to that described in connection with FIGS. 5A-5C can simplify alignment of both eyes simultaneously with respective sides of the apparatus.

However, in the embodiment illustrated in FIGS. 5A-5C, one side of the apparatus 500 is configured to perform wavefront aberrometry measurements of the eye or eyeglass lens placed in front of the port 505, while the other side of the apparatus 500 is configured to have the same light transmission characteristics as the measurement-optical channel, but can otherwise be passive and see-through (i.e., open view). This can ensure that the user has a similar view through both eyes, instead of having the view of one eye brighter than the view of the other eye, for example. Thus, in order to perform both measurements on both eyes using the apparatus 500, the apparatus can be rotated 180° to address opposite eyes of a person using the apparatus 500, and opposite lenses of eyeglasses when used in lensometer mode, each eye or eyeglass in turn. Such open-view, binocular embodiments can permit the viewing conditions of both eyes to be similar to each other. This is in contrast to existing small wavefront aberrometers that are neither open view nor binocular, which makes the viewing conditions of the patient's two eyes different, which can negatively affect binocular subjective refraction (natural viewing).

FIG. 5D is a side-view illustration of the calibration cradle 517, referenced hereinabove, which can be used to calibrate the apparatus 500 illustrated in FIGS. 5A-5C. The calibration cradle is configured to be modularly attached to the housing 502, particularly to the eyecup 504 to obtain a reference wavefront measurement for a perfect eye in the absence of refractive correction from eyeglasses or the aberrations due to a living eye. An artificial eye assembly 519 can be mechanically attached to the calibration cradle 517 to fulfill this purpose.

FIG. 5E is a perspective view of the calibration cradle 517 with the artificial eye assembly 519 attached thereto.

Figures 5F, 5G, 5H, 5I, 5J, 5K:
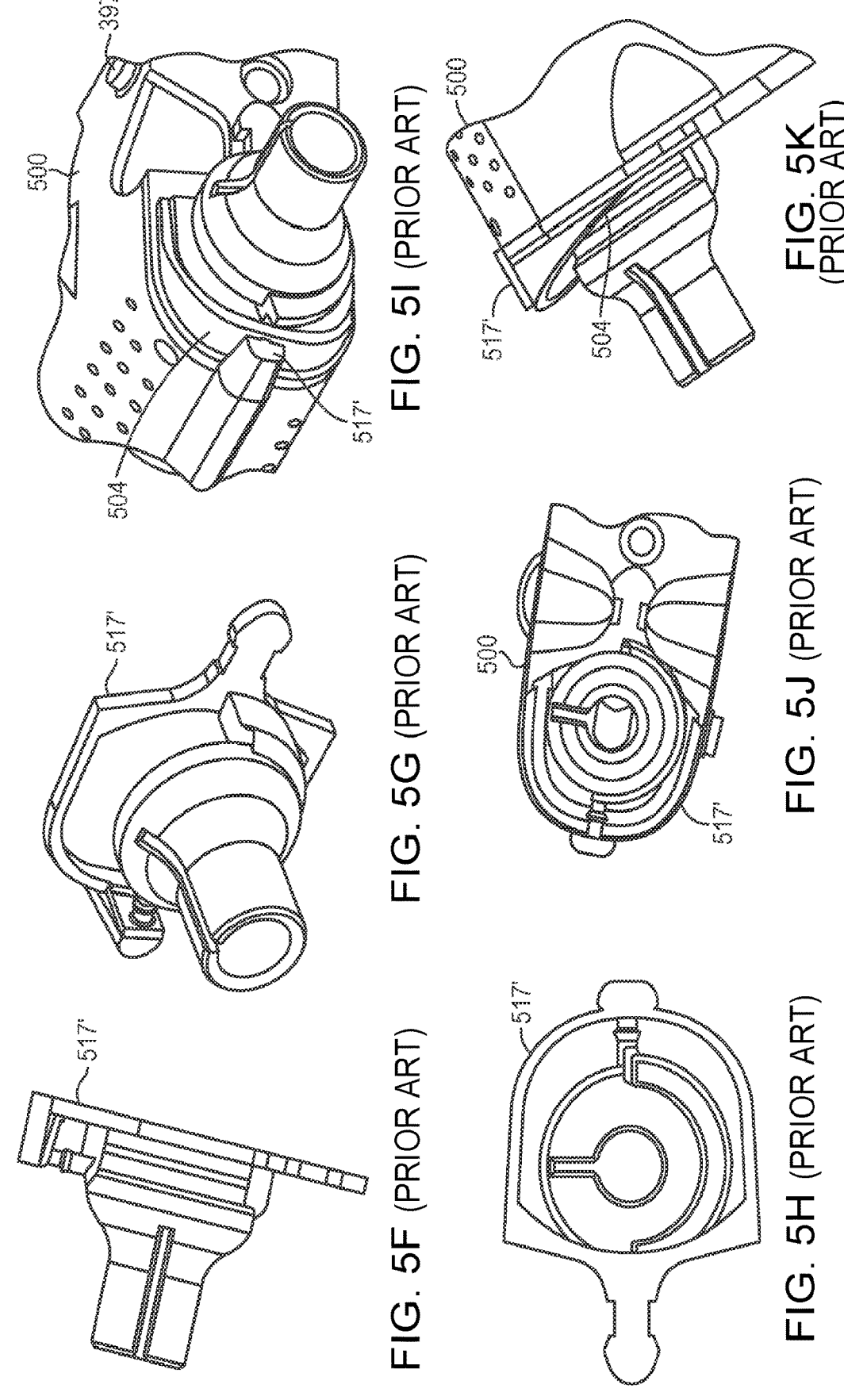
FIGS. 5F-5K (prior art) are various illustrations of a calibration cradle assembly similar to that shown in FIGS. 5D-5E.

FIGS. 5F-5K are various illustrations of a calibration cradle 517' similar to the calibration cradle 517 illustrated in FIGS. 5E-5F. The calibration cradle 517' is assembled with the artificial eye assembly 519. In particular, FIG. 5F is a side-view illustration of the assembly, FIG. 5G is a perspective view of the assembly, and FIG. 5H is an end-view illustration of the cradle 519. FIGS. 5I, 5J and 5K are various illustrations showing the calibration cradle 517' attached to the apparatus 500.

Using the calibration cradle 517 or 517' attached to the apparatus 500, the apparatus 500 can determine a lens wavefront error due to the visual tunable lens alone for calibration purposes. As is known, tunable lenses can have lower optical quality than fixed lenses. Thus, with a living eye absent, the artificial eye assembly 519 in place with the calibration cradle 517 or 517', and the artificial eye assembly 519 having known optical characteristics, and preferably characteristics as close as possible to those of a perfect eye, resulting in no wavefront error to the assembly 519, any wavefront error that is measured is principally due to the visual tunable lens 110.

This contribution of wavefront error due to the visual tunable lens can be taken into account by a processor, such as the determination and control module illustrated in FIG. 2, in determining actual wavefront error due to the eye 106. In this way, the optical quality of the visual tunable lens 110 becomes much less important, enabling the device to provide highly accurate measurements and prescription determinations even given the presence of the visual tunable lens 110. Thus, even with a visual tunable lens that has lower optical quality than a fixed lens, the processor may determine the actual wavefront error of the eye 106 with high precision by taking into account precise contribution of the visual tunable lens to wavefront error by calibration.

Figure 6:
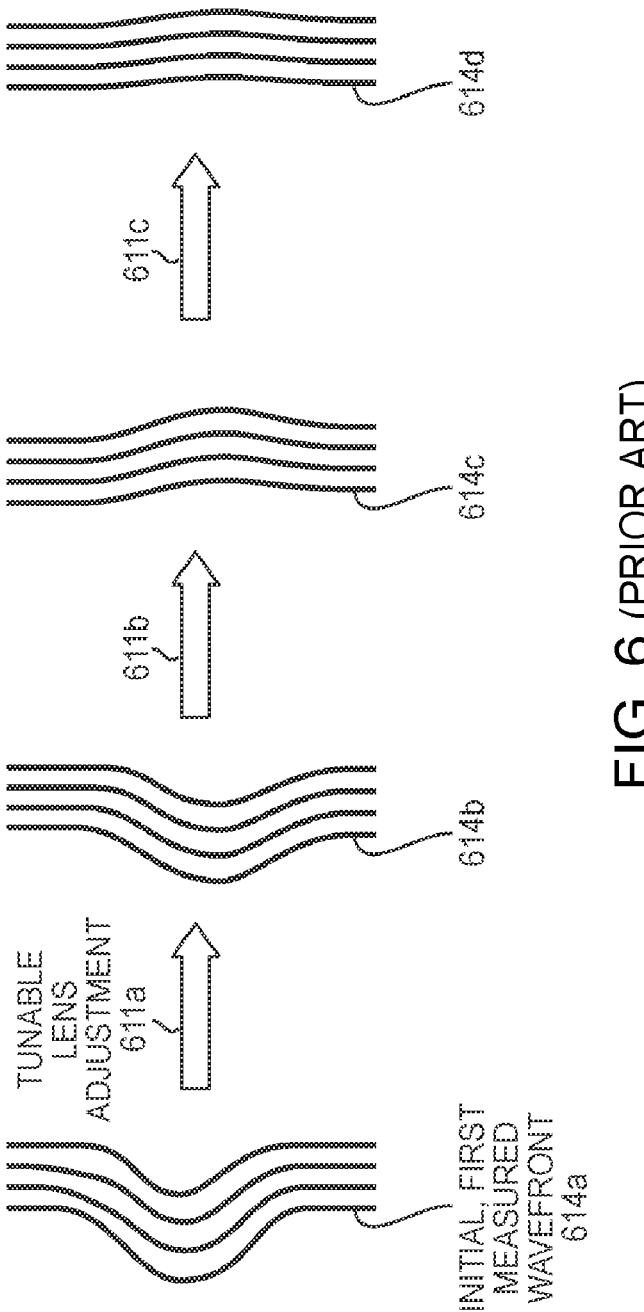
FIG. 6 (prior art) is a schematic flow diagram illustrating an embodiment iterative process for minimizing wavefront errors due to aberrations of an eye using the visual tunable lens illustrated in FIGS. 1-2 and for simulating the effects of eyeglasses.

FIG. 6 is a schematic flow diagram illustrating an iterative process for correcting wavefront errors due to aberrations of an eye using the visual tunable lens illustrated in FIGS. 1 and 2 and for simulating the effects of eyeglasses. Furthermore, where a light source tunable lens is used, as in FIG. 2, compensating adjustments may be made as follows.

A wavefront 614a is initially measured by the wavefront sensor 116 in FIG. 2, with no optical power applied by the visual tunable lens 110. An arrow 611a represents a tunable lens adjustment applied to the visual tunable lens 110 illustrated in FIG. 2. At this point, a corresponding, compensating adjustment can be made to the optical power of the light source tunable lens 210 illustrated in FIG. 2 in order to compensate for the effect of the visual tunable lens 110 adjustment on the eye illumination light and to maintain the eye illumination light focused onto a spot on the retina. A wavefront 614b is then measured by the wavefront sensor 116, which exhibits less wavefront error (less deviation from ideal planar wavefront).

Subsequently, an arrow 611b illustrates application of further adjustment to the visual tunable lens 110 to apply a more minor adjustment to simulate a better eyeglass correction, with corresponding adjustment made to the light source tunable lens 210. A wavefront 614c is then measured by the wavefront sensors 116. In this case, it can be seen that the wavefront 614c exhibits some over-correction having been applied by the visual tunable lens. An arrow 611c represents further minor adjustment to the visual tunable lens 110 to simulate eyeglass correction, as the simulation can best be applied using the parameters available with a specific visual tunable lens. As previously described, these adjustable parameters can include sphere, cylinder, and axis for particular tunable lenses. In addition, as tunable lenses continue to be developed and improved, it is expected that particular tunable lenses will be able to adjust and correct for higher-order corrections as well. In the case of higher-order corrections, similar iterative adjustments can be performed. A further, minor, compensating adjustment can be made to the light source tunable lens 20.

A final wavefront 614d is measured by the wavefront sensor 116, representing the best wavefront that can be obtained using the particular visual tunable lens 110, in view of any optical aberrations present in the visual tunable lens and in other optical components of the system. The schematic flow diagram illustrated in FIG. 6 can include many more iterations, depending on eye alignment stability, eye accommodation, reproducibility of wavefront measurements, potential averaging of subsequent wavefront measurements to obtain best estimates, etc. At each successive wavefront error measurement, a minimum (or maximum) error in wavefront may be determined. One way to characterize wavefront error is by means of a root mean square (rms) wavefront measurement, for example. However, other measures of wavefront error may also be used.

Furthermore, the iterative adjustment and measurement process illustrated in FIG. 6 can be applied to multiple parameters of the visual tunable lens 110 successively. For example, in example methods, the spherical adjustment of the tunable lens can be optimized with respect to the measured wavefront followed by subsequent optimizations of cylinder and axis, for example. This process can then be repeated (sphere, cylinder, and axis measured again) for further optimization. Because of the potential speed of adjusting tunable lenses, as described hereinabove, for updating lens settings, together with the acquisition speed for wavefront sensing (e.g., ten frames per second), this process can proceed very quickly, even when multi-dimensional and iterative.

FIG. 7 is a flow diagram illustrating a procedure 700 for determining a property of an eye. The property can include wavefront error produced by the eye, a refractive prescription for the eye, an accommodation range measurement, a presbyopia measurement, a phoropter measurement, and other measurements as described herein. Embodiment devices described herein, such as those described in connection with FIGS. 1-5K, may be used to perform the example procedure 700.

At 713a, a variable focal power is applied to light received from an eye, via a port of a housing configured to receive the eye, using a visual tunable lens. At 713b, light is passed from the eye along an optical path. At 713c, a wavefront of the light from the eye is measured, with the light being received via an optical path from the port of the housing.

At 713d, a property of the eye is determined based on the wavefront of the light from the eye. Further details regarding embodiment procedures encompassed by procedure 700 are described hereinafter.

Figure 8A:
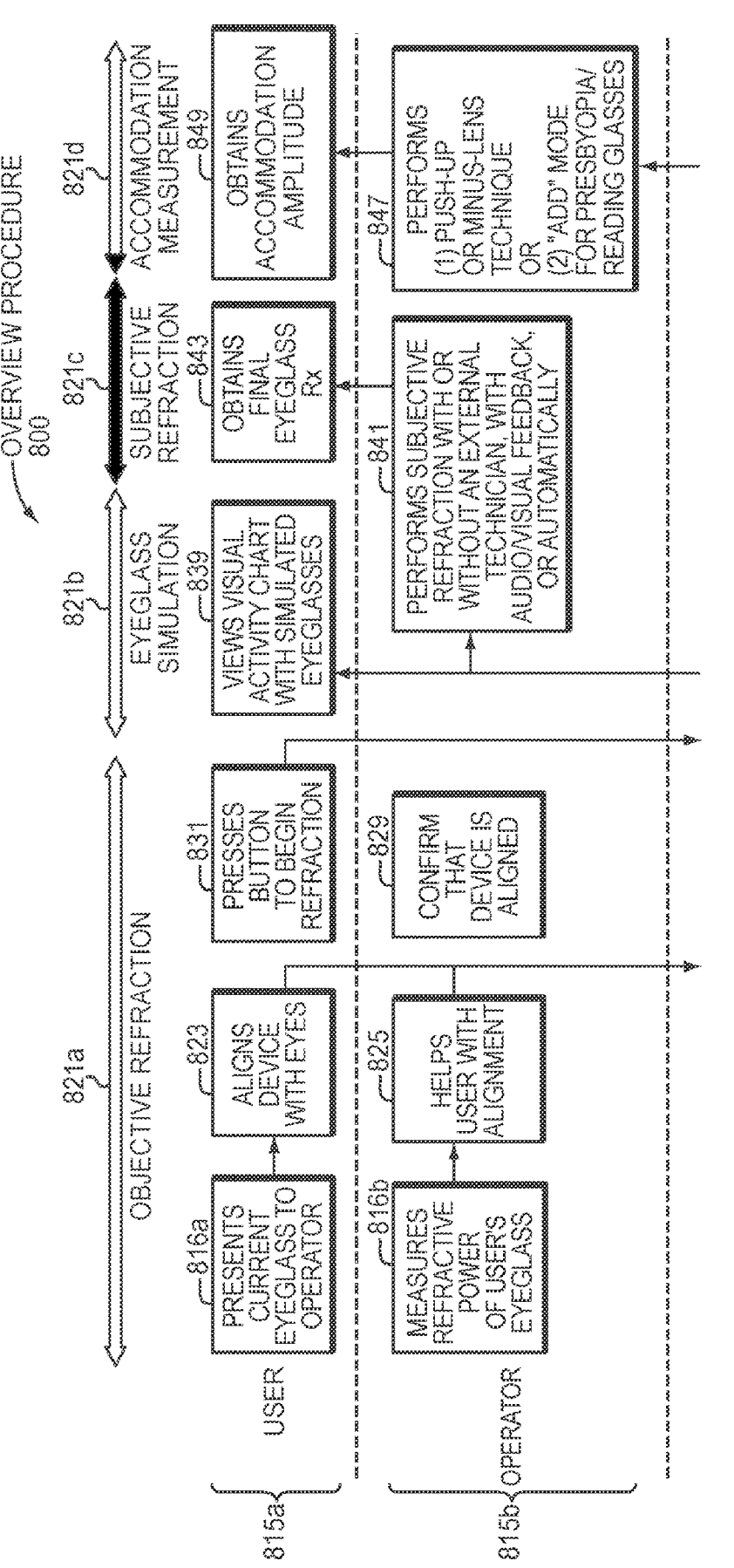
FIGS. 8A-8B (prior art) are an overall flow diagram illustrating various measurement procedures that can be performed using embodiment devices such as the "Quick-See" apparatus illustrated in FIGS. 5A-5C.
Figure 8B:
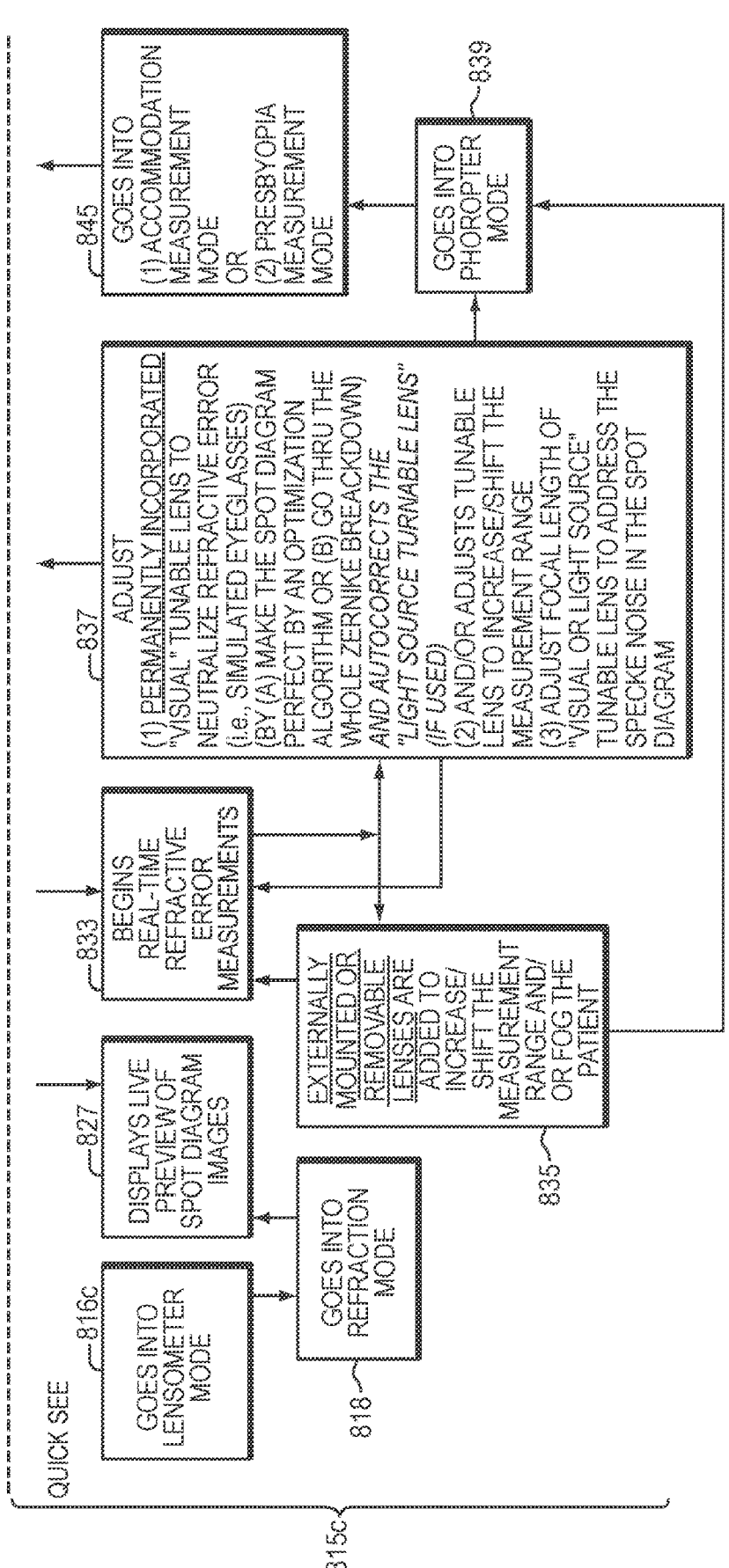

FIGS. 8A-8B are a flow diagram illustrating an overview procedure 800 including various measurements that can be performed on an eye patient, as well as an example clinical examination flow, using the embodiment apparatus illustrated in FIGS. 5A-5C. Because the embodiment apparatus in FIGS. 5A-5C (also referred to herein as the "QuickSee™" apparatus) can include various features similar to those illustrated in FIGS. 1-4, reference is also made to those figures.

Row 815a in FIG. 8A indicates operations that can be performed by a user, such as a person whose eyes are being measured using the QuickSee™ apparatus. Row 815b shows operations that can be performed by an operator, such as a technician, for example. In other embodiments, the actions described in row 815b can be performed by the user or can be performed automatically using an embodiment apparatus. Furthermore, other operations can be performed using embodiment devices by the user, an operator, or an optometrist or ophthalmologist, for example. Row 815c shows example actions that can be performed by the QuickSee™ apparatus.

Column 821a in FIGS. 8A-8B illustrates operations that can be used to identify an objective refractive correction. An objective refractive correction, as used herein, denotes a measurement that can be performed without regard to subjective refractive preferences of the user. For example, a refractive correction can be objectively estimated using embodiment devices based on the wavefront representation 118 obtained by the wavefront sensor 116 illustrated in FIG. 2, for example. Column 821b illustrates operations that can be used to improve an objective correction estimate by simulating the effect of refractive correction of eyeglasses by using a tunable lens, such as the visual tunable lens 110 illustrated in FIG. 2, for example.

Column 821*c* in FIGS. 8A-8B illustrates subjective refraction operations that can be performed to improve objective refraction estimates by obtaining feedback from a user regarding lens preferences, for example. This process is normally referred to as phoroptry when performed using a standard phoropter having a variety of fixed lenses in the clinic of an optometrist, for example. However, advantageously, in accordance with embodiments described herein, phoroptry can be performed using embodiment devices automatically or semiautomatically by taking advantage of tunable lenses. Column 821*d* illustrates example operations that can be performed using embodiment apparatus and methods to obtain eye accommodation range measurements.

In accordance with the objective refraction process described above, at 816*a*, the user optionally presents existing eyeglasses to an operator (e.g., technician). At 816*b*, the operator measures refractive power of the user's existing eyeglasses using the lensometer attachment 591 further described in connection with FIGS. 5A-5C. In order to perform lensometry, at 816*c*, the QuickSee™ apparatus goes into lensometry mode. Following lensometry, at 818, the lensometer attachment 591 is removed, and apparatus 500 goes into refraction mode for objective measurement of at least one of the user's eyes.

One advantage of using a visual tunable lens for lensometry includes the fact that a measuring range can be easily shifted by implementing a fixed tunable lens offset, for example. This is useful in case a particular eyeglass lens being measured is outside the base range of the apparatus. A further advantage of using a visual tunable lens for lensometry involves measurement accuracy. In particular, similar to the accuracy advantage described hereinabove for eye wavefront measurements in the presence of a visual tunable lens, lensometry accuracy can be improved by setting the visual tunable lens to negate the optical power of the eyeglass lens being measured so that the detected wavefront is as parallel as possible. As further described hereinabove, when the detected wavefront is as parallel as possible, then the wavefront measurements themselves can be more accurate, thus leading to more accurate lensometry when based on wavefront measurements. In this case, the measured optical power of the eyeglass lens can be determined based on the combination of the measured wavefront and the optical power implemented At 823, a user having the eye to be measured aligns an embodiment apparatus with an eye or eyes to be measured. The user puts the device in contact with the user's face and looks through the apparatus at a distant target. The user keeps the user's eyes open, with occasional blinking. At 825, the operator helps the user with the alignment process. In some embodiment procedures, alignment instructions are provided by the apparatus, such as through the speaker 362 illustrated in FIG. 3. At 827, as part of the alignment process, the QuickSee™ apparatus displays a live preview of spot diagram images provided by the wavefront sensor 116. These images can be shown at a reporting interface screen, such as that illustrated in FIG. 3, or at a screen of an attached cellular phone, as described in connection with FIG. 4, for example.

At 829, the operator confirms that the QuickSee™ apparatus is aligned with the eye of the user. In other embodiments, this can be performed automatically, using feedback from the device itself. Whether alignment is confirmed manually by the operator or automatic alignment feedback is provided, alignment analysis can be based on the spot diagram from the wavefront sensor. As the user looks through the apparatus, the degree to which the user's eye is optically centered with the wavefront sensor can be analyzed. In particular, this can be done by checking how well the spot diagram is centered on the wavefront image sensor and then providing feedback on how to move the device relative to the user's face in order to optically center the user's eye to the wavefront sensor.

At 831, the user can press the trigger switch 397 illustrated in FIG. 5A to indicate that refractive measurements should begin. Following this, at 833, the QuickSee™ apparatus begins real-time refractive error measurements. Then, at 835, as necessary, externally mounted or removable lenses can be added as modular attachments to the QuickSee™ apparatus to shift a measurement range of the visual tunable lens or to fog the patient's view. The addition of these lenses may be performed by the operator, for example. As described hereinabove, the example Varioptic Visayan® 80S0 tunable lens can apply variable focus optical power between −12 and +12 dpt. Therefore, if this lens is used as the visual tunable lens, and the patient's eye has a spherical error of about −12 dpt, for example, then the tunable lens may not provide a convenient range of adjustment to ensure that optimum refractive correction is determined and simulated for the patient. In this example case, an additional, externally mounted, +5 dpt fixed lens could be added to the apparatus and used to shift the measurement range by +5 dpt for measurement and simulated refractive correction. In alternative embodiments, a different visual tunable lens having a different measurement range could be used.

As described hereinabove in connection with FIG. 2, for example, the eyepiece proximal port 205 can be configured to accept one or more additional, modular, fixed lenses as needed. As an alternative, a user may be given instructions by the QuickSee™ apparatus, through the reporting interface screen 354 or the speaker 362 illustrated in FIG. 3, for example, to insert specific lenses for offset or fogging.

As to the eyeglass simulation column 821*b*, at 837(1), the permanently incorporated visual tunable lens 110 illustrated in FIG. 2 is adjusted in order to neutralize refractive error caused by imperfections in the eye 106. This process can be iterative as illustrated in FIG. 6, for example. When the refractive error is made as close as possible to zero, indicated by plane waves in FIG. 6, and by a uniform, evenly spaced spot diagram from a Hartmann-Shack wavefront sensor, for example, and the tunable lens 110 is adjusted to achieve such results, then the eye 106 views the external target object 252 through the open view apparatus 200. Then, the eye 106 is effectively viewing through a corrective lens simulated by the visual tunable lens 110. This neutralization process can be completed empirically by running an optimization routine to make the spot pattern on the wavefront sensor as uniform as possible. An example optimization procedure is described hereinafter.

The optimization procedure to make the spot pattern as uniform as possible can be performed in several ways. One straightforward method is to minimize the root mean squared (rms) error of the wavefront with respect to an aberration-free wavefront. Examples of other well-known parameters which may be used in the optimization procedure are the peak-to-valley (P-V) wavefront aberration or the Strehl ratio, among others. Some of these methods are described in the following paper: "Thibos et al, Accuracy and precision of objective refraction from wavefront aberrations, Journal of Vision 2004 (4), 329-351." The optimization procedure can be performed iteratively using a standard closed loop control in which the feedback signal (error signal) is given by any of the aforementioned parameters.

Another possibility to perform the optimization procedure is to maximize the optical or visual quality. This approach is based on the fact that mathematically is easy to add to the eye's aberration map that our device is continuously measuring. Using the measured spherical and/or cylindrical wavefront (which simulates the correction) we can then compute the resulting retinal image using standard methods of Fourier optics. The curvature of the added wavefront can be systematically or iteratively varied to simulate a through-focus experiment that varies the optical quality of the eye+lens system over a range. Given a suitable metric of optical quality (such as the Strehl ratio), this computational procedure yields the optimum lens needed to maximize optical quality of the corrected eye.

Alternatively, wavefront error optimization can be based on Zernike coefficients. Zernike coefficients can be obtained in each measurement by the determination and control module 220 and can be used to calculate the RMS error of the wavefront obtained by the wavefront sensor 116 (or any other parameter of interest). This parameter can be used as error signal in a closed loop to adjust the Sphere, Cylinder and Axis in the visual tunable lens in order to minimize the RMS error. Furthermore, for each measurement, the iterative process may be performed to calculate the adjustments to apply to the visual tunable lens 110 based on optical or visual quality metrics obtained after retinal image quality estimation.

As a further alternative, the determination and control module 220 may calculate Zernike coefficients based on the wavefront obtained by the wavefront sensor 116, and spherical, cylinder, and axis adjustments to the visual tunable lens 110 may be made to compensate for corresponding refractive error components indicated by the Zernike expansion. One simple example method includes causing the tunable lens 110 to correct for second order Zernike terms (defocus, oblique astigmatism, and vertical astigmatism).

During this process, in each case of adjustment of the visual tunable lens 110, the light source tunable lens 210 can be adjusted by a corresponding amount to maintain a focused spot of the illumination light 240 on the retina.

At 837(2), the visual tunable lens 110 can be adjusted to increase or shift the measurement range. The correction objectively determined based on wavefront measurements can be implemented as a fixed value for eyeglass simulation. Further, this simulation can be implemented as a coarse offset, and then, in the subjective refraction stage, be allowed to vary over a relatively small range, such as +/−1.0 dpt, +/−0.5 dpt, or +/−0.25 dpt, for example, based a user's preferences. At 837(3), during the real-time measurement and iterative neutralization process described above, the visual tunable lens 110 or the light source tunable lens 210 may be adjusted slightly (dithered) to address speckle noise in spot diagrams obtained by the wavefront sensor 116. This process is further described hereinabove in connection with FIG. 2.

At 839, with the spot diagram detected by the wavefront sensor 116 optimized to be uniform and to indicate minimized refractive error by adjustments of the visual tunable lens 110, the user can view a standard visual acuity chart, through the open view apparatus, with a simulated eyeglass provided by the visual tunable lens 110 through which the user views.

In column 821c, at 841, the visual tunable lens 110 has already been set to an optical power to simulate the best estimate for refractive correction based on objective refraction, using measurements of the wavefront sensor. With this setting as a starting point, subjective refraction is performed, in a manner somewhat similar to phoroptry. However, with the benefit of the visual tunable lens 110, this process can be performed automatically or semi-automatically, with minimal help from an external technician, or by the user alone, all while the user views through the same apparatus used for wavefront aberrometry and objective refraction.

In one embodiment, the speaker 362 provides an audible message to the user to turn the dial 356. While still viewing the visual acuity chart (e.g., Snellen chart, LogMAR chart, EDTRS chart, or tumbling E chart) or another target, the user adjusts the dial 356 to optimize the view for the eye under test, and sphere is adjusted for the visual tunable lens 110 in accordance with the dial 356 adjustments. Subsequently, the speaker 362 asks if the view is optimized. The user responds, through the microphone 364, "yes." Then, the speaker 362 provides a message to again optimize the view using the dial 356. This time, the cylinder adjustment of the visual tunable lens 110 is made with the user still viewing the visual acuity chart. After similar adjustments of the dial and a similar confirmation through the speaker and microphone, an axis adjustment can be made similarly. After this process, it may be desirable to iterate, by once again asking the user to adjust the dial 356 to optimize sphere, and so forth.

In another embodiment, the user uses the directional buttons 358 to adjust sphere correction up or down, as desired. In another embodiment, an external technician provides assistance during the subjective refractive measurement. For example, the technician can ask the patient whether the patient sees more clearly with a first tunable lens setting or a second tunable lens setting, and so on, thus guiding the patient through an entire subjective measurement process. The technician can perform subjective refraction using the QuickSee™ apparatus as, essentially, a phoropter. Switching of visual tunable lens settings may be done by direct input to the device. However, more preferably, input can be via a remote device, such as a tablet computer linked to the QuickSee™ apparatus. In this case, a tablet computer can be operatively connected to the QuickSee™ apparatus much like the cellular phone 492 illustrated in FIG. 4, for example. In yet another embodiment, the visual tunable lens 110 is slowly varied over a limited range, and the user presses a trigger button similar to the trigger switch 397 when the user's view is optimized with respect to sphere, cylinder, or axis, for example.

At 843, a final eyeglass prescription is obtained based on the final refractive values obtained from subjective refraction. In some embodiments, data are collected, either by the apparatus 200 itself within the determination and control module 220, or by an external monitoring computer connected via the network interface 468 illustrated in FIG. 4. Data regarding the subjective refraction final values, as compared with the objective refraction values, can be accumulated to produce statistics for better prediction of final prescription values.

As described hereinabove, one unique feature of embodiment devices is the ability to perform both objective and subjective refraction using the same device. For each patient whose eyes are measured, embodiment apparatus and methods can be used to obtain (i) an initial objective refraction, and (ii) a final subjective refraction. For each patient, these two values can be logged to see how different they are.

By accumulating and learning from such data, methods can be implemented to effectively modify the objective measurement initially measured to provide a more accurate starting point for subjective refraction. A machine learning approach can take into account not only objective and subjective refractions measured for each patient, but also any user's (eye patient's) personal information (e.g., age, gender, race), or additional information (e.g., high-order aberrations measured objectively, or retinal image quality calculated from the measurements), to be stored and analyzed according to a machine learning method to further improve prediction accuracy.

A useful advantage of embodiments that use this machine learning/prediction approach is that overall time for an entire refraction process can be reduced by having a more accurate starting point for subjective refraction. It is also possible that, given sufficiently developed prediction routines, that subjective refraction need not even be performed, and that prediction of subjective correction may be done solely on the basis of objective refraction results.

As further described herein, the property of the eye measured by an embodiment apparatus can be an objective property based on the wavefront measurements, without taking into account subjective patient preferences that would be reflected in phoroptry results, for example. A determination module can be used to predict a subjective refractive preference of a person having the eye based on the objective property. The determination module can be made to predict the subjective refractive preference based further on a demographic or physical attribute of a patient. Demographic attributes can include age, gender, ethnicity, weight, height, occupation, or another demographic attribute of the patient. Physical attributes can include retinal image quality, axial length, iris color, topography, corneal curvature, aberration of higher order than spherical or cylindrical aberration, or another attribute of the eye, or attribute of a patient's body, which may have some correlation with difference between objective and subjective eye refraction results.

The determination module can be configured to predict the subjective refractive preference using a correlation developed from a database including respective demographic or physical attributes and respective objective eye properties for many different eye patients. A database storing the respective attributes can be included in the memory 470 illustrated in FIG. 4, or in an external server accesses via the network interface 468 in FIG. 4, for example.

In one example, objective and subjective refraction results along with respective ages for many patients examined using an embodiment apparatus can be stored in memory in the apparatus. A determination and control module in the apparatus can determine that the difference between objective and subjective refraction results for the apparatus varies approximately linearly with age of the patient, for example. Then, based on this linear correlation, the determination and control module can predict subjective refraction for a given patient of given age based on the given patient's objective refraction results and the patient's age.

In another example a determination and control module may determine that the difference between objective and subjective refraction results for the apparatus diminishes with the magnitude of the objective refraction results themselves roughly according to a quadratic function. Thus, for a given patient, based on the patient's objective refraction results and the quadratic function, the determination and control module may predict the given patient's subjective refractive preference. The visual tunable lens can then be set to the predicted subjective preference, and further subjective examination may optionally be performed.

It should also be noted that such predictive methods can also be applied to data obtained from devices that only perform objective refraction. Objective results from a wavefront aberrometer, for example, may be compared with subjective phoroptry results over a large sample of patients to develop predictive correlations that can be applied to obtain (effectively) subjective-quality refractive corrections on the basis of objective measurements alone. Nevertheless, it is preferable to develop the correlation between objective and subjective refraction, and the prediction of subjective refractive preference, on the basis of objective and subjective measurements acquired using the same apparatus within the same examination session. Use of the same apparatus in this context can potentially be faster and more consistent.

The determination module 120 in FIG. 1 or the determination and control module 220 in FIG. 2, or another processor that is part of, or separate from, the apparatus in FIGS. 1-2, for example, can perform calculations to predict a subjective refractive preference of a person having the eye based on the property of the eye based on the wavefront. This can be done by comparing, over time, the difference between refractive preferences (phoroptic-type determinations) and objective refraction values as a function of various patient attributes, such as the demographic and physical attributes described hereinabove. Various methods and calculation routines can depend upon the empirical data collected over time. Methods may be used that take into account age, gender, the absolute objective refraction value for the eye, or any other value for the user that may have a correlation with the difference between objective and subjective refractive values. In this way, prediction of subjective refraction, even based on objective refraction alone, may be improved over time.

Column 821d illustrates an example procedure for obtaining accommodation amplitude (range) measurements based on patient feedback. At 845, the apparatus 200 goes into accommodation measurement mode (presbyopia measurement mode). At 847, push-up or minus-lens technique is used or "add" mode is used to determine a prescription for reading glasses to deal with presbyopia. At 849, a final accommodation amplitude is obtained.

In order to measure accommodation amplitude (either with push-up or minus-lens technique), it can be assumed that the person who is being tested is emmetropic (i.e. requires no corrective lenses for distance vision) or is properly corrected for distance vision (for example, with eyeglasses or contact lenses). Embodiment devices such as the QuickSee™ apparatus can provide proper correction for distance vision via a visual tunable lens, which can take the place of a phoropter or set of trial lenses.

The visual tunable lens can be especially advantageous when using the minus lens method to measure accommodation. Traditionally, for the minus lens method, the accommodative demand of a small nearpoint target is changed as minus lenses are introduced to the patient monocularly until the target is no longer clear, based on patient feedback. However, with a visual tunable lens-based apparatus according to embodiments, no additional lenses need to be carried around, and the introduction of more minus power can be done continuously, instead of in a step-wise fashion as done traditionally. The capability for continuously variable power is expected to result in a more accurate measurement of accommodation amplitude.

The procedure illustrated in column 821d using embodiment methods and apparatuses differs significantly from existing methods for accommodation measurement. Existing methods typically include using a physical moving target attached to a phoropter. The physical moving target starts a distance away from the person (to correct for distance vision) and is gradually moved towards the patient's eye to track the patient's myopia. At a sufficiently small distance between the eye and movable target (closer than the near point), the eye can no longer accommodate. Existing systems using a moving target can have disadvantages of being physically large, requiring moving parts, requiring actuators for the movement, lacking the ability to cycle between settings quickly, potentially having drift or hysteresis, and causing the eye to over- or under-accommodate if the physical target is moving during measurement and the movement is perceived by the eye or eyes under test. In contrast to existing systems, embodiments described herein can take advantage of a tunable lens for fast, repeatable, accurate accommodation measurements without mechanical moving parts.

A further advantage of embodiments described herein, in contrast to existing methods and systems, is that objective accommodation measurements can be obtained by acquiring wavefront measurements at any time during or between changes to the tunable lens settings, all while the patient views the same distant target through the tunable lens whose settings are changed as needed. In this manner, a very precise determination of accommodation can be obtained, which is not possible with existing methods and systems, even where both lens systems and wavefront aberrometers are both used in the same setting but as part of different systems.

In some embodiments, no subjective feedback from the patient is even required for an accommodation measurement, because wavefront measurements are iteratively made while the tunable lens setting is changed until the wavefront measurements indicate that accommodation is no longer occurring. The accommodation amplitude measurement can be completed more rapidly since there is no need to wait for the patient's verbal responses. Patients that are asked to provide subjective feedback during an eye examination, such as an accommodation range examination, are often stressed about their feedback and even question their own final results because they are not sure whether their responses have been "correct." The objectivity that can be provided by an embodiment tunable lens and wavefront aberrometry combined system can eliminate the stress of these patients. The results can be more repeatable because they are not affected by a patient's anxiety regarding "correct" responses and because of the inherent precision of wavefront aberrometry. The accuracy of the measurements using embodiments described herein can also be more reliable because patient communication issues (e.g., with children, elderly patents, patients that do not speak the same language as a clinician, etc.). An example embodiment method for determining accommodation using an embodiment combined tunable lens and wavefront aberrometry apparatus is further described hereinafter in connection with FIG. 9E.

FIGS. 9A-9F supplement the overall refractive examination flow diagram in FIGS. 8A-8B by illustrating in further detail how specific portions of the flow diagram in FIGS. 8A-8B can be carried out.

FIG. 9A shows a procedure 900a in flow diagram form illustrating in greater detail how a lensometry measurement may be performed using embodiment apparatuses and methods, as illustrated in summary at element 818 in FIG. 8B. At 951a, a lensometry attachment, such as the attachment 591 in FIG. 5A, is attached to an embodiment device. Eyeglasses such as eyeglasses 598 in FIG. 5A are placed into the attachment. At 951b, light is sent into the eyeglass lens along an optical path. For example, eye illumination light 240

(illustrated in FIG. 2) can travel along the path illustrated in FIG. 2, exit the apparatus through the tunable lens 110, and enter into the lensometry attachment 591.

At 951c, the wavefront of light from the eye, particularly from the artificial eyes 599 illustrated in FIG. 5A, is measured. The light is received via an optical path from the lens on the attachment, similar to the light 108 illustrated in FIG. 2. At 951d, the refractive profile of the eyeglass lens is determined by a module, such as the determination and control module 220 illustrated in FIG. 2. At 951e, a refractive profile of the eyeglass lens is stored in the determination and control module 220.

FIG. 9B is a flow diagram illustrating in greater detail how speckle in wavefront measurements can be suppressed using embodiment apparatus and methods, particularly by taking advantage of tunable lenses. In a procedure 900b illustrated in in FIG. 9B, at 953a, light is sent from an illumination light source (e.g., source 238 in FIG. 2) along an optical path through a light source tunable lens (e.g., lens 210 in FIG. 2) and through the visual tunable lens (e.g., lens 110 in FIG. 2). At 953b, a wavefront of the light is shaped by changing the focal power of the light source tunable lens, or the visual tunable lens, or both. This wavefront shaping can be similar to the iterative shaping illustrated in FIG. 6, for example. At 953c, small variations in the wavefront of the light are introduced, by oscillating the focal power of the light source tunable lens, the visual tunable lens, or both, to randomize the speckle pattern generated at the eye and the wavefront sensor.

FIG. 9C is a flow diagram illustrating in greater detail how objective refractive measurements may be obtained using the embodiment apparatus and methods, particularly by taking advantage of a visual tunable lens according to an objective refraction procedure 900c. At 955a, light is sent from an illumination light source, to an eye, along an optical path through a light source tunable lens and a visual tunable lens. Both the light source tunable lens and visual tunable lens are initially set to apply zero focal power. At 955b, light that is reflected or backscattered from the retina of the eye is passed through the visual tunable lens to a wavefront sensor.

At 955c, a wavefront of the light from the eye is measured. At 955d, the refractive error (e.g., spherical and astigmatic) of the eye is estimated based on the measured wavefront, together with focal power applied subsequently by the visual tunable lens and light source tunable lens, as described hereinabove in connection with FIG. 6, for example. At 955e, appropriate focal powers (e.g. spherical and astigmatic) are applied by the visual tunable lens and light source tunable lens to negate an estimated refractive error of the eye to the greatest degree possible in view of the quality and available adjustments of the tunable lenses. At 955f, elements 955c, 955d, and 955e are repeated until an estimated refractive error of the eye is stable to within an acceptable level of variation (e.g., 0.25 dpt, 0.15 dpt, or 0.05 dpt).

Figure 9D:
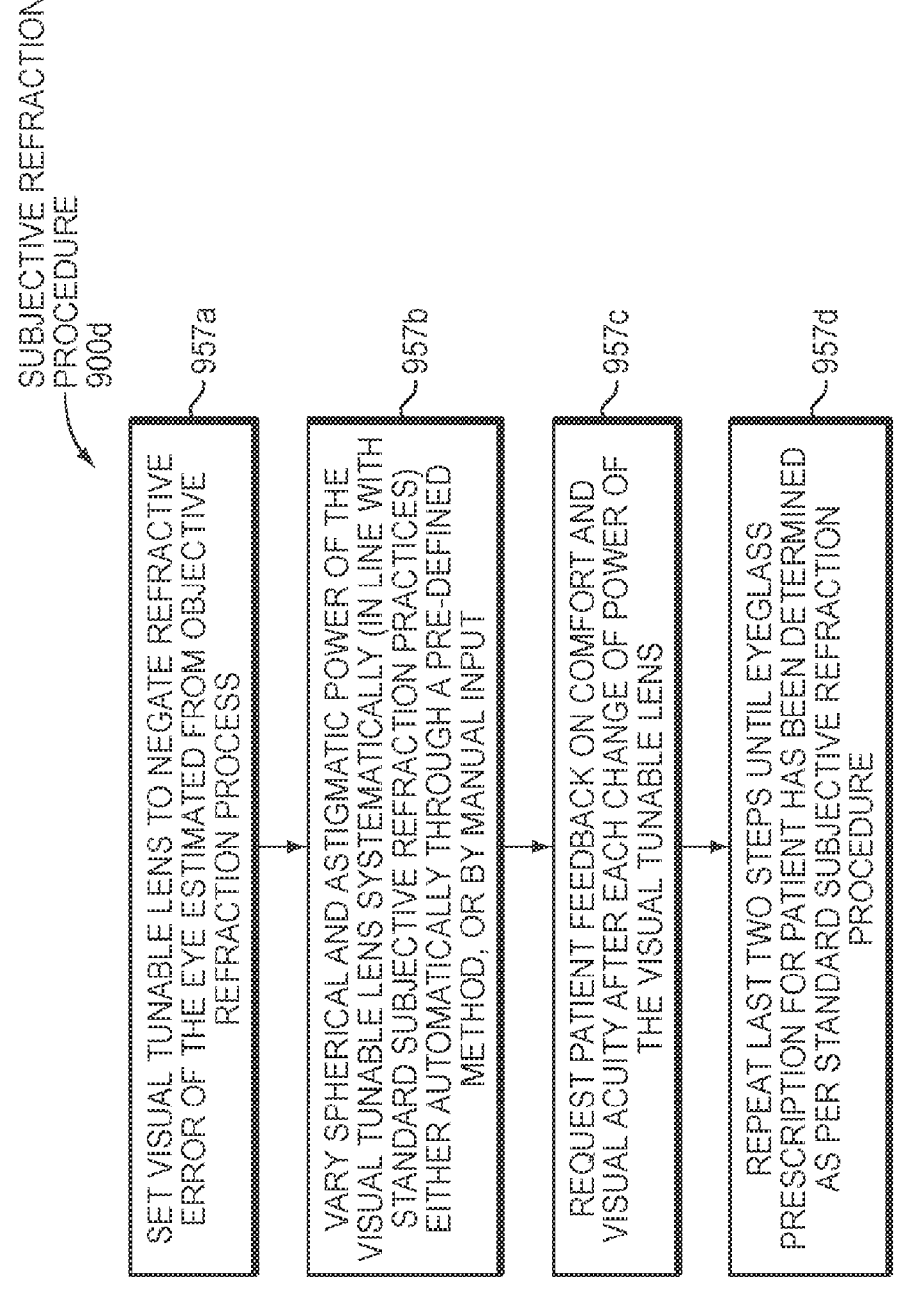
FIG. 9D (prior art) is a flow diagram illustrating how embodiment devices and methods can be used to perform subjective refractive measurements.

FIG. 9D is a flow diagram illustrating in further detail how subjective refractive measurements can be obtained using embodiment apparatus and methods, according to a subjective refraction procedure 900d. At 957a, a visual tunable lens is set to negate refractive error of the eye of the user, where the refractive error is estimated from an objective refraction process such as that illustrated in FIG. 9C. At 957b, spherical and astigmatic power of the visual tunable lens are varied systematically (in line with standard subjective refraction practices), either automatically through a predefined method, or by manual input from the eye patient or an assistant.

At 957c, eye patient feedback is requested regarding comfort and visual acuity after each change of power of the visual tunable lens. At 957d, elements from 957b-c are repeated until an eyeglass prescription for the eye patient has been fully determined in line with standard subjective refraction procedures (e.g., using a phoropter). Accordingly, because subjective refraction as illustrated in example FIG. 9D may use objective results from example FIG. 9C as a starting point, refractive prescriptions and other properties determined by a determination module such as the module 120 illustrated in FIG. 1 or the determination and control module 220 illustrated in FIG. 2 can be based on both the wavefront aberrometry (objective results) and the tunable-lens-based phoroptry (subjective results) from the same apparatus.

FIG. 9E is a flow diagram illustrating an example accommodation procedure 900e that shows how embodiment devices and methods can be used to measure accommodation amplitude for evaluation of presbyopia. At 959a, a visual tunable lens is set to negate refractive error of a patient's eye as determined by subjective refraction. At 959b, the patient is requested to view through the apparatus toward a target with small text or symbols, such as a reduced Snellen chart, for example, placed at typical reading distance away from the eye, about 0.4 meters.

At 959c, minus optical power is added to the visual tunable lens gradually until the small text or symbols on the target become, and remain, blurred based on feedback from the patient. At 959d, accommodation amplitude of the patient's eye is determined by adding the total minus power of the visual tunable lens to the reciprocal of the distance of the target (about $1/0.4$ m).

While patient feedback in combination with tunable lens adjustments alone may be used to determine accommodation range, a particular advantage of embodiments described herein, including those with both a wavefront sensor and tunable lens in the same apparatus, is that accommodation may be measured in a more automated fashion by taking advantage of wavefront measurements in combination with tunable lens adjustments. As an example, objective and subjective refractive measurements may be performed first, as outlined in FIGS. 8A-8B or in FIGS. 9C-9D. This can provide final corrective prescription for the patient, initially without regard to accommodation range, and the visual tunable lens may be set to the final settings. Subsequently, the apparatus may measure an initial corrected wavefront with these tunable lens settings, and the apparatus may then change the tunable lens focal power very slowly in small steps, allowing for the patient's given eye under test to accommodate while still viewing the fixed target indicia.

At each lens adjustment step, after appropriate accommodation, an additional wavefront measurement can be automatically acquired by the apparatus, saved, and monitored by the determination module. After a sufficient number of steps in focal power, when the determination module eventually determines that the measured wavefront has deviated at least a minimum threshold from the initial corrected wavefront value (or otherwise determines from the wavefront measurements that the eye under test is no longer sufficiently accommodating), then the determination module may determine that a difference between the tunable lens focal power at the final optimized settings and the focal power at the point of maximum accommodation is the accommodation range of the patient's eye. As will be understood in view of this description, accommodation measurements such as those described above may also be performed according to binocular embodiments on both eyes at the same time.

FIG. 9F is a flow diagram illustrating an example machine learning procedure 900f showing how machine learning can be implemented in embodiment devices and methods to predict subjective refractive preferences of an eye patient based on objective measurements. At 961a, patient data including at least a refractive error estimated by objective refraction and a refractive error determined by subjective refraction are stored in a database. The database can include the memory 470 in FIG. 4 or a database external to an embodiment apparatus, such as a network database accessed via the network interface 468 in FIG. 4, for example.

At 961b, a mathematical model from the database (e.g., derived from machine learning techniques) is used to predict refractive error determined by subjective refraction given refractive error estimated by objective refraction, as determined according to FIG. 9C, for example. At 961c, predicted refractive error is used as an initial starting point for subjective refraction, as carried out according to FIG. 9D, for example.

FIGS. 10A-10B are flow diagrams illustrating successive parts of a single embodiment procedure 1000 for determining subjective refractive preferences of a patient using embodiment apparatuses. It should be understood that the procedure illustrated in FIG. 9D for subjective refraction is a general procedure that can further include many different variations using embodiment apparatuses. In general, the procedure 1000 in FIGS. 10A-10D is a particular variation that includes iterative determination of coarse and fine subjective refractive preferences for a given eye and allows a patient to interact directly with an apparatus having interactive features to determine the subjective preferences. This can be done with smart, iterative control of visual-tunable-lens vision correction values using interactive patient feedback.

In some embodiments consistent with this disclosure, an optometrist or assistant asks the patient which correction settings for the visual tunable lens are subjectively better, iteratively, as refractive values of the visual tunable lens are changed, similar to the iterative procedure used in standard, optometrist-assisted phoroptry measurements. However, in the procedure 1000, the embodiment apparatus requests that the patient turn the dial 356, which is set to control certain refractive values of the visual tunable lens, iteratively, over coarse and then fine ranges, and the device records the final settings made by the patient to refine subjective preferences. Each time the patient is asked by the device, through the speaker 362 illustrated in FIG. 3, to optimize a setting, the patient turns the dial 356 on the housing of the apparatus, while viewing a target such as a Snellen chart through the apparatus, until the patient is satisfied that he or she has adjusted the dial such that the visual tunable lens is set to the best value for visual acuity. Then, the apparatus automatically records the optimum tunable lens parameter found by the patient, as particularly described hereinafter. In other embodiments, the communication interface 360 in FIG. 3 may be used only to query the eye patient verbally and receive a voice-recognized verbal response from the patient, such as "one" or "two," regarding which subjective, refractive preference is better.

Another feature of the example procedure 1000 is that it illustrates how the orthogonal basis set, spherical equivalent power M, vertical Jackson cross cylinder J0, and oblique Jackson cross cylinder J45 can be set mutually independently by the apparatus. This is in contrast to other embodiments that use the standard clinical S, C, & A basis set referenced hereinabove in relation to FIG. 3, for example. It will be understood that an embodiment apparatus that has control over S, C, and A mutually independently may also control M, J0, and J45 mutually independently by a mathematical transformation.

In general, the procedure 1000 includes setting the visual tunable lens to the optimum settings determined from the objective refraction process using the wavefront aberrometer. An example procedure for determining objective refraction is described in connection with FIG. 9C. Thereafter in the procedure 1000, coarse subjective settings are determined. This is followed by setting the visual tunable lens to the optimum coarse subjective refractive value settings and then determining fine subjective refractive settings. The finer subjective refractive settings are used as the final subjective refractive preference values for the patient, and a refractive prescription may then be determined based on the fine subjective settings, for example. It should be understood that "setting the visual tunable lens," as used herein, can include setting one or more of a plurality of individual tunable lenses optically arranged in series, as described hereinabove in relation to FIG. 1.

In greater detail, in FIG. 10A at 1063, the visual tunable lens is set to optimum objective values for M, J0, and J45 (Mopt, J0opt, and J45opt, respectively) previously determined from objective refraction process based on wavefront aberrometry (see, e.g., FIG. 9C). These optimum objective values can be stored in the memory 470 illustrated in FIG. 4, and the lens settings can be made in response to commands from the processor 472 in FIG. 4, for example. Accordingly, at 1063*a-c*, M is set to Mopt, J0 is set to J0opt, and J45 is set to J45opt, respectively.

At 1065, coarse subjective settings Mopt', J0opt', and J45opt' are determined. In the procedure 1000, coarse subjective settings are determined in the following manner. At 1065*a*, the dial 356 is set to control the visual tunable lens such that, over a full range of motion of the dial available to the patient, M will vary over a range of Mopt+/−0.5 dpt while J0 and J45 are maintained constant at J0opt and J45opt, respectively. At 1065*b*, the apparatus, via the speaker 362, instructs the patient to turn the dial 356 iteratively to optimize subjective visual acuity preference. During this adjustment, a full range of motion of the dial 356 only allows adjustment over the Mopt+/−0.5 dpt range, such that the patient cannot deviate too far from the optimum objectively determined setting. It should be understood that the range of +/−0.5 dpt for the coarse adjustment is an illustrative value, and this value may be changed and set in the apparatus based on further engineering, doctor or optometrist knowledge, machine learning as illustrated in FIG. 9F, demographic factors, or other factors, as necessary. At 1065*c*, the apparatus then saves this value as the coarse subjective preference Mopt' and sets the visual tunable lens to this value.

At 1065*d*, the apparatus configures itself to control vertical Jackson cross cylinder J0 in response to a patient adjusting the dial 356. In particular, the apparatus sets itself to adjust J0 over a range of J0opt+/−0.5 dpt as the dial 356 is adjusted over its full range. Meanwhile, the apparatus maintains the visual tunable lens at constant Mopt' and J45opt. At 1065*e*, the patient is requested, through the speaker 362, to turn the dial 356 iteratively to optimize J0 to an optimum coarse subjective preference value J0opt'. At 1065*f*, the apparatus then saves J0opt' and sets the visual tunable lens to this value.

At 1065*g*, a similar procedure is carried out for the parameter J45. The apparatus sets itself to control J45 over a range of J45opt+/−0.5 dpt as the patient turns the dial 356 over its full range, while maintaining constant values Mopt' and J0opt'. At 1065*h*, the apparatus asks the patient to turn the dial 356 iteratively to optimize visual acuity, and the patient finally settles on a preferred setting. At 1065*i*, the apparatus saves the setting as the optimum coarse subjective preference value of J45, namely J45opt'. With the coarse subjective refractive settings having been determined according to the patient's preferences, at 1067, the apparatus proceeds to determine the fine subjective settings, as illustrated in FIG. 10B, where the procedure 1000 is continued.

In FIG. 10B, in greater detail, at 1069, the apparatus sets the visual tunable lens to the coarse subjective settings determined at 1065 in FIG. 10A, if this has not already been done. Particularly at 1069*a-c*, the visual tunable lens set to Mopt', J0opt', and J45opt', respectively. At 1071, fine subjective settings are then determined in a manner similar to the manner used to determine the coarse subjective settings, except that the coarse subjective settings are used as the starting point instead of the objective settings. An illustrative, example fine range variation of +/−0.2 dpt variation is used for each parameter. However, as noted above in relation to the coarse variation range, this fine variation range may be selected or set based on additional information or preferences.

At 1071*a*, the apparatus is set to respond to the patient's turning of dial 356 over its full range by controlling M correspondingly over a range of Mopt'±0.2 dpt while maintaining constant J0opt' and J45opt'. At 1071*b*, the patient is requested through the speaker to turn the dial iteratively to optimize visual acuity for the particular eye, OD or OS, that is under test. At 1071*c*, the fine subjective preference Mopt" is saved in memory, and the visual tunable lens is set to this value.

At 1071*d*, the apparatus sets itself to control J0 over a range of J0opt'+/−0.2 dpt in response to the dial being changed over its full range, while still maintaining constant Mopt" and J45opt'. At 1071*e*, the apparatus asks the patient to turn the dial iteratively to optimize visual acuity. At 1071*f*, the apparatus records the value J0opt" and sets the visual tunable lens to this value. At 1071*g*, the apparatus configures itself to control J45 over a range of J45opt'+/−0.2 dpt in response to the dial being turned over its full range. At 1071*h*, the patient is requested to turn the dial iteratively to optimize visual acuity. At 1071*i*, the apparatus records the optimum fine subjective preference value J45opt" and sets the visual tunable lens to this value.

At 1073, Mopt", J0opt", and J45opt" are then used as the best subjective refractive settings. These values may be set on the apparatus for a final confirmation from the patient that the settings are valid and acceptable. While not illustrated in FIGS. 10A-10B, the apparatus may optionally perform other functions at this point. For example, the apparatus may show the patient corrected and uncorrected views by changing the visual tunable lens, while speaking to the patient accordingly, similar to procedures followed by clinicians during traditional phoroptry. Furthermore, the apparatus may optionally give the patient a further opportunity to indicate that additional adjustments are preferred, either by pressing the trigger switch 397 illustrated in FIG. 3 or by the patient answering "yes" through the microphone 364 illustrated in FIG. 3, for example.

The procedure 1000 may also be repeated for each eye OD and OS in turn. Still further, the procedure 1000 may be modified such that coarse subjective testing is performed on each eye OD and OS in turn, followed by fine subjective testing on each eye in turn. Furthermore, it will be recognized by those skilled in the art of optometry that there are advantages in determining subjective refractive corrections of both eyes at the same time. As is known in the art, a patient's preferred correction for a given eye may differ depending on whether the other eye is looking through a correction lens, is uncorrected, or is blocked at the same time the given eye is evaluated. Accordingly, it will be recognized that, in the binocular arrangements described herein that allow for simultaneous simulated tunable lens correction for both eyes, the procedure 1000 may be modified such that subjective settings are tested for both eyes synchronously. For example, objective wavefront-based optimized tunable lens correction settings may be made for both eyes, followed by the patient or a clinician being directed to change a dial setting that simultaneously adjusts power or another parameter for both eyes together. In this way, a fine or coarse subjective setting may be determined.

Moreover, the procedure may be modified to include appropriate clinician involvement in any case where it is undesirable or impossible for a patient alone to make adjustments to optimize settings. The values Mopt", J0opt", and J45opt" may be reported at an interface similar to the reporting interface screen 354 illustrated in FIG. 3 and used to provide a refractive prescription. Furthermore, information determined from the procedure 1000, such as final, fine subjective refractive preferences, may be provided to a patient, clinician, manufacturer via any of the means described hereinabove or other known means.

It should be understood that the procedure 1000, in other embodiments, can be extended to successively finer adjustments and determinations of subjective refractive preference. Furthermore, higher-order refractive corrections may be determined in a manner similar to that illustrated in the procedure 1000, where a particular visual tunable lens used in the apparatus permits such adjustments. Those with skill in various types of multi-dimensional, iterative optimization, as well as those skilled in the art of optometry, will understand that "coarse" and "fine" subjective settings can further be determined even where the range of optimization (e.g., 0.5 dpt or 0.2 dpt) is the same for both coarse and fine determinations. This is because there is typically value in changing all the parameters to optimize values, followed by re-optimization of the same values, whether with the same or a smaller adjustment range available to the patient.

Moreover, wavefront aberrometry measurements may be interspersed with subjective measurements in any location within the procedure 1000 for a variety of purposes. As described hereinabove, embodiments can perform adjustments of the variable focal power of the visual tunable lens or lenses iteratively in response to successive wavefront measurements to minimize wavefront errors of the light received from the eye or eyes. Wavefront measurements can be performed in a closed-loop fashion, or simply performed two or more times in between subjective measurements taking advantage of the tunable lens. One example includes obtaining an initial wavefront error measurement, setting a tunable lens to correct for the initial wavefront error, and then obtaining one or more secondary or subsequent wavefront measurements.

Performing wavefront measurements on eyes corrected by tunable lenses can allow higher-order corrections to be determined by wavefront aberrometry with greater accuracy that can be done with the same wavefront aberrometry instrument acting alone. As is known, it is useful to know higher-order corrections to apply to an eye for improved vision especially for low-light conditions and other specific cases. As such, embodiments can enable wavefront measurement accuracy commensurate with a very expensive and precise wavefront aberrometer using a relatively much more inexpensive wavefront aberrometer. Use of a tunable lens in combination with a wavefront aberrometer in embodiments can enable more accurate measurement of higher-order aberrations, even with a relatively low-cost embodiment system, because the tunable lens can correct the primary low-order aberrations, thereby cancelling out the contributions of the low-order aberration (typically much larger), thus enabling better detection of the higher-order aberrations with better sensitivity and specificity.

Moreover, embodiments combining tunable lenses with wavefront aberrometry can enable the subjective test (phoroptry) immediately after the objective wavefront aberrometry measurement in situ with the same handheld apparatus applied to the patient. This can provide better patient throughput and accuracy. Further, using embodiments, objective measurements can be performed during the subjective phoroptry measurements. In this case, the objective measurements may be used in a situation in subjective phoroptry wherein the patient indicates that it is not clear which tunable lens setting of two or more choices given is better, for example. Marks, Randall et al., "Adjustable adaptive compact fluidic phoropter with no mechanical translation of lenses," Optics Letters Vol. 35, No. 5, 739-741, Mar. 1, 2010, is hereby incorporated herein by reference in its entirety.

The international Patent Cooperation Treaty (PCT) Applications published as WO 2015/003062 A1 and WO 2015/003086 A1 are hereby incorporated herein by reference in their entireties.

Further, the teachings of all other patents, published applications and references cited herein are incorporated by reference in their entirety.

It should be understood that aspects of embodiments of the invention that are implemented in software may be stored on various types of non-transitory computer-readable media known in the art. The software may be any software that can be loaded and executed by a processor and cause various systems or devices, as applicable, to perform operations as disclosed herein or as equivalent thereto.

While this invention has been particularly shown and described with references to example embodiments thereof, it will be understood by those skilled in the art that various changes in form and details may be made therein without departing from the scope of the invention encompassed by the appended claims.

Embodiments Pertaining to the Present Disclosure

Various embodiments pertaining to the present disclosure can incorporate features described in U.S. Pat. No. 11,096, 576, the description of which is included above.

Applicants have developed technology capable of self-operation by a patient-user either with or without guidance from a telecommunicated physician/health professional/technician. A technician can be physically present or can be avoided. The physician/health professional, or alternatively, artificial intelligence in the form of executable code either local to the patient-user or remotely located, can obtain clinical-quality results (diagnosis, prescription, measurement, etc.) as to a patient's vision or other aspects of eye healthwhile the patient is physically anywhere (but wirelessly connected). Furthermore, the results can also be directly communicated to an optical retailer to facilitate instant sale of prescription eyeglasses.

FIG. 11 is a flow diagram illustrating an embodiment procedure 1100 for eye examination. At 1102, a portable optical device is delivered to a patient-user at a location outside of a clinical setting. The delivery is in a manner that enables the patient-user to have use of the device in conducting an eye examination. At 1104, corresponding executable code is provided to the patient-user. The corresponding executable code is executable with the patient-user use of the device. At 1106, during patient-user use of the device in conducting the eye examination, the corresponding executable code is executed and enables a physician to have participation in the eye examination via audiovisual means, including enabling a physician to generate a diagnosis of eye health of the patient-user.

In various embodiments that will be understood further in reference to the other drawings and description herein, the eye examination procedure 1100 can further include features as follows.

It should be noted that, as used herein, "physician" refers to a person with a degree of eye health care training such that a particular diagnosis of eye health of the patient-user can be generated based on the eye examination. Hence, it will be understood that a "physician," as used herein, can include various types of clinicians, operators, and technicians in various situations and applications of embodiments.

The location outside of the clinical setting can be remote with respect to the physician, as well as random with respect to the physician. The location can be any of a residence, a patient-specified address, a school address, a location in the community of the patient-user, a place without a health professional present, a kiosk, a place of employment, and an optical restore retail store.

The corresponding executable code can be provided to the patient-user by any of: being preloaded on the portable optical device, being preloaded on a portable digital processing device, or being available for download by the patient-user from a cloud server, such as illustrated in FIG. 29, through a website, or through an online platform.

The corresponding executable code can include two or more executable code modules, such as one that is executable on the portable optical device, and another that executes on a cloud server or another device, such as a tablet computer, that is delivered to the patient-user along with, or supplemental to, the portable optical device.

The preloaded portable digital processing device can be a laptop, notebook, tablet, digital health wearable, or mobile phone included in the delivery of the optical device to the patient-user. The corresponding executable code can be downloaded by the patient-user to a computer, laptop, notebook, tablet, digital health wearable, or mobile phone of the patient-user or accessible by the patient-user.

Figure 18:
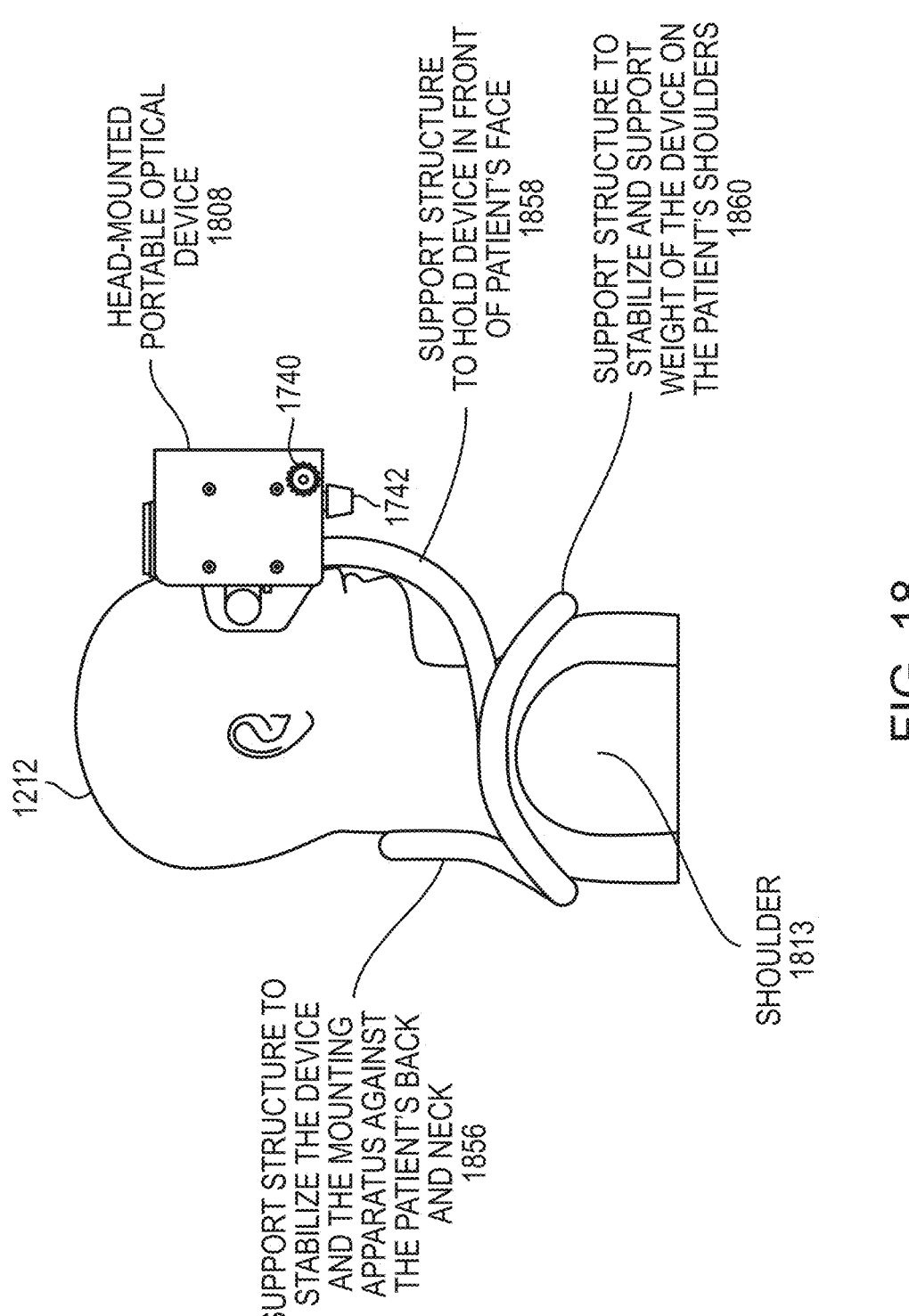
FIG. 18 is a color diagram showing use of a shoulder-mounted portable optical device according to embodiment methods and systems.
Figure 19:
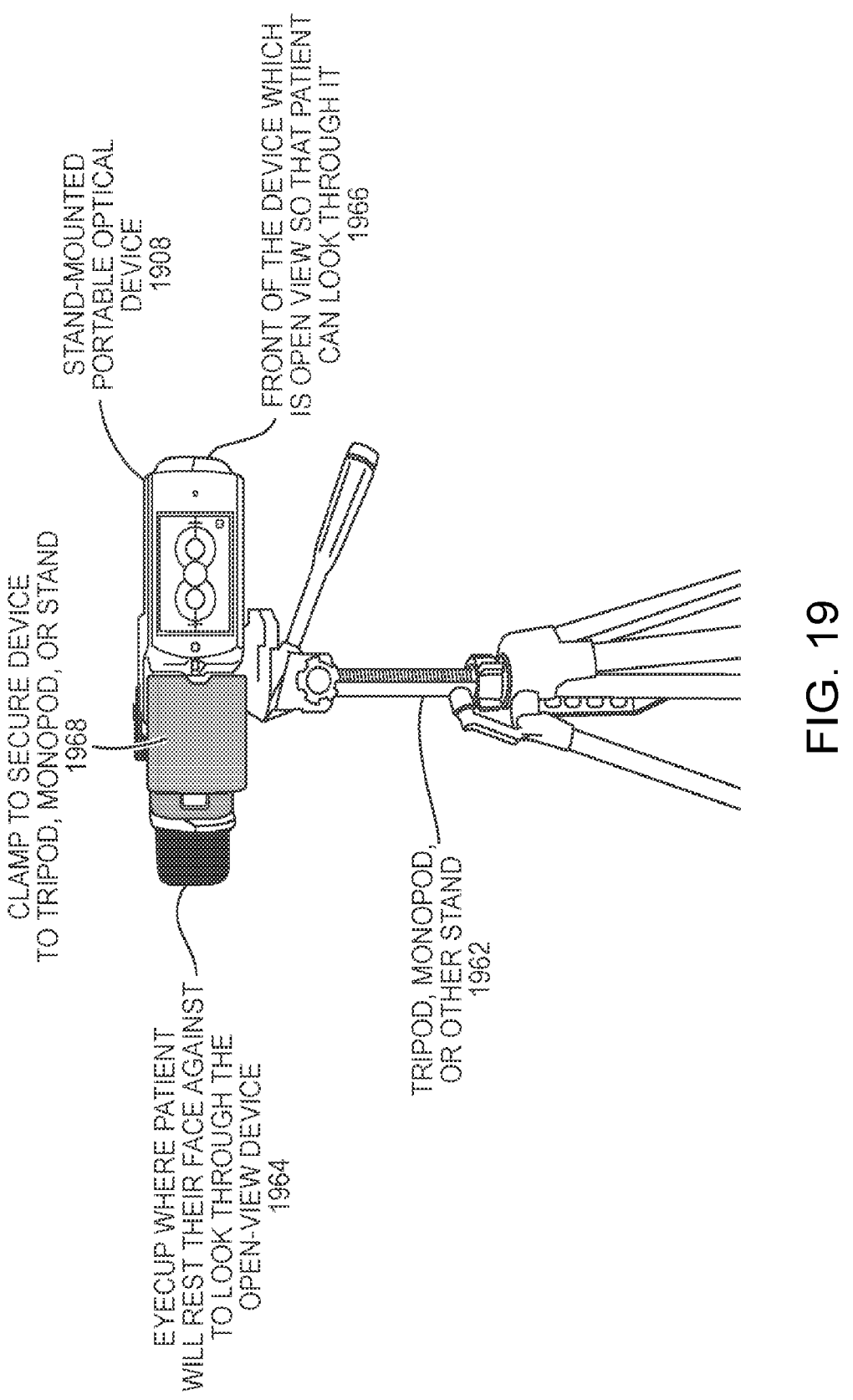
FIG. 19 is a diagram illustrating a stand-mounted portable optical device that can be used to maintain alignment with a remote patient-user consistent with embodiments.

The portable optical device can be configured to be shoulder-mounted to a shoulder of the patient-user, as illustrated in FIG. 18, head-mounted to a head of the patient-user, as illustrated in FIG. 17, or stand-mounted, such as mounted on a tripod, during the eye examination, as illustrated in FIG. 19, for example.

The portable optical device can include a pupil camera, such as that illustrated in FIG. 20, and the corresponding executable code can be configured to assist in aligning, or in maintaining alignment of, one or more optical elements of the portable optical device with a pupil of an eye of the patient-user. Example drawings that illustrate aspects of such a pupil camera and alignment procedure include FIGS. 21-25, as well as FIG. 26, for example.

There are several alignment indicators that can be provided in executable code such as software that enable alignment including use of: (i) a pupil tracking algorithm to identify and display the location of the pupil on the display screen, (ii) an orientation detection algorithm that evaluates the intensity of the individual LEDs and determines if there are differences above a threshold which will indicate whether the device is tilted or yawed with respect to the patient's eye (particularly helpful since misalignments between the optics of the device and the patient's eye can induce astigmatism in the measurements), (iii) a patient-device distance algorithm which can include using autofocus algorithms, factory calibration files, or machine learning on ocular and facial features at various distances, which will estimate the distance from the eye to the device.

Maintaining the alignment can include maintaining the alignment for a sufficient time for the portable optical device to acquire a temporal sequence of wavefront aberrometry measurements of the eye. Furthermore, the maintaining the alignment can be for a sufficient time to obtain a subjective refraction preference of the patient-user while the patient-user views one or more external target indicia through at least one visual tunable optical element of the portable optical device, such as a tunable optical lens, as illustrated in FIG. 20 and in FIG. 1, for example. Maintaining the alignment can further be for at least three seconds, five seconds, 10 seconds, 20 seconds, or 30 seconds.

As part of maintaining alignment, the device can tracks the position of the pupil continuously during the wavefront aberrometry measurement, the orientation of the device with respect to the patient's eye, and the distance from eye to device's optics. If the device or the software operating it (on the device or in the cloud or at the edge) detects a momentary misalignment then the software can be configured to inform the operator or the patient (or the motors) through the user interface and can provide indications on how to readjust the alignment.

The portable optical device can include one or more manual adjustments that are configured to permit the patient-user, or an operator, to adjust alignment of the one or more optical elements of the portable optical device with an eye of the patient-user. Such manual adjustments are illustrated in FIGS. 17-18, for example. Alternatively, the corresponding executable code can be configured to cause one or more electric electromechanical actuators, such as motors, to adjust or maintain the alignment, using apparatus that is similar to that described in connection with FIG. 17-18, but including motor actuation instead of manual adjustments of the lead screw and knob, for example.

Figure 15:
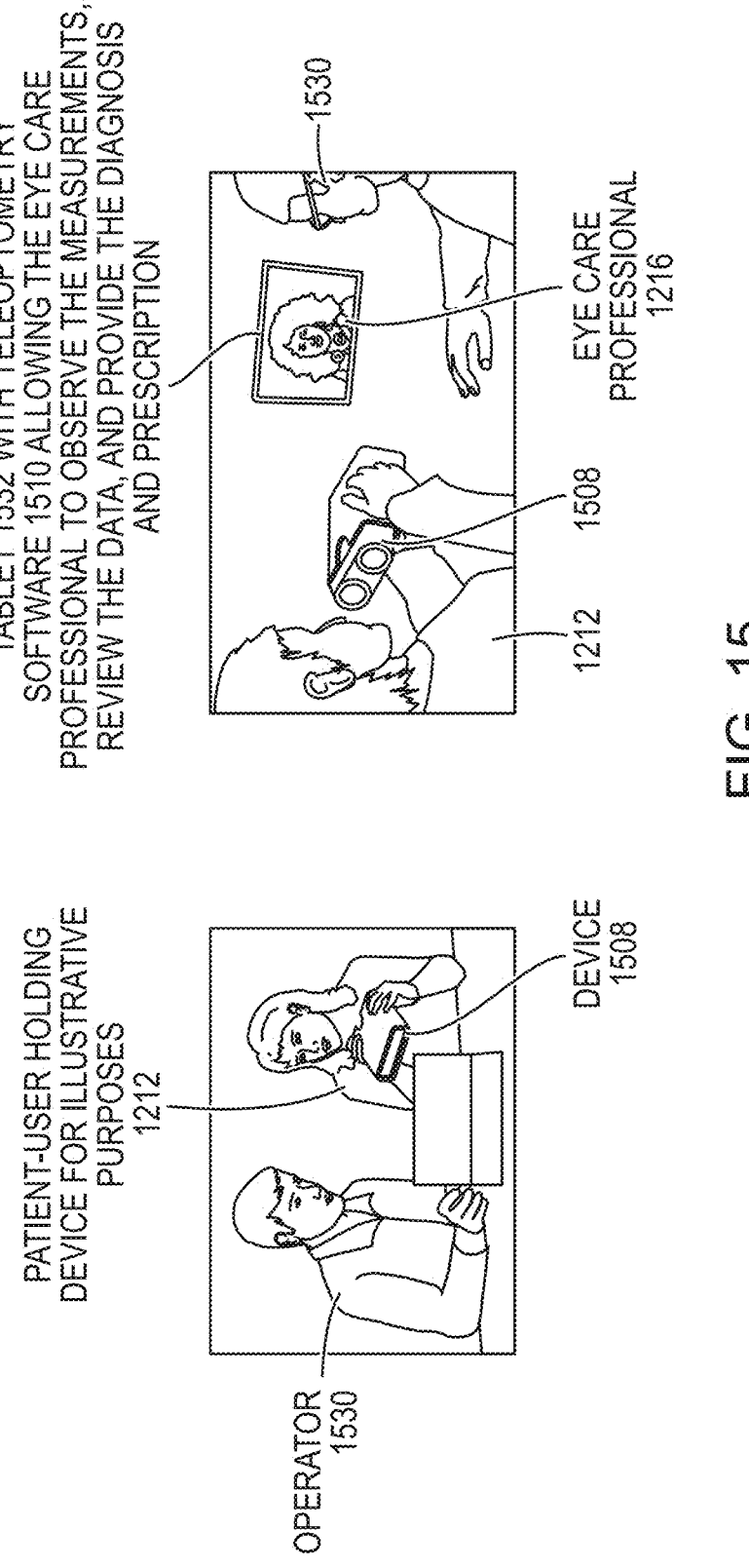
FIG. 15 provides photographs showing an example of a technician, parent, store clerk, or other operator assisting a patient to be measured remotely according to embodiments.

The portable optical device can be configured for self-operation by the patient-user with or without an assisting operator, such as the operator illustrated in FIGS. 15 and 25.

The portable optical device can include a wavefront aberrometer, such as the wavefront sensor 116 described in connection with FIG. 1. The portable optical device can determine an optical property of an eye of the patient-user, such as refractive error or an initial refractive prescription, based on data from the wavefront aberration. This may be done, for example, via the execution of the executable code, which can perform, with with proper configuration that will be understood in view of this disclosure, all of the functions that are described for operators and physicians or other clinicians herein.

Determining the optical property based on data from the wavefront aberrometer can include fundus imaging or corneal imaging based on the data from the wavefront aberrometer. The optical path of the FIG. 1 or 2 (QuickSee™)

apparatus can be modified to include additional beamsplitters, diffusers, LEDs, as described at paragraphs 20-21, 25, 31-32 and 52, and FIGS. 1A/1B, 1G, and 1K of PCT Pat. App. Pub. No. WO2020/010138 (hereinafter "Johns Hopkins publication," which is hereby incorporated herein by reference in its entirety. This will enhance QuickSee™ Plus optics and hardware to enable a wider measurement range and pupil imaging. Specifically, the Shack-Hartmann lenslet array employed in the QuickSee™ Plus optical channel can be replaced by a diffuser, with a pre-defined or random speckle pattern (sometimes referred to as a caustic pattern), to perform diffuser-based wavefront aberrometry. The diffuser's caustic or speckle pattern is unique and enables registration of large displacements, which enables a larger measurable range (in terms of diopters) than other wavefront aberrometry approaches that use a pinhole or lenslet-array based wavefront sensor.

By incorporating different wavelength (visible color such as Blue, Green, Red) LEDs into QuickSee™ Plus's optical channel, and appropriate beamsplitters, and an image sensor capable of detecting the visible color LEDs (e.g., RGB sensor), QuickSee™ Plus can perform computational light-field ophthalmoscopy to image the retina, cornea, or lens. By simultaneously, or at almost simultaneously time intervals such as 0.1 seconds, 1 seconds, or less than 1 minute, or in a sequential manner, the light from the visible colored LEDs can be reflected by the beamsplitters specific to that wavelength of light, and then directed into the patient's eye. This will allow imaging of the fundus, which includes the retina, optic disc, macula, fovea, and/or the posterior pole. By using optical lens, or the tunable lens, in front of the specific LED or at the port closest to the patient's eye, a different visible colored LED (e.g., green) can be focused (the beam sizes can be modulated) to illuminate different portions of the eye, for instance, the entire anterior segment of the patient's eye to inspect the cornea. As another example, the visible color LED with the narrowest beam can be used for wavefront aberrometry after being reflected by the appropriate beamsplitter and being directed into the eye, with the return light being directed to the wavefront sensor. The light reflected and/or remitted from the patient's eye are emerging wavefronts that may bounce off of an appropriate beamsplitter to the wavefront sensor having a multi-channel image sensor (e.g., RGB sensor), which can capture the multiple caustic or speckle patterns. Multiplexing these different colored caustic or speckle patterns enables simultaneous or nearly simultaneous or sequential wavefront aberrometry measurements and high-quality images of the anterior and/or posterior segment of the eye in a synergistic manner.

The QuickSee™ Plus software/firmware function described at 144, 145, 146, 147 path of FIG. 1 or 2 can be modified to include additional beamsplitters, diffusers, LEDs, as described at paragraphs 23-24, 25, 27-28, 37-41, and FIGS. 1C, 1E, 1F, 1H, 1I, 1J of the Johns Hopkins publication. This will enhance QuickSee™ Plus software/firmware to enable a wider measurement range and pupil imaging. Specifically, the image registration can be performed on the caustic of speckle images in comparison to a reference image. This process can utilize one or more well-known non-rigid image registration algorithms such as Demon's algorithm (including hyperparameter tuning), three-dimensional grid search for optimal parameters, a quantity of algorithm iterations, threshold-based approaches examining the reference image and test image for correlations, or determining a displacement matrix between pixels in the reference image and the test image. Machine learning/deep learning approaches can be employed to perform image registration and Zernike polynomial fitting. (1+1) Evolutionary optimization may also be performed.

The portable optical device of FIG. 11 can further include one or more visual tunable optical elements, and enabling the patient-user use can include enabling the patient-user to have an open view through the one or more visual tunable optical elements and through the portable optical device during the eye examination. The corresponding executable code is can be configured to determine a subjective refractive preference of the patient-user, also, during the eye examination, based on the open view of the patient-user. Open view and visual tunable optical elements, such as visual tunable lenses, are described extensively in connection with FIGS. 1-10B, for example.

The corresponding executable code can be configured to stream wavefront aberrometry data from the portable optical device to the physician via the audiovisual means, enabling the physician to generate a refractive correction or an eyeglass or contact lens prescription. The code can also be configured to generate keratometry data for an eye of the patient-user based on the eye examination with the portable optical device. The keratometry data can be based on pupil imaging data from a pupil camera on the portable optical device, such as the pupil camera illustrated in FIG. 20. The portable optical device can be of a binocular or monocular design, and can provide the patient-user an open view toward target indicia that are external to and spaced away from the portable optical device.

Specific example keratometry data that kan be provided include 'H' the horizontal axis of the circular or elliptical pattern, 'V the vertical axis of the circular or elliptical pattern, 'Avg' the mean of H and V, and 'Cylinder' the power of the corneal astigmatism.

The method or procedure 1100 of FIG. 11 can also include initiating an order for eyeglasses or contact lenses using a physician generated eyeglass or contact lens prescription that is based on data received from the portable optical device. Alternatively, in other embodiments, artificial intelligence in the executable code can be configured to initiate such an order, or to generate an eyeglass or contact lens prescription based on data received from the portable optical device.

FIG. 12 is a schematic block diagram illustrating an embodiment eye examination system 1200, corresponding to the eye examination procedure 1100 of FIG. 11. The system 1200 includes a portable optical device 1208, as well as corresponding executable code 1210. The portable optical device is delivered to a patient-user at a location outside of a clinical setting. The device is delivered in a manner that enables the patient-user to have use of the device in self-operating and conducting an eye examination of an eye of the patient-user. The corresponding executable code is executable with the patient-user use of the device, during patient-user use of the device conducting the eye examination, namely the device 1208. The corresponding executable code 1210 is executed and enables physician participation in the eye examination via audiovisual means, including enabling a physician to generate a diagnosis of eye health of the patient-user.

The eye examination system 1200, with its portable optical device 1208 and corresponding executable code 1210, can have any of the features described in connection with FIG. 11, such as random and remote location with respect to the physician, any of the cited example locations, preloading the corresponding executable code, using a portable digital processing device, and downloading the corresponding executable code in the various ways cited.

Moreover, the portable optical device can include a wavefront aberrometry and is can be of a binocular or monocular, open-view design such that the portable optical device determines optical properties of each eye of the patient-user.

In an alternative embodiment that is also consistent with FIG. 12, the portable optical device 1208 can be delivered to a patient-user at a location outside of a clinical setting, with the device being delivered in a manner enabling the patient-user use of the device in conducting an eye examination. The corresponding executable code that is executable with the patient-user use of the device can be executed and enable physician participation in the eye examination via audiovisual means during patient-user use of the device conducting the eye examination. Such enablement of physician participation can include enabling a physician to generate a diagnosis of eye health of the patient-user. In this embodiment, also, the portable optical device and the corresponding executable code can include any of the features described herein above in connection with the procedure 1100 or the system 1200.

FIG. 13 is a flow diagram illustrating an eye examination procedure 1300 according to an embodiment. At 1322, a portable optical device is delivered to a patient-user at a location outside of a clinical setting. The delivery is in a manner that enables the patient-user use of the device in conducting an eye examination of one or both eyes of the patient-user. At 1324, the patient-user is provided with corresponding executable code that is executable with the patient-user use of the device. The code provides uploading and live streaming of optical measurement data to a health professional as a function of type of optical measurement data or health consideration of the patient-user. The corresponding executable code also enables anyone or combination of light streaming of optical measurement data during patient-user use of the device conducting the eye exam, and uploading optical measurement data from patient-user use of the device such that the optical measurement data is received and reviewed by the health professional in a manner that enables the health professional to generate any one of: a diagnosis of a health for the patient-user, a refractive correction for the patient-user, an eyeglass prescription for the patient-user, and a contact lens prescription for the patient-user.

In particular detail, the procedure 1300 can include the following optional features. The optical measurement data type can include any of: wavefront aberrometry data, wavefront aberrometry data in the form of Zernike coefficients or spot diagram images; image quality metrics (IQMs) such as retinal IQMs; cornea curvatures; optical refractive power; final refractive care prescriptions; axial length (distance from the corneal surface to an interference peek corresponding to the retinal pigment epithelium Bruch's membrane) or other biometric data; fundus imaging; or corneal imaging.

The corresponding executable code can upload the optical measurement data to the health professional at a different time than the patient-user conducting the eye examination using the device. The code can further support a conferencing session between the patient-user and a health professional with respect to the optical measurement data. The conference session can be a videoconference session in which the optical measurement data is light streamed from the device to the health professional, and simultaneously, the health professional and patient-user converse to arrive at the eyeglass prescription. In addition, it should be understood that the procedure 1300 can further include any of the features described in connection with FIGS. 11-12.

As used herein, "health professional" means the same and has the same scope as "physician," as detailed herein above.

FIG. 14 is a flow diagram illustrating an embodiment eye examination procedure 1400. At 1426, a portable optical device is delivered to a patient-user at a location outside of a clinical setting, with the delivering being in a manner that enables the patient-user to have use of the device in conducting an eye examination of one or both of the patient-user's eyes. At 1428, corresponding executable code is provided that is executable with patient-user use of the device. The code is configured to be in operative communication with the device during the patient-user use and to determine a degree of alignment of the portable optical device to an eye of the patient-user during the patient-user use. The portable optical device includes a pupil camera and the corresponding executable code is configured to assist in aligning and maintaining alignment of one or more optical elements of the portable optical device with a pupil of an eye of the patient-user, based on images from the people camera. This maintaining alignment is done for a sufficient time for the portable optical device to acquire a temporal sequence of wavefront aberrometry measurements of the eye.

The operative communication may be within the device, such as over a bus, or over wired or wireless communication within the device. Corresponding executable code may be stored on the device and they operate in a processor on board the device; or the code may be stored on and/or executed on, a cloud-based device such as a cloud server. Some of these features are described in connection with FIG. 29, for example.

The procedure 1400 can also include the portable optical device having one or more visual tunable optical elements. Enabling the patient-user use can include enabling the patient-user to have an open view through one or more of the visual tunable optical elements and through the portable optical device, for an open view, during the eye examination. The corresponding executable code can be configured to determine a subjective refractive preference of the patient-user during the eye examination based on the open view of the patient-user. An example over open view devices illustrated in FIG. 20, for example. The code can further be configured to provide an indication of the degree of alignment to the patient-user for a manual patient-user adjustment of the alignment, such as by means of visual feedback as illustrated in FIGS. 21-22, or audio feedback. Audio feedback for a different purpose has been described in connection with FIGS. 1-10B but may be adapted for this purpose in the present embodiments.

The corresponding executable code can be further configured to control the alignment via one or more electromechanical actuators. The corresponding executable code can be further configured to determine the degree of alignment based on a pupil image of the eye from a pupil camera on the device, such as illustrated in FIG. 20, for example. The executable code can be cloud-based software or code that is implemented within the device portable optical device, such as firmware or software. The code can be configured to process a wavefront image of the eye, where the wavefront imaged is received from the portable optical device. Wavefront image processing has been described further in connection with FIGS. 1-10B. The corresponding executable code can be further configured to enable generation of a diagnosis of eye health of the patient-user. The diagnosis can include a refractive prescription for eyeglasses or contact lenses, but the diagnosis can also include retinal imaging based on a wavefront image of the eye acquired by the portable optical device. The diagnosis can include presentation or use in diagnosis of keratometry measurements based on one or more images from the pupil camera. The code can be configured to determine a subjective refractive preference of the patient-user during the eye examination with the patient-user having an open view through the portable optical device. The code can be further configured to generate a contact lens prescription for the patient-user based on the subjective refractive preference and on the keratometry.

Maintaining the alignment can further include maintaining for a sufficient time to obtain a subjective refractive preference of the patient while the patient views one or more external target indicia through at least one visual tunable optical element of the portable optical device, as illustrated in FIG. 20, for example. Maintaining the alignment can be for at least three seconds, at least five seconds, at least 10 seconds, or at least 20 or 30 seconds.

The portable optical device can be configured to be shoulder-mounted to a shoulder of the patient-user, head-mounted to ahead of the patient-user, or stand-mounted (e.g., via a tripod) during the eye examination.

The device can include one or more manual adjustments that are configured to permit the patient-user or an operator to adjust alignment of one or more optical elements of the portable optical device with the eye of the patient-user. Alternatively, the corresponding executable code can be configured to cause one or more electromechanical actuators to adjust or maintain the alignment, or both.

It should be understood that the procedure 1400 can further include any of the features described in connection with FIGS. 11-13.

FIG. 15 includes photographs illustrating an example of an operator 1530, who can be a technician, parent, or store clerk assisting a patient-user 1212 to be measured with a portable optical device for an eye examination, outside of a typical clinical setting. The portable optical device 1508 can be similar to the apparatuses described in connection with FIGS. 1-10B, for example. However, the device 1508 can include other features described in the present embodiments in connection with FIGS. 12-29, for example. In FIG. 15, a tablet computer 1532 includes tele-optometry software 1510 that allows an eye care professional 1216 to observe the measurements, review the data, and provide the diagnosis and prescription to the patient-user 1212.

Illustrated in FIG. 15 are the key elements and aspects of an embodiment of the present invention. Of note are: (1) a clinical-grade portable equipment for conducting an eye or vision exam such as, but not limited to, QuickSee™/Quick-See™ nano/QuickSee™ Plus (and its associated features) by PlenOptika, Inc. (Assignee);

(2) an exam setting that is not of necessity in a clinical location but rather any location, or possible random locations outside of clinical locations;

(3) a remote physician/health professional/technician or artificial intelligence capable of authorizing the prescription by measurements obtained on the portable equipment participating by video conference (as shown on the notebook screen). Corresponding software executing on the notebook, in some embodiments, may allow the physician/health professional/technician to have a direct feedback from the portable equipment, i.e., (i) see the pupil camera in a standard autorefractor to check centration and to give indications to the operator, or (ii) be able to start the measurements with the portable equipment (or otherwise control the portable equipment);

(4) self-operation of the portable equipment by the patient (or patient with assisting operator, such as a child patient with assisting adult as shown) with or without guidance from remote technician/physician/health professional or artificial intelligence. In embodiments, operation of the portable equipment on the patient (taking measurements and images of the patient's eyes and ocular system) may be at a different date/time than that of the remote video session with the physician/health professional/technician.

Given the above, advantageously, the patient does not need to travel to where the traditional clinical equipment is, and the physician/health professional/technician does not need to be co-located with the patient and portable optical equipment. In addition, output of the portable equipment (measurements of optical properties of the eye, images of the eye, etc.) can be of a clinical quality and form that enable a physician/health professional/technician or artificial intelligence (even when remotely located from the patient) to generate: a diagnosis of eye health/vision acuity, a refractive correction, and/or an eye glass prescription.

For wavefront aberrometry measurements to be of enhanced accuracy, the light source must pass through the patient-user's pupil, which can be 1.5 mm to 8 mm on average, during the initial measurement and during the subjective refraction and vision correction portion of the vision (eye) exam. To achieve this level of precision over a prolonged exam period, it is advantageous to have: (1) a pupil camera to understand if the position of the optics relative to the pupil is correct and allows the wavefront aberrometry light source to pass through the pupil; (2) the position of optics of the device be adjustable relative to the patient-user's pupil, either manually by the operator or patient, or automatically (mechanized and automated) by the remote physician/technician or artificial intelligence; (3) the device must be stably mounted to the patient's pupil and face via a head or shoulder mount or via a stand, which enables the measurements to be taken and visual acuity and subject refraction preference to be maintained even while the patient looks around, thus ensuring a natural viewing experience to evaluate the corrective prescription. These and other advantages of embodiments of the present invention are made evident by the disclosure herein.

In the course of patient care or otherwise, a patient may need an eye examination. The physician/health professional and patient coordinate logistics of the eye examination, in particular, an appointment date and time for the exam. Where the patient resides in a fairly remote area from the physician/health professional's office or a suitable clinic, embodiments of the present invention are employed. FIG. 16 is illustrative. In response to the physician/health professional order or patient request specifying the appointment date/time for the eye examination, a fulfillment center prepares a portable optical device 1508 and corresponding software 1510 that together enables the patient to conduct the eye exam from the comforts of his home (or his preferred location) and outside of a clinical setting.

The portable optical device 1508 is any of those, or equivalents, as mentioned above with respect to FIG. 15 (a binocular, open-view design having a wavefront aberrometer and tunable optics to test and simulate vision-correcting optics, such as eyeglasses or contact lenses, pupil camera, keratometer for contact lens fitting) or described in US Application Publication no. 2020/0046222 by Shivang R. Dave et al, U.S. Pat. No. 9,854,965 by Nicholas J. Durr et al, and U.S. Pat. No. 10,786,150 by Nicholas J. Durr et al (each incorporated herein in their entireties), for non-limiting example. Restated, the portable optical device 1508 is configured to determine optical properties of the eye. The portable optical device is of a hand-held or equivalent design and configuration. That is, the weight and overall shape and size of the optical device are conducive to operating and using the optical device by holding it in one's hands, or by removably securing it to an optional stabilizing and leveling stand (for table top or floor), or bracket system, or a head- or shoulder-mounted optical device, and the like. The portable optical device 1508 is designed for self-operating and effectively self-conducting an eye (vision) exam. As used herein "self-operating" and "self-conducting" an eye (vision) exam using the optical device may include another onsite operator assisting in taking measurements using the optical device on the patient-user. Thus, the portable optical device 1508 may be positioned (held) and operated by the patient-user in conducting his own eye exam, or may be positioned (held) and operated by an assisting operator conducting an eye exam on the patient (such as a parent, relative, caregiver, and the like using the optical device on a child).

The corresponding software 1510 in one embodiment is as outlined in FIG. 16. The corresponding software has identifier credentials for pairing with the portable optical device 1508 using Bluetooth protocol or other wireless connection. Other coupling or wired connections are suitable. The corresponding software 1510 has a video conferencing link configured for communicating with the physician/health professional/technician or artificial intelligence on the specified appointment date/time. In particular, in some embodiments corresponding software 1510 utilizes common known video/audio conferencing technology or videotelephony technology such as found in FaceTime® (by Apple® Inc), Zoom (by Zoom® Video Communications, Inc.), Microsoft® Teams, and the like. Other proprietary videotelephony software, third-party software, and the like are suitable.

In one embodiment, the fulfillment center preloads the corresponding software 1510 on a notebook, laptop, tablet, digital health wearable (watch), mobile phone, or other portable digital processing device. The fulfillment center packages the portable optical device 1508 and the notebook (with the corresponding software 1510 preloaded in memory) for shipment to the patient's home or desired location for use. The shipment destination/use location may be any patient specified location which is remote from the physician/health professional's office or clinic and which is outside of a clinical setting. For non-limiting example, the location of patient use of the portable optical device 1508 and corresponding software 1510 may be any of: a residence, a patient-specified address, a school address, a location in the community of the patient-user, a clinic without a physician/health professional present, an optical retail store, a workpace of the patient-user, a kiosk, and the like. The term "kiosk," as used herein is in its customary and ordinary sense and meaning in commerce, such as kiosks providing information or consumer products or services in a mall, store, amusement park, or on the street, for example.

In other embodiments, the corresponding software 1510 may be accessible to the patient via a mobile application, through a cloud server, through a website, or an online platform. The patient downloads a copy of the corresponding software 1510 onto his mobile phone, digital health wearable (watch), computer (desktop or laptop), or other digital processing device. In these instances, the fulfillment center does not need to include the notebook/portable digital processing device (having the corresponding software 1510 preloaded in memory) with the shipment of the portable optical device 1508.

Upon patient receipt of the portable optical device 1508 and notebook (or corresponding software 1510), the patient and/or assisting operator are prepared to conduct the subject eye exam taking measurements using the portable optical device 1508 on or before the appointment date/time. FIG. 12 outlines the flow of control and data as occurs during use of the portable optical device 1508 and notebook/corresponding software 1510. FIG. 16 is for purposes of illustration of one embodiment and not for limitation of embodiments. Other embodiments and variations are in the purview of one skilled in the art.

The patient or assisting operator powers on the portable optical device 1508. The patient/assisting operator logs on to the notebook. The notebook executes (runs) the corresponding software 1510. In turn, the notebook establishes a Bluetooth or similar wireless connection with the portable optical device 1508. The patient/assisting operator takes measurements of the subject eyes using the portable optical device 1508. Through the wireless connection (Bluetooth or other communications protocol), the notebook/corresponding software 1510 stores the measurements from the optical device 1508 in computer memory.

On the appointment date/time, which may be separate from the time of the patient/assisting operator taking measurements of the subject eyes using the portable optical device 1508, the patient/assisting operator initiate and enter the video conference session utilizing the call link preprogrammed into the notebook/corresponding software 1510. If measurements have not yet been taken using the portable optical device 1508, then following physician/health professional/technician or artificial intelligence instructions for operating the portable optical device 1508, the patient/assisting operator conduct an eye (vision) exam. The portable optical device 1508 feeds optical measurement data, images, etc. to the notebook/corresponding software 1510 over the established wireless connection. The notebook/corresponding software 1510 receives the optical measurement data as exam results and uploads the same to the video conference session for receipt by the physician/health professional/technician or artificial intelligence in the form of software or firmware running in the cloud or on the device or on a separate patient-user or provided device, for example. The corresponding software 1510 may also upload any of the previously stored exam data (optical measurements, images, etc.) from notebook memory to the video conference session for receipt and review by the physician/health professional/technician.

The scope of optical measurement data and exam results that may be uploaded to the physician/health professional/technician or artificial intelligence executable code, for example, whether during the exam process (use of the portable optical device 1508) or afterward, is broad. Example types of optical measurement data and exam results can include wavefront aberrometry data in the form of Zernike coefficients or spot diagram images; image quality metrics (IQMs) such as retinal IQMs; cornea curvatures; optical refractive power; final refractive care prescriptions; biometric data such as axial length (distance from the corneal surface to an interference peak corresponding to the retinal pigment epithelium/Bruch's membrane); fundus imaging, or retinal imaging.

Further, the corresponding software 1510 may stream the optical measurement data via the video conference communications connection for real-time viewing by the physician/ health professional/technician while the patient-user/assisting operator operate the portable optical device 1508. In embodiments, the corresponding software 1510 live streams the optical measurement data as a function of type of measurement/exam data or health considerations of the patient as further made clear below.

At the physician side, on the appointment date/time, the physician/health professional/technician hosts or otherwise logs into the video conference session. Through the video conference session, the corresponding software 1510 allows the physician/health professional/technician or artificial intelligence to have direct feedback from the portable optical device 1508 operating at the patient side. For non-limiting example, the corresponding software 1510 allows the physician/health professional/technician or artificial intelligence to see the pupil camera in a standard autorefractor to check centration and to give indications and further instructions to the patient/assisting operator or to automated electro-mechanical actuators such as motors controlled by software or artificial intelligence at this time. In some embodiments, the corresponding software 1510 may allow the physician/health professional/technician to start (initiate) the taking of measurements or otherwise control operation of the portable optical device 1508. In embodiments, the corresponding software 1510 live streams aberrometry data, pupil camera, keratometry, and/or subjective refraction results (patient preference for and visual acuity with uncorrected or correction applied with the tunable lenses) from the portable optical device 1508 operating at the patient side in a manner enabling the physician/health professional/technician or artificial intelligence to arrive at a refractive correction or eye glass prescription for the patient having dialogued during the video conference session. That is to say, the video conference connection enables live streaming (or other upload) of optical measurement data together with (simultaneous with) conversing between patient and physician/health professional/technician or artificial intelligence. Thus the physician/health professional/technician or artificial intelligence views visually or otherwise analyzes the optical measurement data streamed over the video component of the video conference connection and converses with the patient effectively over the audio component of the video conference connection.

At intermittent times between patient appointments, the physician/health professional/technician or artificial intelligence may want to monitor an eye condition of the patient. In such use of embodiments, the corresponding software 1510 is programmed to record and store in notebook memory the optical measurement data from patient use of the portable optical device 1508 at the physician prescribed frequency of use. The corresponding software 1510 can upload the stored optical measurement data from the notebook memory to a server of the physician/technician or artificial intelligence. The uploading can be outside of (without respect to) a video conference session and is distinct from live streaming during patient/assisting operator use of the portable optical device 1508 in a video conference session. The uploading can be by command of the patient/assisting operator or artificial intelligence at suitable times, or by command of the fulfilment center at a subsequent time as described further below.

Alternatively, the uploading can be with respect to a video conference session. For non-limiting example, for the eye condition of the patient, the physician/health professional/technician or artificial intelligence prescribes monitoring by the patient taking and uploading to the physician or artificial intelligence side server optical measurements from the portable optical device 1508 weekly for five weeks. For the following clinical use cases to monitor diseases and treatments for myopia management, LASIK or cataract surgery follow-up, or dry eye monitoring retinal diseases (using the teachings of U.S. Pat. No. 11,096,576, granted on Aug. 24, 2021, and the teachings of PCT Pat. App. Pub. No. WO2020/010138, filed on Jul. 2, 2019, both of which are hereby incorporated by reference in their entireties.) For each of the first four weeks, the patient-user or assisting operator operates the portable optical device 1508, saves the optical measurements to notebook memory, and uploads the optical measurements to the physician-side server from the notebook memory. In turn, the physician/health professional/technician or artificial intelligence reviews/analyzes the received optical measurement data for changes in the eye condition, progression of healing, or the like. On the fifth week, the patient/assisting operator conducts the eye exam using the portable optical device 1508 and saves the exam results/optical measurement data in the notebook memory. Just before or at the time of the scheduled video conference appointment, the patient/assisting operator uploads the optical measurement data from notebook memory to the physician-side server as illustrated in FIG. 16. Sharing of the optical measurement data from the notebook memory during the video conference is in contrast to a live stream feed directly from the portable optical device 1508 while in use. The physician/health professional/technician or artificial intelligence can nonetheless converse with the patient/assisting operator via the planned video conference session regarding the outcome of the monitoring and assessment of the five weeks of optical measurement data.

In the forgoing ways, the corresponding software 1510 can be programmed to provide live streaming and uploading of optical measurement data to the physician's server as a function of type of measurement data and/or health condition(s) of the patient.

Continuing with FIG. 16, the physician/health professional/technician or artificial intelligence may review/analyze the eye exam results as uploaded from the notebook/corresponding software 1510 during the video conference session, outside of the video conference session, or both. From his review and assessment, the physician/health professional/technician or artificial intelligence generates a diagnosis. For non-limiting example, the physician/health professional/technician or artificial intelligence generates a refractive correction or an eye glass prescription for the patient. The physician/health professional/technician or artificial intelligence generated eye glass prescription may be electronically communicated to an eye glass source for the patient to order eye glasses. In this way, an eye glass order is initiated by the patient in the illustrated system of FIG. 16.

At the end of the appointment, the patient/assisting operator and physician/health professional/technician exit the video conference session, or artificial intelligence can cease communicating with the portable optical device or the patient-user. The patient/assisting operator powers off the portable optical device 1508 and closes the running apps (e.g., corresponding software 1510) on the notebook. The patient/assisting operator logs off and powers down the notebook. The patient/assisting operator packs the portable optical device 1508 and the notebook in a return package to the fulfillment center for: (i) download and forwarding to the physician/health professional/technician or artificial intelligence the optical measurement data/eye exam results saved in memory (in the case where the optical measurement data was not previously uploaded to the physician/health professional/technician as indicated by the corresponding software 1510), and (ii) reuse with another patient and his physician/health professional.

FIG. 17 is a color illustration showing various views of an embodiment head-mounted portable optical device 1708 in use on the head of the patient-user 1212 in order to perform an eye examination of one or more eyes 1754 of the patient-user. A head strap 1734 for the top of the head, together with a head strap 1736 for the side of the head, assists in securing the device 1708 to the head such that alignment between optics optical channels 1752 of the device and eye pupils of the patient-user can be maintained during an eye examination stably, even if the patient-user turns in a different direction. The device 1708 includes a horizontal rail carriage 1744 that attaches the device the optics of the device to a rail system 1746 to allow translation along the horizontal axis of the page, which can be considered to be the X axis. Lead screws and knobs 1740 and 1742 provide for the patient-user, or an operator, to translate the optical channel 1752 along the horizontal x-axis and the vertical y-axis, respectively, to achieve more perfect alignment of the optical channel with a pupil of an eye of the patient. The straps 1734 in 1736 are secured to the device by means of an attachment mechanism 1738.

FIG. 17 shows the device (wavefront aberrometry with tunable lens optics) wherein the optics, in particular the optical channel, are adjustable relative to the patient's pupil. In this example, the optics are manually adjustable using the knobs (blue), and the device is head-mounted. It would also be possible to manipulate the knobs through the use of motors, which would facilitate automatic adjustments (as determined by software) or remote adjustments (by an off-site operator). The open-view design allows the patient to see through the device at objects outside of the device. While the open-view design is preferable for a more natural viewing experience and to reduce measurement errors due to accommodation, a closed-view design would also be possible, especially if paired with fogging techniques.

The optical channel (red) of the device is attached to a rail carriage (yellow) which is guided by a rail system (green), and is moved by a lead screw with a knob (blue). It can be appreciated that this occurs in both the X and Y directions, and can also be implemented for the Z direction (along the optical axis of the device and patient's eye). Together these allow the position of the optical channel to be adjusted relative to the patient's eye.

FIG. 18 is an illustration of an embodiment shoulder-mounted portable optical device 1808. The device includes wavefront aberrometry with tunable lens optics common, wherein the optics, in particularly, the optical channel (not shown in FIG. 18), are adjustable relative to the patient's pupil, just as illustrated in FIG. 17. In the example of FIG. 18, the device weight is supported by the patient-user's shoulder 1813, and the device is stabilized relative to the patient-user's face with an upper support structure 1858. Further stabilization is provided by the support structure 1860, which stabilizes and supports weight of the device on the patient shoulders, and a support structure 1856, which stabilizes the device and the mounting apparatus against the patient's back and neck. In this manner, the devices stabilize relative to the patient-user's face with the support structures touching the patient-user's back and neck, and may also be touching the chest neck and chin.

Thus, alignment of optics to the pupil may be stably maintained during wavefront measurements as needed, such as to obtain a temporal series of wavefront measurements, or for sufficient time to obtain both wavefront measurements and subjective refractive preference of the patient, or for as long as three seconds, 5 seconds, 10, 20, or 30 seconds, for example. The head-mounted system of FIG. 17, and also the stand-mounted portable optical device of FIG. 19, described hereinafter, can also achieve this degree of stability.

FIG. 19 is an illustration of a tripod-mounted portable optical device 1908. In particular, the device 1908 is similar to the embodiments described in connection with FIGS. 1-10B and includes a clamp 1968 that secures the device to the tripod. Other types of stands besides tripods can also be used, such as monopods or other stands (not illustrated in FIG. 19). For use, the patient-user rests the patient-user's face against an eyecup 1964 to look through the open view device. A front 1966 of the device is open-view so that the patient-user can look through it. The device 1908 also includes a black knob on the top, which is used to adjust the pupillary distance of the device.

FIG. 20 is a schematic diagram illustrating a portable a portable optical device 2008 that can be used in connection with various embodiments. The optical diagram illustrates an open-view wavefront aberration that are, pupil law mentor, and keratometry. There are two sources of illumination, including a laser diode 2080 that is used to illuminate a point of light on the retina of the eye 1754, and another, namely light emitting diodes 2070, that are mounted on an eye cup of the device 2008 and used to illuminate the cornea and the pupil of the eye 1754. By ensuring that the two illumination sources are sufficiently separated in wavelength, appropriate beam splitters 2074, 2076, and 2078 can be chosen to ensure that the light reflecting off of the retina is sent to the camera 2084 that performs wavefront aberrometry, while light reflecting off the cornea is sent to a pupil camera 2088. The device also includes focusing optics 2090 for focusing light into the pupil camera 2088, as well as focusing optics 2086 for focusing light from the retina onto the wavefront aberrometer camera 2084.

The laser diode 2080 produces light 2082 that is inbound laser light into the eye, which travels through the beam splitters and through a tunable optics 2072 into the retina. Laser light that is reflected off of the retina, 2094, enters the wavefront camera 2084. Light 2092 from the LEDs 2070, which is reflected off of the cornea, enters the focusing optics 2090 and enters the pupil camera 2088. The device 2008 features both the tunable optics 2072 and an open view, in part provided by a transparent window 2096, which allows the eye 1754 to see through the portable optical device 2008 to external target indicia 252 that are separated from the housing of the portable optical device 2008. In this manner, the eye 1754 is permitted to be relaxed and substantially unaccommodated for measurements.

FIG. 21 includes two images of a human pupil 2198 that is imaged with a portable optical device, such as the device 2008 of FIG. 20, having eight LEDs 2070 in a circular pattern. Similar images can be taken with other numbers of LEDs, such as four LEDs in a square pattern, for example. In the images, the pupil 2198, iris 2101, eyelashes 2103, and cornea and conjunctiva 2105 are clearly visible and identifiable. The reflections 2170 of the LEDs 2070 reflecting off of the cornea can be used for pupil imaging and keratometry.

FIG. 22 includes a series of three keratometry images at a closer distance (left), medium distance (middle), and further distance (right). Keratometry data can be derived from the people camera images by processing (e.g., thresholding) the image. In this example, all pixel values were set under a threshold to zero, which results in extraction of the image of the LED light sources, since they are the brightest features in the images. The distance from the LEDs to the surface of the eye can be determined by various methods, including direct measurements with distance sensors e.g., physical ruler, optic or acoustic-based sensors, or through image processing of the pupil camera image. The position of the LEDs on the pupil camera image, actual physical positions of the LEDs, and the estimated distance of the LEDs from the surface of the eye, can all be used to determine the curvature of the cornea (keratometry values) using standard formulas. In this manner, by including a pupil camera on devices that are used in embodiments, keratometry data may be obtained in order to inform contact lens prescriptions.

FIG. 23 is a flow diagram illustrating how alignment of device optics and patient-user pupils may be performed according to various embodiments. In particular, FIG. 23 shows an alignment procedure 2300. In the procedure, at 2307, the device is placed on the head of the patient, as illustrated in FIG. 17. Nonetheless, it should be understood that similar procedures can be performed for handheld, shoulder-mounted, and stand mounted portable optical devices. However, head-mounted, shoulder-mounted, and tripod-mounted or other stand-mounted devices are preferred for longevity of alignment stability for best alignment and measurement results according to embodiments.

At 2309, a position of straps, such as the head strap and other head strap, 1736 and 1738, is adjusted such that the patient can see through the device via open-view ports. At 2311, a pupil camera acquires images of the patient's eye and displays them on a digital screen, such as the digital screen of the devices described in connection with FIGS. 1-10B.

At 2313, software processes the people images to determine pupil position and whether any positional adjustment is required to align the eye with the device properly. At 2315, the software provides instructions on how to make positional adjustments to achieve proper alignment with the device.

Then, in a first case of operator-assisted alignment, at 2317, an operator, such as the operator 1530 in FIG. 15, makes positional adjustments while looking at the digital screen displaying images from the pupil camera. The adjustments might be made by physically manipulating the device or by remotely controlling the devices built-in motors, especially if the operator is not on-site with the patient-user. In a second case, at 2319, a case of self-alignment by the patient, the patient-user physically manipulates the device to make positional adjustments and manipulates the optics while looking through the device at the digital screen displaying images from the people camera, or while receiving haptic or audio feedback, either from the device itself, or from a tablet or other secondary device, such as the tablet 1532 in FIG. 15. In a third case, at 2321, the device performs self-alignment by using built-in motors, based on instructions provided by software. At 2323, for the operator-assisted alignment and self-alignment, the software determines if both eyes properly aligned with the device. At 2325, the software may determine that both eyes are properly aligned, in which case, at 2327, the device proceeds with taking measurements of the patient's eyes. However, if the software determines at 2323 that both eyes are not properly aligned with the device, and more particularly, if one or both eyes are not properly aligned at 2329, then at 2331, the alignment process is repeated for the improperly aligned eye or eyes.

FIG. 24 is a flow diagram illustrating a process to obtain various eye health parameters from a portable optical device according to embodiments. Some or all of these eye health parameters can be measured simultaneously, or in feedback loops to iterate and refine the measurements. Some or all of these eye health parameters can be combined, in addition to being combined with other personal demographic or health history data, in order to assist an eye care professional or an artificial intelligence routine that is part of corresponding executable code in various embodiments, to provide diagnosis and prescription for eye health conditions of the patient-user.

At 2433, after the device is aligned with one or both of the patient-user's pupils, four different processes of measurement may be obtained, either in sequence, or in some cases simultaneously, as will be understood by those of skill in the art in view of this disclosure. At 2435, pupil imaging can be performed, as previously described in this disclosure. At 2437, keratometry measurements can be obtained, for example based on the pupil imaging at 2435. At 2439, wavefront aberrometry can be performed. At 2441, subjective refraction measurements, using tunable lens optics set to the patients manifest (existing or habitual) prescription, or with a predetermined optical power, can be performed. The subjective refraction 2441 can be used as an input or precursor to wavefront aberration 2439. However, wavefront aberrometry 2439 can also be performed as a starting point to obtain the subjective refraction 2441. The wavefront aberrometry can be used at 2447 to obtain objective refraction data, with both low- and high-order aberrations. At 2449, the tunable lens optics can be modified to alter the vision of the patient-user. This can include partially or fully correcting the patient-user's refractive errors, minimizing wavefront error, or optimizing another image quality metric. At 2451, detection of dry eye based on wavefront aberrometry data may be performed. Then at 2453, an eye care professional can review eye health data and provide a diagnosis of dry eye if needed.

Furthermore, after the modification of tunable lens optics at 2449, retinal imaging 2455 can be performed. At 2457, and eye care professional can review by healthcare data and provide diagnosis of retinal disease based on the retinal imaging 2455. The retinal disease can include, for example, diabetic retinopathy, macular degeneration/AMD, retinal blending, etc. At 2459, subjective refraction and visual acuity measurements may also be performed, for example after minimizing wavefront error using the tunable lens settings at 2449, for example. The subjective refraction and visual acuity measurements may be used to inform an eye care professional, or artificial intelligence, at 2461, in order to refine and eyeglasses or contact lens prescription as needed. At 2463, the eye care professional or artificial intelligence can provide the eyeglasses or contact lens prescription to the patient-user or to an optical supplier.

The pupil imaging at 2435 may be used to produce pupil measurements at 2443, which can inform the contact lens prescription obtained at 2461, for example. Furthermore, the pupil measurements 2443 can be used as part of the eye health data review at 2453 or the retinal disease diagnosis at 2457, for example.

The keratometry measurements at 2437 can be used to determine K values at 2445, which can also inform the dry eye, Retinal disease, or eyeglasses or contact lens prescription determination.

FIG. 25 is a photograph showing an operator 1530 assisting a patient-user 1212 to perform alignment of a portable optical device 2508 with the patient-user's pupils. The patent. The patient-user views through the device 2508 via an open-view channel of the device, 1748. Alignment is achieved based on images 2565 from a pupil camera that is included on the portable optical device 2508. The pupil camera obtains the images 2565, which are displayed on a digital screen on the device 2508, and the operator 1530 views these images, which can be similar to those shown in FIGS. 21-22 and 26, for example, until good alignment of the measurement optics of the device 2508 with the patient's pupil is obtained.

FIG. 26 is a diagram showing an example photograph illustrating how an operator can manually align a portable device to a patient-user's pupil using a pupil camera image displayed on the device. A digital display 2667 is provided on the device, the patient views through an open-view channel 1748 of the device, and the patient's field of view 2669 when looking through the device's open-view channel is shown. The pupil camera images 2565, as seen through the open-view channel of the device, on the digital display, facilitate self-alignment of the measurement optics with the patient's pupil. In the case of a patient self-aligning the device to the patient-user's pupil, the patient-user may look through the open-view system at a digital screen such as the digital display 2667, which can be provided on a tablet, smart phone, or computer, for example, which can have the patient's pupil camera image displayed thereon. Alignment instructions may be given to the patient-user with audio, haptic, or visual feedback to help refine the alignment, as described further hereinabove.

FIG. 27 is a flow diagram outlining how a pupil camera, and the images provided thereby, can be processed in order to determine a position of a pupil, which can be used to provide feedback on how to align the devices measurement optics to the patient's pupil. At 2769, image binning is performed to reduce image size to improve processing time. At 2771, thresholding is performed, as previously noted. At 2773, image filtering is performed (e.g., via a median filter) to eliminate connected dots (of the pupil imaging LEDs) and to remove noise after binning the image. At 2775, pupil detection is performed. Finally, at 2777, feedback is provided to align the device to the patient's pupil. At that time, the feedback may be automated via motorized actuators that the corresponding executable code automatically commands to move horizontal and vertical rails of the optic carriage to the correct position, as described in connection with FIG. 17, or the feedback may be to the patient-user, or to an operator, such that manual positioning may be performed, such as using the lead screw and knob for horizontal and vertical adjustments, as described in connection with FIG. 17.

FIG. 28 is a flow diagram outlining how a sequence of images captured by a pupil camera can be processed to obtain keratometry values of an eye in various embodiments. At 2879, a sequence of images from a pupil camera [P(t)] is obtained. At 2881, feature extraction is performed. At 2883, ring segmentation is performed, using, for example, ellipse fitting. At 2885, pupil segmentation is performed, such as by thresholding, as previously described.

Based on the feature extraction 2881, pixel size 2887, focus score 2889, and vertex distance 2891 can be obtained. Pixel size is the size of pixel in the pupil plane, in millimeters. The focus score is a metric representing how well focused the pupil is. The vertex distance is an estimate of distance between the pupil plane and the device. At 2883, based on the pupil segmentation 2885, the variables pupil size [s(t)] and pupil position [(x, y), t] can be obtained. Finally, based on the variables pupil size and pupil position, the ring segmentation, and the pixel size, focus score, and vertex distance, at 2895, keratometry values can be calculated using standard formulas, such as K1, K2, and base curve.

FIG. 29 is a schematic diagram illustrating a cloud environment 2900 showing potential interconnectedness of different components of a cloud ecosystem and how eye health data can be shared between a patient-user and an eye care professional and or artificial intelligence, and how therapeutic output, such as a prescription or diagnosis, can be relayed to a therapy provider, all according to embodiments further described herein in connection with the other drawings.

The cloud 2900 manages transfer of information between entities via wired or wireless communication 2992 the entities or wired or wireless communication 2992 from the entities. The data can then be sent to servers to be further analyzed and stored in a database. The database can then be accessed by an authorized eye care professional from any Internet connected device, such as a computer, tablet, smart phone, etc. Alternatively, the patient-user's data taken by the hardware can be uploaded directly to the eye care professional from any Internet connected device, such as a computer, tablet, smart phone, etc.

In particular in FIG. 29, an optical retailer 2997, which can provide eyeglasses, contact lenses, or eye health therapy, for example, can communicate through the cloud with an eye care professional 1216, which can provide a prescription or therapy order, for example. Alternatively, the optical retailer 2997 can receive a prescription from artificial intelligence housed on a server 2999 that determines a prescription or a diagnosis based on data received from the device that is used to measure a patient-user 1212. Still further, the optical retailer 2997 can receive a prescription, for example, directly from the device that is with the patient-user 1212 at the time of eye examination, via the device having Wi-Fi connectivity with the cloud, or a wired connection to the cloud, for example. Still further, artificial intelligence that is capable of making a diagnosis or prescription may be present directly on the device that is with the patient-user 1212 and may provide a prescription to the patient-user 1212, for example. The patient-user 1212 may then order eyeglasses, contact lenses, or request therapy from the optical retailer 2997 via a wired or wireless connection, for example.

In various embodiments, the eye care professional 1216 and a server terminal, which can include a computer, tablet, smart phone, Smart watch, digital health wearable, etc., can be enabled by the corresponding executable code at the location of the patient-user 1212 to participate in an eye examination of the patient-user 1212 using the device. This can be performed via the device directly streaming video or other data to the eye care professional 1216, or via a tablet or other connected secondary device, such as the tablet 1532 in FIG. 15, providing a link for audiovisual communication or other data connection between the eye care professional and either the patient-user or the portable optical device that is with the patient-user 1212.

In still other variations of embodiments, the device that is with the patient-user 1212 may communicate directly with a server 2999 that runs a portion of corresponding executable code that assists with alignment between the patient-user and the device, diagnosis based on data from the device, or prescription based on data from the device, for example. Still further, the server 2999 with artificial intelligence can perform other functions of the operator 1530 or the eye care professional 1216 shown in FIG. 15, in order to interact with the patient-user 1212, the device that measures the patient-user, or a peripheral device such as the tablet 1532 in FIG. 15. In this manner, it will be understood that a wide variety of embodiments can be performed consistent with the claims and particular embodiments described herein.

FIG. 30 is a flow diagram illustrating an embodiment procedure 3000 for eye examination. At 3002, a portable optical device is delivered to a patient-user at a location outside of a clinical setting. The delivery is in a manner that enables the patient-user to have use of the device in conducting an eye examination. At 3004, corresponding executable code is provided to the patient-user. The corresponding executable code is executable with the patient-user use of the device. At 3006, during patient-user use of the device in conducting the eye examination, the corresponding executable code is executed and enables artificial intelligence (AI) to have participation in the eye examination, including enabling the AI to generate a diagnosis of eye health of the patient-user.

In various embodiments that will be understood further in reference to the other drawings and description herein, the eye examination procedure 3000 can further include any of the features of previous embodiments, wherein the AI takes the place of the physician, and particular the embodiment of FIG. 11.

FIG. 31 is a schematic block diagram illustrating an embodiment eye examination system 3100, corresponding to the eye examination procedure 3000 of FIG. 30. The system 3100 includes a portable optical device 3108, as well as corresponding executable code 3110. The portable optical device is delivered to a patient-user at a location outside of a clinical setting. The device is delivered in a manner that enables the patient-user to have use of the device in self-operating and conducting an eye examination of an eye of the patient-user. The corresponding executable code is executable with the patient-user use of the device, during patient-user use of the device conducting the eye examination, namely the device 3108. The corresponding executable code 3110 is executed and enables AI participation in the eye examination including enabling the AI to generate a diagnosis of eye health of the patient-user.

The eye examination system 3100, with its portable optical device 3108 and corresponding executable code 3110, can have any of the features described in connection with FIG. 11, such as random and remote location with respect to the AI, any of the cited example locations, preloading the corresponding executable code, using a portable digital processing device, and downloading the corresponding executable code in the various ways cited.

The AI in FIGS. 30 and 31 can reside in the portable optical device or remotely, such as in a cloud-based or clinic-based server system. Communication using the example means described in connection with FIG. 29 may be used for the AI to participate, generate, communicate, etc. The pupil camera and other alignment techniques described hereinable are particularly advantageous for remote-based eye examination due to the longevity of alignment stability that can be provided, enabling remote eye examinations where they would not otherwise be possible in many circumstances.

While example embodiments have been particularly shown and described, it will be understood by those skilled in the art that various changes in form and details may be made therein without departing from the scope of the embodiments encompassed by the appended claims.

For example, the term 'hand-held configuration' with respect to the portable optical device is not intended to restrict use by the operator to operating the portable optical device while holding it in his hands. As described above, the hand-held configuration allows the operator to balance the portable optical device on a tabletop, on a stand, etc. Furthermore, embodiments can be advantageously head-mounted or shoulder-mounted on the patient-user, or mounted on other types of stands such as tripods, facilitating alignment between optical elements of the portable optical device and the patient-user's pupil or pupils. Such design and configuration of the portable optical device is in contrast to the prior art pieces of clinical equipment that are large and stationary, or which do not have features or configurations facilitating alignment.

As used herein, 'self-operating' and 'self-conducting' an eye (vision) exam using the portable optical device may include another onsite operator or a local assisting in taking measurements using the optical device on the patient-user (e.g., a parent, relative, caregiver, and the like using the optical device on their child). As used herein. 'self-operating' and 'self-conducting' an eye (vision) exam using the portable optical device also includes using a local or remote artificial intelligence resource assisting in taking measurements using the optical device on the patient-user (e.g., a parent, relative, caregiver, and the like using the optical device on their child). An artificial intelligence resource can be a local firmware or software executable code located in the device or another local device, or firmware or software executable code operating in the cloud and in operational communication via a remote connection, for example.

Instead of or in addition to the physician in the above description, another qualified health professional, such as an optometric technician or an ophthalmic technician, may view and/or guide the remote eye (vision) exam. In other embodiments, the physician/health professional/technician may be replaced with a virtual health professional (avatar), programmed agent/robot (artificial intelligence operating algorithms in executable code such as software or firmware), or the like.

Although video conferencing is mentioned throughout the above description, it is understood by the skilled in the art that audio only (telephone) conferencing may be suitable in some embodiments. Further the video conferencing or videotelephony technology may be proprietary or third-party solution software.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. An eye examination method, comprising:
   delivering a portable optical device to a patient-user at a location outside of a clinical setting, said delivering being in a manner enabling the patient-user use of the device in conducting an eye examination;
   providing to the patient-user corresponding executable code that is executable with patient-user use of the device, the corresponding executable code configured to be in operative communication with the device during the patient-user use including determining a degree of alignment of the device with a pupil of an eye of the patient-user during the patient-user use; and
   during patient-user use of the device conducting the eye examination, the corresponding executable code being executed and enabling a diagnoser participation in the eye examination via audio-visual means, including enabling the diagnoser to generate a diagnosis of eye health of the patient-user.

2. A method as claimed in claim 1, wherein the location is random and remote with respect to a physician as the diagnoser, and the location is any of: a residence, a patient-specified address, a school address, a location in the community of the patient-user, a place without a health professional present, a kiosk, a place of employment, and an optical retail store.

3. A method as claimed in claim 1, wherein the diagnoser is any one or combination of a physician, a health professional, and artificial intelligence software; and wherein the location is any of: a residence, a patient-specified address, a school address, a location in the community of the patient-user, a place without any health professional present, a kiosk, a place of employment, and an optical retail store.

4. A method as claimed in claim 1, wherein the corresponding executable code is provided to the patient-user by any of: being preloaded on the portable optical device, being preloaded on a portable digital processing device, or being available for download by the patient-user from a cloud server, through a website, or through an online platform, said download by the patient-user being to a computer, laptop, notebook, tablet, digital health wearable, or mobile phone of the patient-user or accessible by the patient-user; and wherein the preloaded portable digital processing device is a laptop, notebook, tablet, digital health wearable, or mobile phone and is included in the delivery of the optical device to the patient-user.

5. A method as claimed in claim 1, wherein the portable optical device is configured to be shoulder-mounted to a shoulder of the patient-user, head-mounted to a head of the patient-user, or stand-mounted during the eye examination; and wherein the portable optical device includes a pupil camera, and the corresponding executable code is configured to assist in alignment of one or more optical elements of the portable optical device with the pupil of the eye of the patient-user, the alignment being maintained for a sufficient amount of time for the portable optical device to (i) acquire a temporal sequence of wavefront aberrometry measurements of the eye, and to (ii) obtain a subjective refractive preference of the patient-user while the patient-user views one or more external target indicia through at least one visual tunable optical element of the portable optical device.

6. A method as claimed in claim 5, wherein the pupil camera provides alignment feedback in a manner enabling any one or more of: the patient-user, an operator, a remote physician, and the corresponding executable code to adjust alignment of the one or more optical elements of the portable optical device with the pupil of the eye of the patient-user, said adjusting alignment being by manual or electro-mechanical means.

7. A method as claimed in claim 1, wherein the portable optical device includes a wavefront aberrometer and determines an optical property of the eye of the patient-user based on optical measurement data, the optical measurement data including any of: wavefront aberrometry data, wavefront aberrometry data in the form of Zernike coefficients, wavefront aberrometry data in the form of spot diagram images, image quality metrics (IQMs), retinal IQMs, cornea curvatures, optical refractive power, final refractive care prescriptions, axial length as a distance from the corneal surface to an interference peak corresponding to the retinal pigment epithelium/Bruch's membrane, biometric data, fundus imaging, corneal imaging, pupil images, keratometry readings, and subjective refraction indications.

8. A method as claimed in claim 7, wherein determining the optical property based on wavefront aberrometry data includes performing a temporal wavefront analysis responsive to the portable optical device acquiring a temporal sequence of wavefront aberrometry measurements of the eye.

9. A method as claimed in claim 7, wherein the portable optical device further includes one or more visual tunable optical elements, and a pupil camera;

and wherein the portable optical device during the eye examination of the patient-user generates the optical measurement data by any of: wavefront imaging, use of the tunable optical elements, pupil imaging, and keratometry.

10. A method as claimed in claim 1, wherein the portable optical device is of a design that is: (a) binocular testing two eyes at a time or monocular testing one eye at a time, and (b) open-view.

11. A method as claimed in claim 1, wherein enabling the diagnoser to generate a diagnosis of eye health of the patient-user includes enabling a physician to generate a corrective lens prescription for the patient-user based on data received from the eye examination by the portable optical device, the data received including subjective refractive preference of the patient-user with the patient-user having an open view through the portable optical device; and the method further comprising initiating an order for eyeglasses or contact lenses for the patient-user using the physician-generated corrective lens prescription.

12. An eye examination method as claimed in claim 1 wherein, the corresponding executable code provides uploading and live streaming of optical measurement data from the eye examination to the diagnoser, including the corresponding executable code enabling any one or combination of: (i) live streaming of optical measurement data during patient-user use of the device conducting the eye examination, and (ii) uploading optical measurement data from patient-user use of the device, such that the optical measurement data is received and reviewed by the diagnoser in a manner enabling the diagnoser to generate any of: a diagnosis of eye health for the patient-user, a refractive correction for the patient-user, an eyeglass prescription for the patient-user, and a contact lens prescription for the patient-user.

13. An eye examination system comprising:

a portable optical device configured to be deliverable to a patient-user at a location outside of a clinical setting, the device being delivered in a manner enabling the patient-user use of the device in conducting an eye examination; and corresponding executable code executable with the patient-user use of the device, the corresponding executable code configured to be in operative communication with the device during the patient-user use including determining a degree of alignment of the device with a pupil of an eye of the patient-user during the patient-user use, and during patient-user use of the device conducting the eye examination, the corresponding executable code being executed and enabling a diagnoser participation in the eye examination via audio-visual means, including enabling the diagnoser to generate a diagnosis of eye health of the patient-user.

14. A system as claimed in claim 13, wherein the diagnoser is any one or combination of: a physician remote from the patient-user, a health professional remote from the patient-user, and artificial intelligence software; and wherein the location is random and remote with respect to the physician and the health professional.

15. A system as claimed in claim 13, wherein the location is any of: a residence, a patient-specified address, a school address, a location in the community of the patient-user, a place without any health professional present, a kiosk, a place of employment, an optical retail store, and the like; and wherein the portable optical device is portable to the patient-user.

16. A system as claimed in claim 13, wherein the corresponding executable code is preloaded on a portable digital processing device included in delivery of the portable optical device to the patient-user.

17. A system as claimed in claim 14, wherein the portable digital processing device is a laptop, notebook, tablet, digital health wearable, or mobile phone.

18. A system as claimed in claim 13, wherein the corresponding executable code is downloadable by the patient-user from a cloud server, through a website, or through an online platform to a laptop, notebook, tablet, digital health wearable, or mobile phone at the patient-user's disposal.

19. A system as claimed in claim 13, wherein the portable optical device includes a wavefront aberrometer and is of a, binocular or monocular, open-view design such that the portable optical device determines optical properties of each eye of the patient-user.

20. A system as claimed in claim 13, wherein the corresponding executable code streams wavefront aberrometry data from the portable optical device to the diagnoser via the audio-visual means in a manner enabling generation of a refractive correction or corrective lens prescription that is saved in an electronic format supporting online ordering of a pair of eyeglasses or contact lens for the patient-user.

* * * * *